United States Patent
Ouellet et al.

(10) Patent No.: US 6,784,289 B2
(45) Date of Patent: Aug. 31, 2004

(54) TRANSLATIONAL REGULATORY ELEMENTS

(75) Inventors: Thérèse Ouellet, Nepean (CA); Brian M. Miki, Ottawa (CA); Elizabeth Foster, Nepean (CA); Teresa Martin-Heller, Gloucester (CA); Lining Tian, London (CA); Daniel C. Brown, Ilderton (CA); Peijun Zhang, Nepean (CA); Jiro Hattori, Ottawa (CA); Kamal Malik, Ottawa (CA); Keqiang Wu, Nepean (CA); David A. Theilmann, Summerland (CA); Raymond Tropiano, Gloucester (CA)

(73) Assignee: Her Majesty the Queen in Right of Canada, as represented by the Minister of Agriculture and Agri-Food, Ottawa (CA)

( * ) Notice: Subject to any disclaimer, the term of this patent is extended or adjusted under 35 U.S.C. 154(b) by 0 days.

(21) Appl. No.: 09/747,007

(22) Filed: Dec. 21, 2000

(65) Prior Publication Data

US 2002/0073444 A1 Jun. 13, 2002

Related U.S. Application Data

(60) Provisional application No. 60/172,813, filed on Dec. 21, 1999.

(51) Int. Cl.[7] .......................... C07H 21/04; C12N 15/00

(52) U.S. Cl. .................. 536/24.1; 536/23.1; 435/320.1
(58) Field of Search .............................. 536/22.1, 23.1, 536/24.1; 435/468, 320.1, 410, 414

(56) References Cited

U.S. PATENT DOCUMENTS 5,824,872 A * 10/1998 Miki et al. .................. 800/205

OTHER PUBLICATIONS

No additional reerences are cited by the Examiner.*

* cited by examiner

*Primary Examiner*—James Ketter
*Assistant Examiner*—David Lambertson
(74) *Attorney, Agent, or Firm*—Quarles & Brady LLP

(57) ABSTRACT

The present invention is directed to translational regulatory elements that mediate the amount of protein produced within a host capable of expressing a construct comprising one or more translational regulatory elements in operative association with a gene of interest. These translational regulatory elements were derived from T1275 (tCUP) and exhibit a high degree of similarity with members of the RENT family of repetitive elements. Translational regulatory elements are disclosed that either increase or decrease he amount of protein produced within the host organism. These translational elements are operative in a wide range of hosts including plant, animals, yeast, fungi and bacteria. Analogs, derivatives and fragments of these translational elements are also disclosed.

12 Claims, 52 Drawing Sheets

```
                             10         20         30         40         50
                        1 ---------- ---------- ---------- ---------- ----------
tCUP
                        1 ---------- --------A- ---------- ATTGTAAGCG GGATAACAAT
Rent1.
                        1 ---------- --------AT GTTGTGTGGA ATTGTGAGCG GGATAACAAT
RENT2.
                        1 TT-------- ---------- ---------- ---------- ----------
RENT3.
                        1 ---------- ---------- -------GGA ATTGTGAGCG G-ATAACAAT
RENT5.
                        1 TTTATGCTTC CGGCTCGTAT GTTGTGTGGA ATTGTGAGCG G-ATAACAAT
RENT7.

60         70         80         90        100
                       51 ---------- ---------- ---------- ---------- ----------
tCUP
        100
Rent1.                 51 TTCACACAGG AAACAGCTAT GACCATGATT ACGCCAAGCT TTTAATACGA
        100
RENT2.                 51 TTCACACAGG AAACAGCTAT GACCATGATT ACGCCAAGCT CT-AATACGA
        100
RENT3.                 51 ---------- ---------- ---------- ---------- ----------
        100
RENT5.                 51 TTCACACAGG AAACAGCTAT GACCATGATT ACGCCAAGCT CT-AATANGA
        100
RENT7.                 51 TTCACACAGG AAACAGCTAT GACCATGATT ACGCCAAGCT CT-AATACGA
        100

110        120        130        140        150
                      101 ---------- -------TTA TAATTACAAA ATTGATTCTA GTATCTTTAA
tCUP
        150
RENT1.                101 CTCACTATAG GGAAAGCTTA TAATTACAAA ATTGATTCTA GTATTTTTAA
        150
RENT2.                101 CTCACTATAG GGAAAGCTTA TAATTACAAA ATTGATTCTA GTATTTTTAA
        150
RENT3.                101 ---------- ---------- ---------- ---GATTCTA GTTTTTTTAA
        150
RENT5.                101 CTCACTATAG GGAAAGCTTA TAATTACAAA TTTGATTCTA GTATTTTTAA
        150
RENT7.                101 CTCACTATAG GGAAAGCTTA TAATTACAAA ATTGATTATA GTACTTTTAA
        150
```

Figure 1C1

```
              160        170        180        190        200
tCUP      151 TTTAATGCTT ATACATTATT AATTAATTTA GTACTTTCAA TTTGTTTTCA
      200
RENT1.    151 TTTAATATTT TTACATTATT AATTAATTTA GAAGTTTTAA TTTTTTTTCA
      200
RENT2.    151 TTTAATATTT ATACATTATT AATTAACTTA GTACTTTCAA TTCGTTTTCA
      200
RENT3.    151 TTTAATATTT ATACATTATT AATTAATTTA GTTCTTTCAA TTTGTTTTCA
      200
RENT5.    151 TTTAATATTT ATACATTATT AATTAATTTA GTACTTTCAA TTTGTTTTCA
      200
RENT7.    151 TTTAATATTT ATACATTATT AATTAATTTA GCACTTTCAA TTTATTTTCA
      200

210        220        230        240        250
tCUP      201 GAAATTATTT TACTATTTTT TATAAAATAA AAGGGAGAAA ATGGCTATTT
      250
RENT1.    201 GAAATCATTT TACTATTTTT -ATAAAAACA AAAGGGAAAA GTGGTTATTT
      250
RENT2.    201 AAAATTATTT TACTATTTTT TGTAAAATAA AAGGGAGAAA ATGGCTATTT
      250
RENT3.    201 GAAATTATTT TACTATTTTT TATAAAATAA AAGGGAGAAA ATGGCTATTT
      250
RENT5.    201 GAAATCATTT TACTATGGTT TATAAAATAA AAGGGAGAAA ATGGCTATTT
      250
RENT7.    201 GAAACCATTT TACTATTTTT TATAAAATAA AAGGGACAAA ATGGCTATTT
      250

260        270        280        290        300
tCUP      251 AAATACTAGC -CTATTTTAT TTCAATTTTA GCTTAAAATC AG-CCCCAAT
      300
RENT1.    251 AAATACTAGC CCTATTTCAT TTCAATTATA GCCTAAAATC AGCCCC-AAT
      300
RENT2.    251 AAATACTAGC CCTATTTTAT TTCAATTTTA GCCTAAAATC AGCCCCCAAT
      300
RENT3.    251 AAATACCAGC CCTATTTTAT TTCAATTTTA ACCTAAAATC AGCCCC-AGT
      300
RENT5.    251 AAATACTAGC CCTATTTTAT TTCAATTTTA GCCTAAAATC AGCCCC-AAT
      300
RENT7.    251 AAATACCAAC ACTATTTTAT TTCAATTTTA GCCTAAAATC AAACCC-AAT
      300
```

Figure 1C2

```
              310        320        330        340        350
tCUP     301  TAGCCCCAAT TTCAAATTCA AATGGTCCAG CCCAATTCCT AAA-TAACCC
    350
RENT1.   301  TAACCCCAAT TCCAAATTCA AACGGGCCAG CCCAATTCCT AAAATGACCC
    350
RENT2.   301  TAACCCCAAT TTCAAATTCA AATGGGACAG CCCAATTCCT AAAATAACCC
    350
RENT3.   301  TAGCCCC--- ---------A AACGGCCCAT CCCAATTCCT AAAATAACTC
    350
RENT5.   301  TAACCCCTAT TTCAAATTCA AACGGGCTAG CCCAGTTCCT AAAATAACCC
    350
RENT7.   301  TAACCCC--- ---------A AACGGGCCAG CCCAATTCCT AAAACAACCC
    350

360        370        380        390        400
tCUP     351  ACCCCTAACC C--------- ----GCCCGG TTTCCCCTTT TGATCCAGGC
    400
RENT1.   351  GCTCCTAACC CGCTTTTCCA ACCCGCCCGG TTTCCCCTTT TGATCCAGGC
    400
RENT2.   351  GCCCCTAACC CTCTTATCCA ACCCACCCGA TTTCCCCTTT TGATCCAGGT
    400
RENT3.   351  GCCCCTAACC CGCTTATCCA ACCCGCCCGG TTCCC-CTTT TGATCCAGGC
    400
RENT5.   351  TCCCCTAACC CGCTTATCCA ACCCGCCCTG TTTCCCCTTT TGATCCAGGC
    400
RENT7.   351  GCCCCTAACC CGCTTATCCA ACCCGCCCGA TTTCCTCTTT TGATCCAGGC
    400

410        420        430        440        450
tCUP     401  CGTTGATCAT TTTGATCAAC GCCCAGAATT TCCCCTTTTC CTTTTTTAAT
    450
RENT1.   401  TGTTGATCAT TTTGATCAAC GGCCAGAATT TCCCCTTTCC --TTTTTAAT
    450
RENT2.   401  TGTTGATCAT TTTGATCAAC GACCAGAATT TCCCCCTTCC TGTTTTTAAT
    450
RENT3.   401  CGTTGATCAT TTTGATCAAC GACCAGAATT TCCCCTTTCC -TTTTTTAAT
    450
RENT5.   401  CGTTGATCAT TTTGATCAAC GACCAAAATT TCCCCTTT-C CTTTTTTAAT
    450
RENT7.   401  CGTTGATCAT TTTGATCAAC GGCCAGAATT TCCCCTTTCC -TTTTTTCAT
    450
```

Figure 1C3

```
              460        470        480        490        500
tCUP     451 TCCCAAACAC C-CCTAACTC TATCCCATTT CTCACCAACC GCCACATATG
    500
RENT1.   451 TCCCAAACAC CCCCCAACCT TATCCCGTTT CTCACCAACC GCCAGATCT-
    500
RENT2.   451 TCCCAAACAC CCCCCAACCC TATCCCATTT CTCACCAACC GCCAGATCT-
    500
RENT3.   451 TCCCAAACAC CGCC-AAACC TATCCCATTT CTCACCAACC GCCAGATCTA
    500
RENT5.   451 TCCCAAACAC CCCC-AACCC TATCCCATTT CTCACCAACC GCCAGATCT-
    500
RENT7.   451 TCCCAAACAC CCCC-AAACC TATCCCATTT CTCACCAACC GCCAGATCTA
    500

510        520        530        540        550
tCUP     501 AATCCTCTTA TCTCTCAAAC TCTCTCGAAC CTTCCCCTAA CCCTAGCAGC
    550
RENT1.   501 -ATCCTCTTA TCTCTCAAAC TCTCTCGAAC CTTCCCCTAA CCCTAGCAGC
    550
RENT2.   501 -ATCCTCTTA TCTCTCAAAC TCTCTCGAAC CTTCCCCTAA CCCTAGCAGC
    550
RENT3.   501 T--CCTCTTA TCTCTCAAAC TCTCTCGAAC CTTCCCCTAA CCCTAGCAGC
    550
RENT5.   501 -ATCCTCTTA TCTCTCAAAC TCTCTCGAAC CTTCCCCTAA CCCTAGCAGC
    550
RENT7.   501 T--CCTCTTA TCTCTCAAAC TCTCTCGAAC CTTCCCCTAA CCCTAGCAGC
    550

560        570        580        590        600
tCUP     551 CTCTCATCAT CCTCACCTCA AAACCCACCG GAATACATGG CTTCTCAAGC
    600
RENT1.   551 CTCTCATCAT CCTCACCTCA AAACCCACCG GCCACCATGG CCTCTAGAG-
    600
RENT2.   551 CTCTCATCAT CCTCACCTCA AAACCCACCG GCCACCATGG CCTCTAGAG-
    600
RENT3.   551 CTCTCATCAT CCTCACCTCA AAACCCACCG GCCACCATGG CCTCTAGAGG
    600
RENT5.   551 CTCTCATCAT CCTCACCTCA AAACCCACCG GCCACCATGG CCTCTAGAG-
    600
RENT7.   551 CTCTCATCAT CCTCACCTCA AAACCCACCG GCCACCATGG CCTCTAGAGG
    600
```

Figure 1C4

```
              610        620        630        640        650
tCUP     601  CGTGGAAACC TTATACTCAC CTCCCTTTGC TCTTACAGTA CTC-GGCCGT  650
RENT1.   601  ---GATCCCC GGGTGGTCAG TCCCTTATG- --TTAC---- --------GT  650
RENT2.   601  ----GA---- ---------- -TCCCCG--- ------GGTG GTC-AGTCCC  650
RENT3.   601  ATC----CCC GGGTGGTCAG TCCCTTATGT NA------CG NCCTAAATGN  650
RENT5.   601  ---GATCCCC GGGTGGTCAG TCCCTTATG- --TTACG--- ----------  650
RENT7.   601  ATC----CCC GGGTGGTCAG TCCCTTATGT TA------CG TCCTN-----  650

660        670        680        690        700
tCUP     651  CGACCGCGGT ACCCGGG... .......... .......... ..........  700
RENT1.   651  C--------- --CTNAA... .......... .......... ..........  700
RENT2.   651  TTAT-GTG-- ---CGTC... .......... .......... ..........  700
RENT3.   651  CCGNCCTGNN NNNNN-C... .......... .......... ..........  700
RENT5.   651  ---------- TCC---... .......... .......... ..........  700
RENT7.   651  ---------- -------... .......... .......... ..........  700
```

Figure 1C5

<sup>a</sup> NdeI position +30    ACA TAT GAA

<sup>b</sup> BglII position +29    ACA GAT CT

<sup>c</sup> NcoI position 0    CC ACC ATG GCC TCT AGA GGA TCC CCG GGT GGT CAG TCC CTT ATG tCUP initiation site GAA TAC ATG G  /... tCUP leader .../  CCG GGT GGT CAG TCC CTT ATG Kozak consensus CC ACC ATG G Linker 1: GGATCTATCCTCTTATCTCTCAA Linker 2: ATCTCTCAAACTCTCTGAACCTT Linker 3: TTCCCCTAACCCTAGCAG Linker 4: ATCATCCTCACCTCAAAACCCACC Linker 5: AGCCTCTCATCATCCTCACCTCAA

| L2 | AUCUCUCAAACUCUCUCGAACCUU |
|---|---|
| L2C | AUCUCUCAAACUCUCU |
| L2R | ACUCUCUCGAACCUU |

| L2 | A | TCT | CTC | AAA | CTC | TCT | CGA | ACC | TT |
|---|---|---|---|---|---|---|---|---|---|
| SCAN1 | a | AGA | ctc | aaa | ctc | tct | cga | acc | tt |
| SCAN2 | a | tct | GAG | aaa | ctc | tct | cga | acc | tt |
| SCAN3 | a | tct | ctc | GGG | ctc | tct | cga | acc | tt |
| SCAN4 | a | tct | ctc | aaa | GAG | tct | cga | acc | tt |
| SCAN5 | a | tct | ctc | aaa | ctc | AGA | cga | acc | tt |
| SCAN6 | a | tct | ctc | aaa | ctc | tct | GCT | acc | tt |
| SCAN7 | a | tct | ctc | aaa | ctc | tct | cga | GAG | tt |

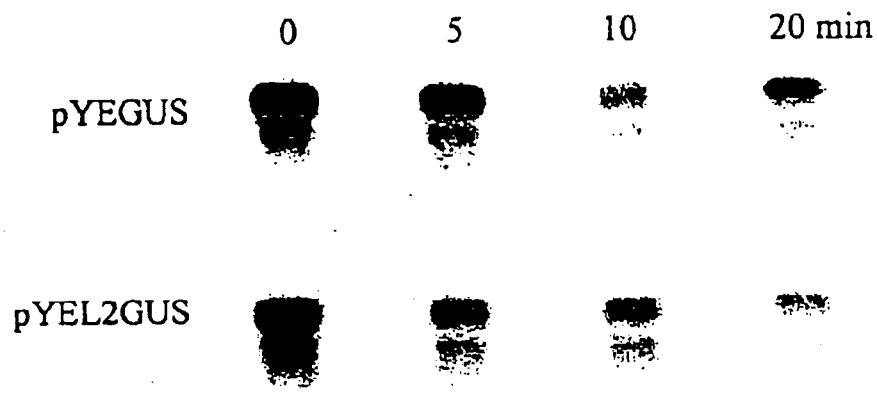
FIGURE 6P.1

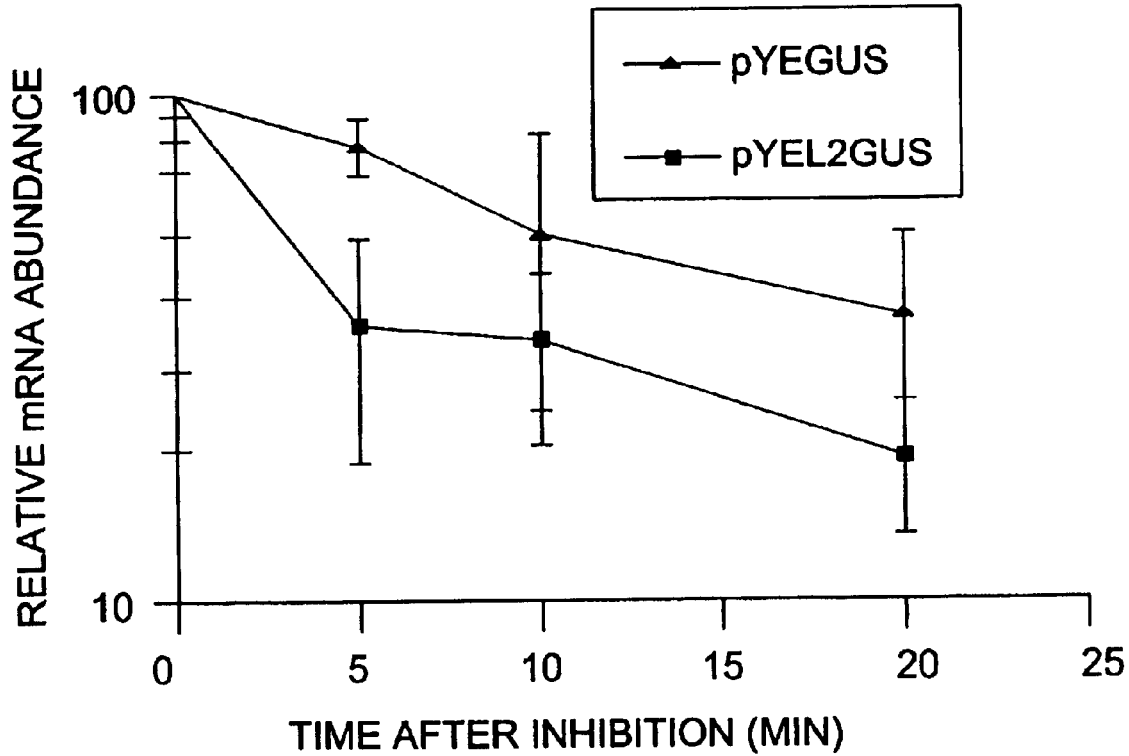
FIG. 6P.2

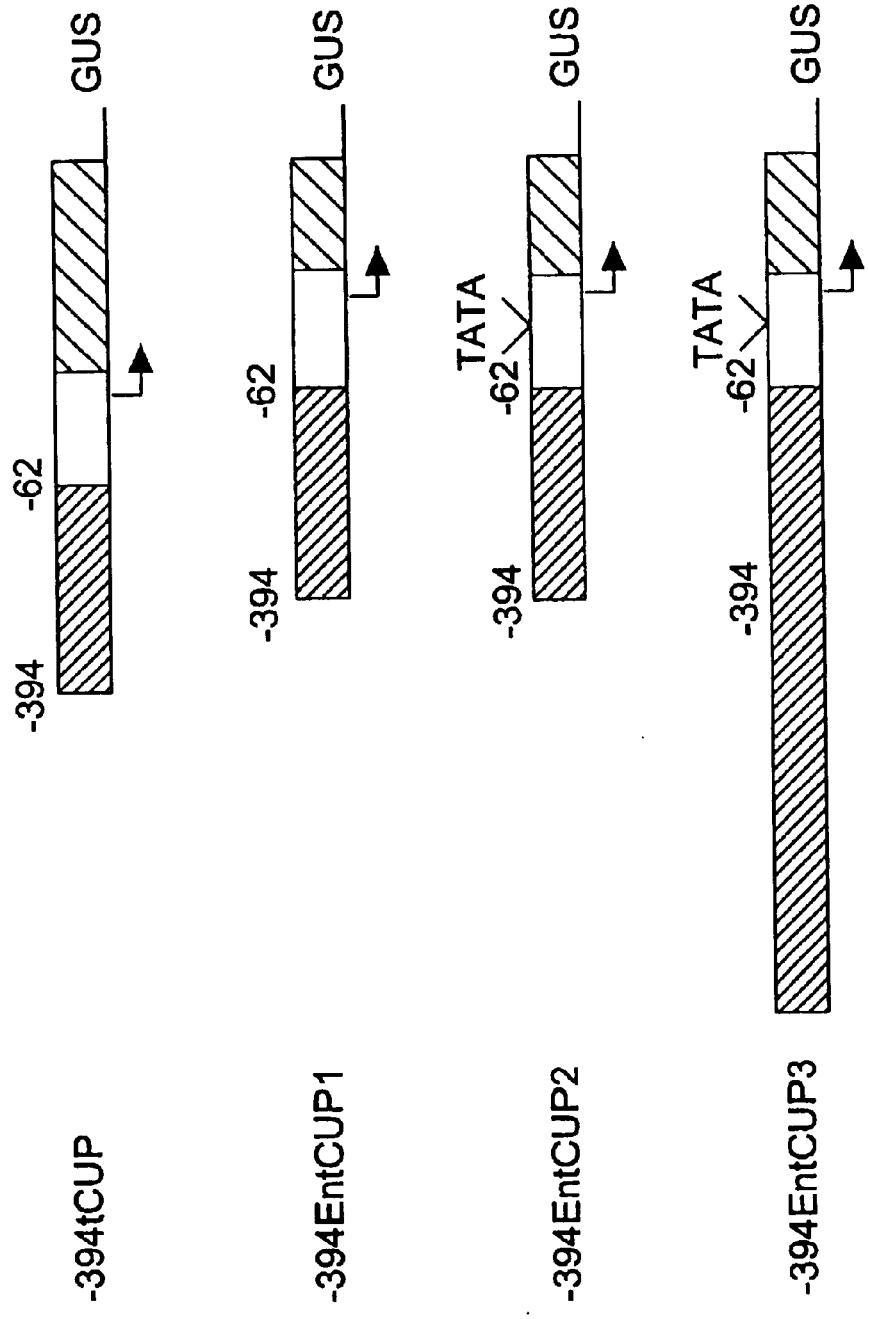
FIG. 7A.1

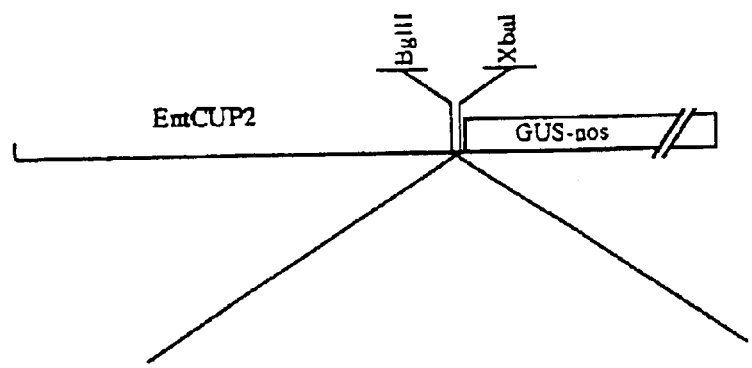

| | |
|---|---|
| pUCtCUP2(-N)GUS | (no sequence) |
| pUCtCUP2L1GUS | GGATCTATCCTCTTATCTCTCAA |
| pUCtCUP2L2GUS | ATCTCTCAAACTCTCTCGAACCTT |
| pUCtCUP2L3GUS | TTCCCCTAACCCTAGCAG |
| pUCtCUP2L4GUS | ATCATCCTCACCTCAAAACCCACC |
| pUCtCUP2L5GUS | AGCCTCTCATCATCCTCACCTCAA |
| pUCtCUP2SCAN3GUS | ATCTCTCGGGCTCTCTCGAACCTT |
| pUCtCUP2SCAN7GUS | ATCTCTCAAACTCTCTCGAGAGTT |
| pUCtCUP2-2XL2GUS | ATCTCTCAAACTCTCTCGAACCTTTCTCTCAAACTCTCTCGAACCTT |

FIGURE 7A.2

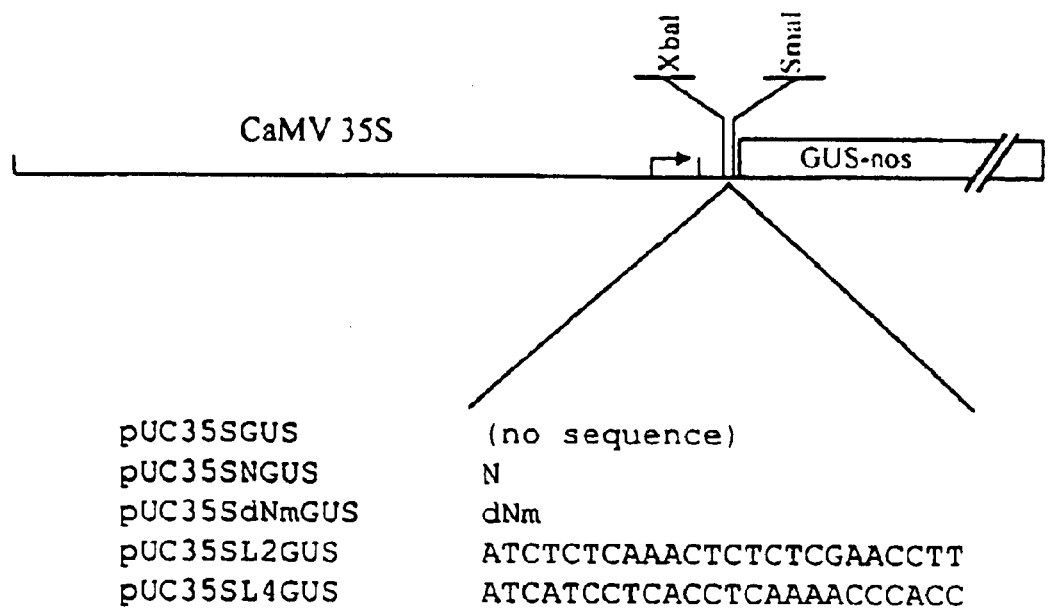
| | |
|---|---|
| pUC35SGUS | (no sequence) |
| pUC35SNGUS | N |
| pUC35SdNmGUS | dNm |
| pUC35SL2GUS | ATCTCTCAAACTCTCTCGAACCTT |
| pUC35SL4GUS | ATCATCCTCACCTCAAAACCCACC |
LEGEND:
— Vector sequence
▭ GUS reporter gene
↳ Start of transcription

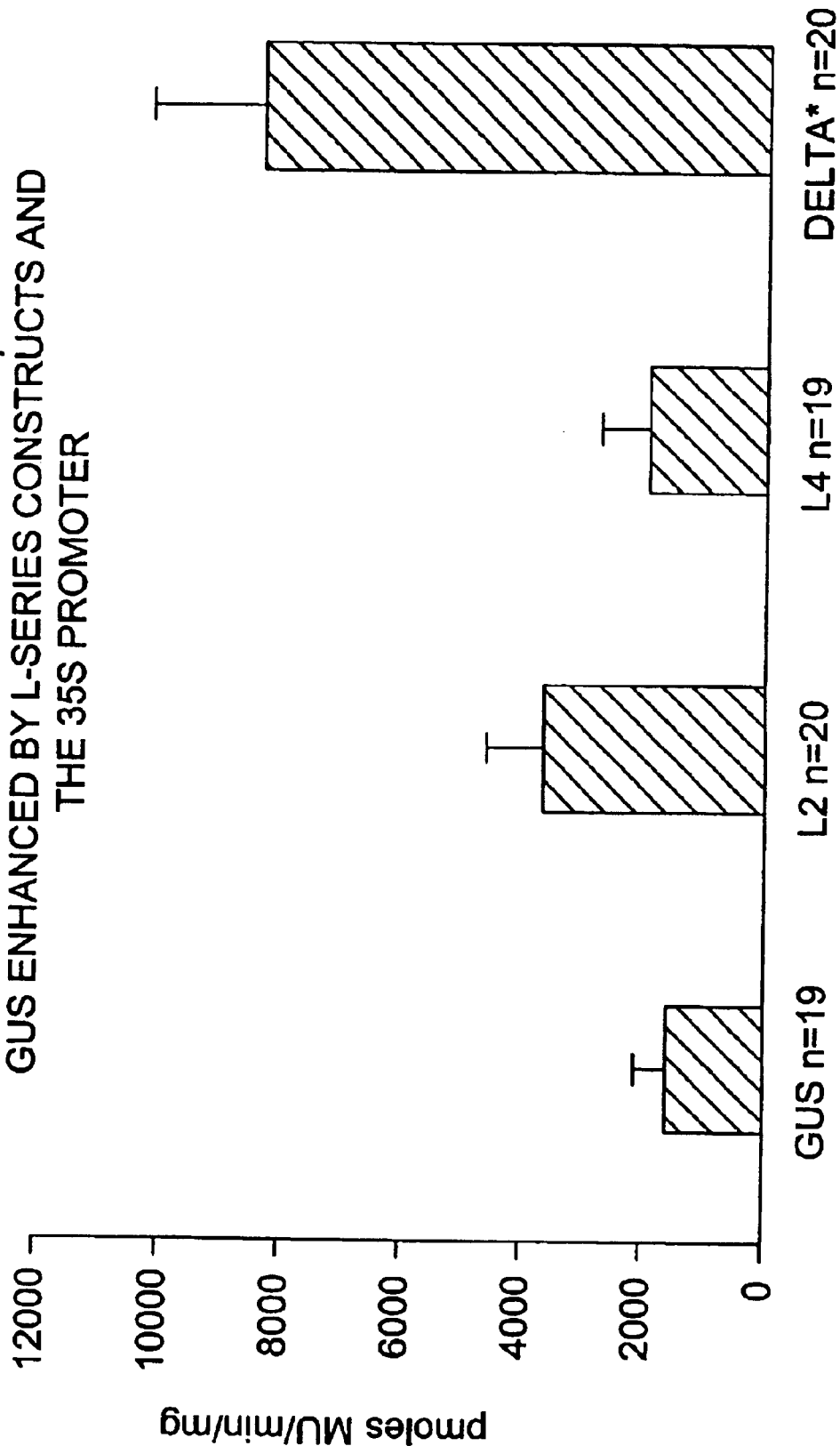

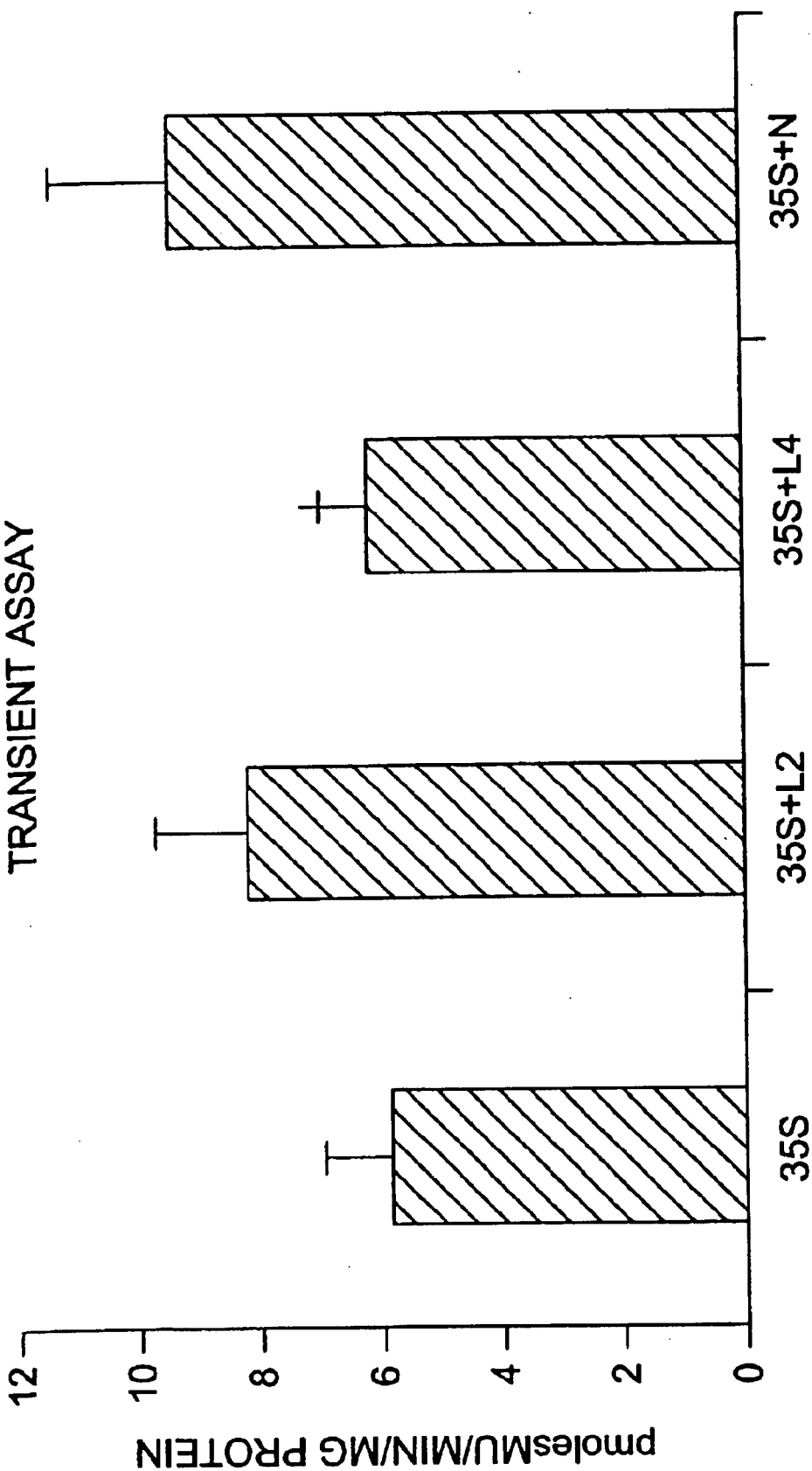

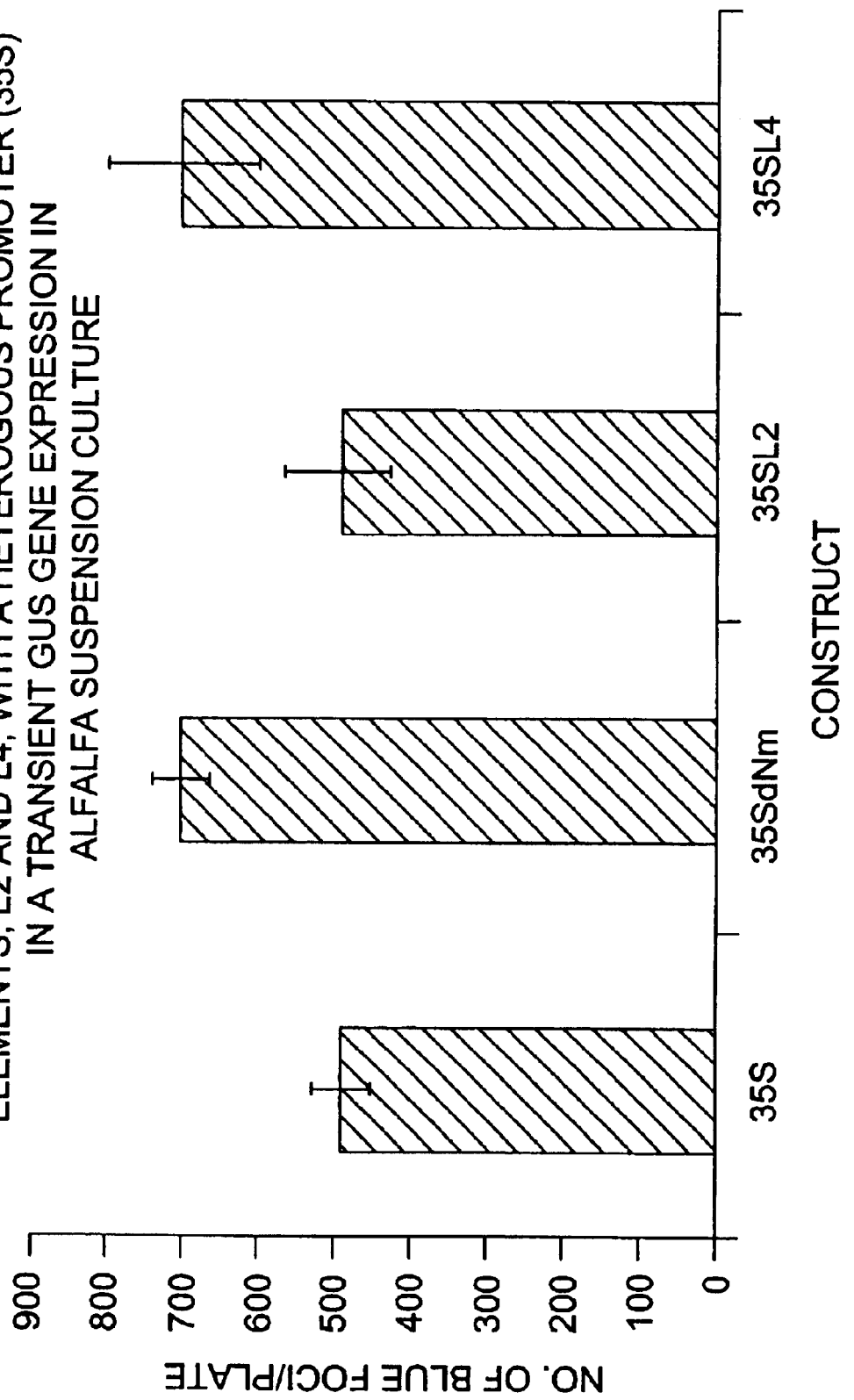

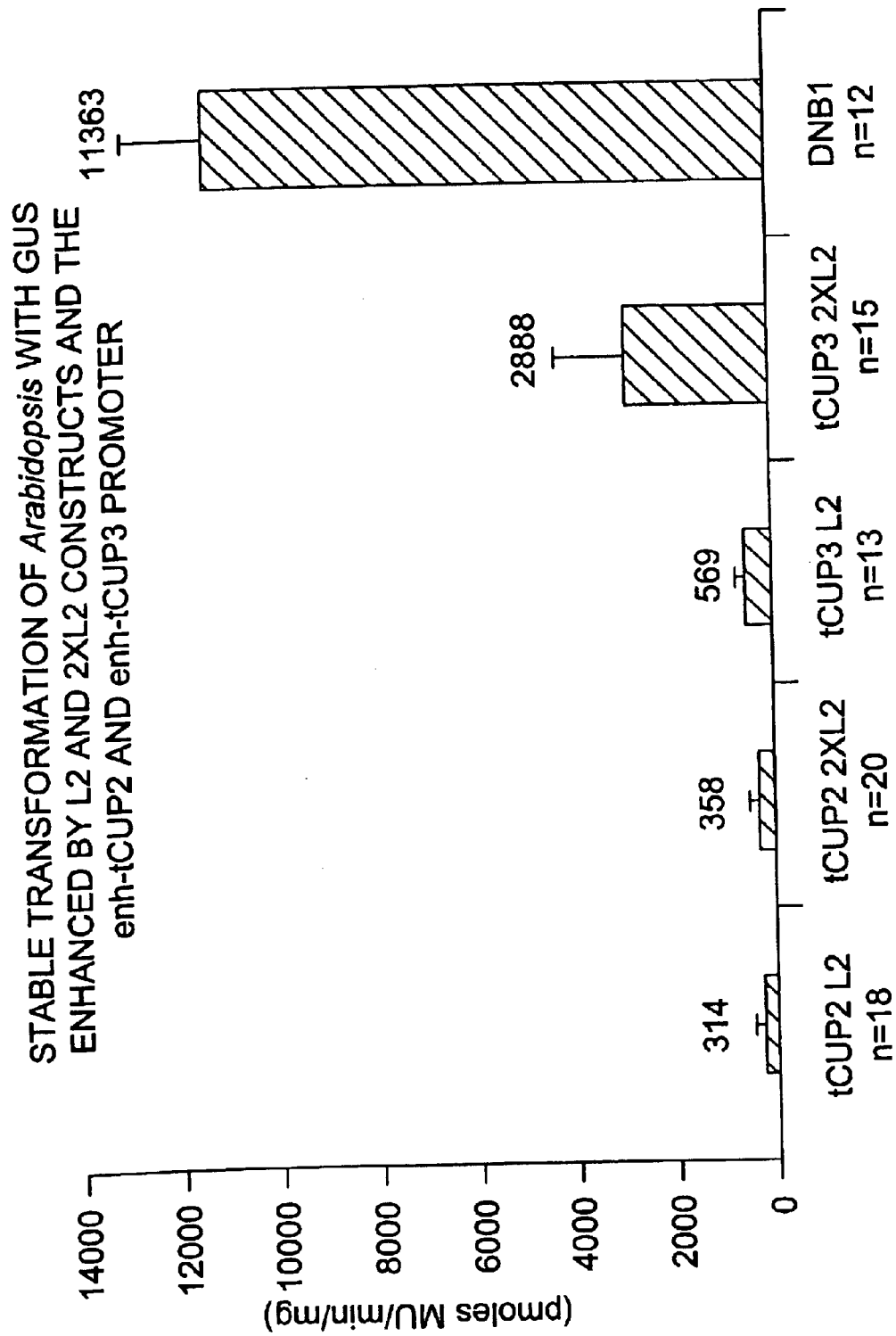

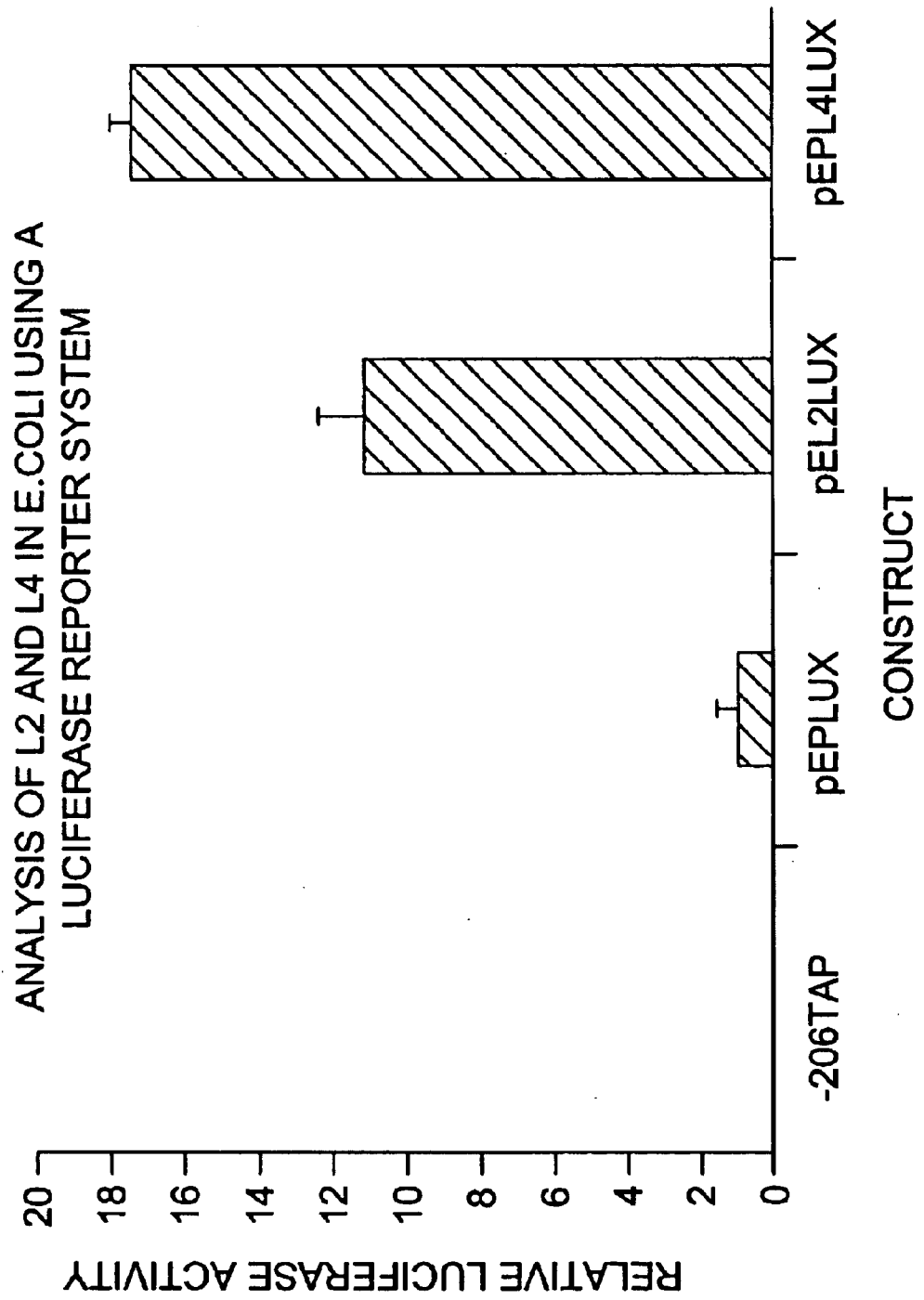

SEQUENCE LISTING

<160> NUMBER OF SEQ ID NOS: 33

<210> SEQ ID NO 1
<211> LENGTH: 2224
<212> TYPE: DNA
<213> ORGANISM: Nicotiana tabacum

<400> SEQUENCE: 1

```
tctagactta cagaaagtct ctaacacgtg agggaatgat ccctttcctt acctccctgt      60
agagatattg gcttttcaac aactagtaca taaatatgcg actttgaccg tgtatcccca     120
gtcaaaaggg aacttcaccc tcctagttct ttatttccaa catacatggg gagtaatgct     180
aaatttacat agaagaataa taaaatgaac tgtaactaat gatgtactgt tccaaagaga     240
tgaggacgtc aacatattta ttccttcagc cctttcaga ataataccat aagtagaaga      300
aatggcacat aaaatgaagt cctcggcaag tcaaatgtaa atctgaaccc acccagctaa     360
cccagtgaac tcaactttcc tggatagatc agcactcctt catgacattg catgccttct     420
```

-continued

```
ctttaaagag ccgcttgatc tctgaaaacc aaatgaatct ccacagagag atttcgagct      480
ccatgagacg cctttggtt cttgatttac taaacctata aaaatgaaag gaagtaggac      540
aactgcattt tgccgcttaa gatgcttcgg cgctttgtga attttaagtc atgagaaagt      600
acaatgttgg aatctcacat tagaacaatg tatttgtaat aacctaggaa agcaaagcta      660
gaagggaggt gcagctaaat cttcttctac cttgttatcc ttgcatttct tgaggaggag      720
gaactgtcct cgcaggtgca aaatctgcag tcgcccaaaa ggatattcag aagtatatta      780
caacatgttt aatggttaac caagtgaaag atcaaaatag tcattagaac aaaatgcgtg      840
ctcagagcgt atctactagt tcatcaaccc agtacacatc tctgaatttc atctcttgcc      900
gttgaactaa gtcaattggt caaagacgca taacatgaga gacactcata aaacggctga      960
ataacatgca gaagacgtca tgcgccttag gtctcattat gcatgagatt attagttata     1020
tgctccttca gtttgactag aaatgaaaaa tcagttaagc ctgtaacgaa atgataacct     1080
gcttcaagaa gattagacta tttttcataa aatatgcagt gccgtgaaat agatacttaa     1140
tcttaggcag gaaaaatctt ctattgggcc ataataagaa ctaccaatta gaaaggaggt     1200
agaaagctcc gatactgtta tgaaggccat tctaagtgct gatgtgaatt cccaataca     1260 aaatgacaac aaaaacaaaa gcctcaatcc taagctagtt ggggtcgcta tataaatcct     1320
cgacatccat ttaactccac ttggactcct ttctttccaa tattttaata ttgttagatt     1380
aatcataaaa ttgcttagct ttctactggc acttaaccta ctgcaaccct cctcttctgg     1440
gattccaaca caaacaacta agaggaattt gaaaaaaaga aagcaaatgt gagaagagac     1500
aaaatgtaca atgataccctc ttcttgcagc aaaggaggca ggttctctgc tgagacaagg     1560
ttctctattt cctgcaagac cttcgtatct tttattcgag accatgtatg tggaggtaac     1620
gccagcaata gtgctgtcag cacatcgttg cttgcagggg atcttctgca agcatctcta     1680
tttcctgaag gtctaacctc gaagatttaa gatttaatta cgtttataat tacaaaattg     1740
attctagtat ctttaattta atgcttatac attattaatt aatttagtac tttcaatttg     1800
ttttcagaaa ttatttact atttttata aaataaaagg gagaaaatgg ctatttaaat     1860
actagcctat tttatttcaa ttttagctta aaatcagccc caattagccc caatttcaaa     1920
ttcaaatggt ccagcccaat tcctaaataa cccaccccta acccgcccgg tttcccttt      1980 tgatccaggc cgttgatcat tttgatcaac gcccagaatt tcccctttc ctttttaat      2040 tcccaaacac ccctaactct atcccatttc tcaccaaccg ccacatatga atcctcttat     2100
ctctcaaact ctctcgaacc ttcccctaac cctagcagcc tctcatcatc ctcacctcaa     2160
aacccaccgg aatacatggc ttctcaagcc gtggaaacct tatactcacc tcccttgct     2220 ctta                                                                 2224
```

<210> SEQ ID NO 2
<211> LENGTH: 188
<212> TYPE: DNA
<213> ORGANISM: NdeI-SmaIfragment of tCUP (T1275)

<400> SEQUENCE: 2

```
catatgaatc ctcttatctc tcaaactctc tcgaaccttc ccctaaccct agcagcctct       60
catcatcctc acctcaaaac ccaccggaat acatggcttc tcaagccgtg aaaccttat      120 actcacctcc ctttgctctt acagtactcg gccgtcgacc gcggtacccg ggtggtcagt      180
cccttatg                                                              188
```

```
<210> SEQ ID NO 3
<211> LENGTH: 129
<212> TYPE: DNA
<213> ORGANISM: delta N with Kozak sequence

<400> SEQUENCE: 3
agatctatcc tcttatctct caaactctct cgaaccttcc cctaaccctc gcagcctctc      60
atcatcctca cctcaaaacc caccggccac catggcctct agaggacccc gggtggtcag     120
tcccttatg                                                             129

<210> SEQ ID NO 4
<211> LENGTH: 119
<212> TYPE: DNA
<213> ORGANISM: deltaN without Kozak sequence

<400> SEQUENCE: 4
agatctatcc tcttatctct caaactctct cgaaccttcc cctaaccctc gcagcctctc      60
atcatcctca cctcaaaacc caccggtcta gaggatcccc gggtggtcag tcccttatg     119

<210> SEQ ID NO 5
<211> LENGTH: 23
<212> TYPE: DNA
<213> ORGANISM: Linker 1

<400> SEQUENCE: 5
ggatctatcc tcttatctct caa                                             23

<210> SEQ ID NO 6
<211> LENGTH: 24
<212> TYPE: DNA
<213> ORGANISM: Linker 2

<400> SEQUENCE: 6
atctctcaaa ctctctcgaa cctt                                            24

<210> SEQ ID NO 7
<211> LENGTH: 18
<212> TYPE: DNA
<213> ORGANISM: Linker 3

<400> SEQUENCE: 7
ttcccctaac cctagcag                                                   18

<210> SEQ ID NO 8
<211> LENGTH: 24
<212> TYPE: DNA
<213> ORGANISM: Linker 4

<400> SEQUENCE: 8
atcatcctca cctcaaaacc cacc                                            24

<210> SEQ ID NO 9
<211> LENGTH: 24
<212> TYPE: DNA
<213> ORGANISM: Linker 5

<400> SEQUENCE: 9
agcctctcat catcctcacc tcaa                                            24

<210> SEQ ID NO 10
<211> LENGTH: 602
<212> TYPE: DNA
```

<213> ORGANISM: Nicotiana tabacum, rent 1
<220> FEATURE:
<221> NAME/KEY: misc_feature
<222> LOCATION: (1)..(602)
<223> OTHER INFORMATION: where n is a or t or g or c

<400> SEQUENCE: 10

| | | | | |
|---|---|---|---|---|
| aattgtaagc | gggataacaa | tttcacacag | gaaacagcta | tgaccatgat | tacgccaagc | 60 |
| ttttaatacg | actcactata | gggaaagctt | ataattacaa | aattgattct | agtattttta | 120 |
| atttaatatt | tttacattat | taattaattt | agaagtttta | attttttttc | agaaatcatt | 180 |
| ttactatttt | tataaaaaca | aaagggaaaa | gtggttattt | aaatactagc | cctatttcat | 240 |
| ttcaattata | gcctaaaatc | agccccaatt | aaccccaatt | ccaaattcaa | acgggccagc | 300 |
| ccaattccta | aaatgacccg | ctcctaaccc | gcttttccaa | cccgcccggt | ttcccctttt | 360 |
| gatccaggct | gttgatcatt | ttgatcaacg | gccagaattt | cccctttcct | ttttaattcc | 420 |
| caaacacccc | ccaaccttat | cccgtttctc | accaaccgcc | agatctatcc | tcttatctct | 480 |
| caaactctct | cgaaccttcc | cctaacccta | gcagcctctc | atcatcctca | cctcaaaacc | 540 |
| caccggccac | catggcctct | agaggatccc | cgggtggtca | gtcccttatg | ttacgtcctn | 600 |
| aa | | | | | | 602 |

<210> SEQ ID NO 11
<211> LENGTH: 610
<212> TYPE: DNA
<213> ORGANISM: Nicotiana tabacum,RENT 2

<400> SEQUENCE: 11

| | | | | | | |
|---|---|---|---|---|---|---|
| atgttgtgtg | gaattgtgag | cgggataaca | atttcacaca | ggaaacagct | atgaccatga | 60 |
| ttacgccaag | ctctaatacg | actcactata | gggaaagctt | ataattacaa | aattgattct | 120 |
| agtattttta | atttaatatt | tatacattat | taattaactt | agtactttca | attcgttttc | 180 |
| aaaaattatt | ttactatttt | ttgtaaaata | aaagggagaa | aatggctatt | taaatactag | 240 |
| ccctatttta | tttcaatttt | agcctaaaat | cagccccaa | ttaaccccaa | tttcaaattc | 300 |
| aaatgggaca | gcccaattcc | taaaataacc | cgccctaac | cctcttatcc | aacccacccg | 360 |
| atttccccctt | tgatccagg | ttgttgatca | ttttgatcaa | cgaccagaat | tccccccttc | 420 |
| ctgttttttaa | ttcccaaaca | ccccccaacc | ctatcccatt | tctcaccaac | cgccagatct | 480 |
| atcctcttat | ctctcaaact | ctctcgaacc | ttcccctaac | cctagcagcc | tctcatcatc | 540 |
| ctcacctcaa | aacccaccgg | ccaccatggc | ctctagagga | tccccgggtg | gtcagtccct | 600 |
| tatgtgcgtc | | | | | | 610 |

<210> SEQ ID NO 12
<211> LENGTH: 507
<212> TYPE: DNA
<213> ORGANISM: Nicotiana tabacum,RENT 3
<220> FEATURE:
<221> NAME/KEY: misc_feature
<222> LOCATION: (1)..(507)
<223> OTHER INFORMATION: where n is a or t or g or c

<400> SEQUENCE: 12

| | | | | | | |
|---|---|---|---|---|---|---|
| ttgattctag | ttttttttaat | ttaatattta | tacattatta | attaatttag | ttcttttcaat | 60 |
| ttgttttcag | aaattatttt | actattttt | ataaaataaa | agggagaaaa | tggctattta | 120 |
| aataccagcc | ctattttatt | tcaatttaa | cctaaaatca | gccccagtta | gcccaaacg | 180 |
| gcccatccca | attcctaaaa | taactcgccc | ctaacccgct | tatccaaccc | gcccggttcc | 240 |

```
ccttttgatc caggccgttg atcattttga tcaacgacca gaatttcccc tttccttttt      300
taattcccaa acaccgccaa acctatccca tttctcacca accgccagat ctatcctctt      360
atctctcaaa ctctctcgaa ccttccccta accctagcag cctctcatca tcctcacctc      420
aaaacccacc ggccaccatg gcctctagag gatccccggg tggtcagtcc cttatgtnac      480
gncctaaatg nccgncctgn nnnnnnc                                          507

<210> SEQ ID NO 13
<211> LENGTH: 599
<212> TYPE: DNA
<213> ORGANISM: Nicotiana tabacum,RENT 5
<220> FEATURE:
<221> NAME/KEY: misc_feature
<222> LOCATION: (1)..(599)
<223> OTHER INFORMATION: where n is a or t or g or c

<400> SEQUENCE: 13
ggaattgtga gcggataaca atttcacaca ggaaacagct atgaccatga ttacgccaag       60
ctctaatang actcactata gggaaagctt ataattacaa atttgattct agtatttta      120 atttaatatt tatacattat taattaattt agtactttca atttgttttc agaaatcatt     180
ttactatggt ttataaaata aagggagaa atggctatt taaatactag ccctatttta       240 tttcaattt agcctaaaat cagccccaat taacccctat ttcaaattca acgggctag       300 cccagttcct aaaataaccc tccctaacc cgcttatcca acccgccctg tttcccttt       360 tgatccaggc cgttgatcat tttgatcaac gaccaaaatt tccccttcc tttttaatt      420 cccaaacacc cccaaccctc tcccattctc caccaaccgc cagatctatc ctcttatctc     480
tcaaactctc tcgaaccttc cctaaccct agcagcctct catcatcctc acctcaaaac     540
ccaccggcca ccatggcctc tagaggatcc ccgggtggtc agtcccttat gttacgtcc     599

<210> SEQ ID NO 14
<211> LENGTH: 616
<212> TYPE: DNA
<213> ORGANISM: Nicotiana tabacum,RENT 7
<220> FEATURE:
<221> NAME/KEY: misc_feature
<222> LOCATION: (1)..(616)
<223> OTHER INFORMATION: where n is a or t or g or c

<400> SEQUENCE: 14
tttatgcttc cggctcgtat gttgtgtgga attgtgagcg gataacaatt tcacacagga       60
aacagctatg accatgatta cgccaagctc taatacgact cactataggg aaagcttata      120
attacaaaat tgattatagt acttttaatt taatatttat acattattaa ttaatttagc      180
actttcaatt tattttcaga aaccatttta ctatttttta taaataaaa gggacaaaat      240 ggctatttaa ataccaacac tattttattt caatttagc ctaaaatcaa acccaattaa       300
ccccaaacgg gccagcccaa ttcctaaaac aacccgcccc taacccgctt atccaacccg      360
cccgatttcc tcttttgatc caggccgttg atcattttga tcaacggcca gaatttcccc      420
tttccttttt tcattcccaa acaccccaa acctatccca tttctcacca accgccagat      480
ctatcctctt atctctcaaa ctctctcgaa ccttcccta accctagcag cctctcatca      540
tcctcacctc aaaacccacc ggccaccatg gcctctagag gatccccggg tggtcagtcc      600
cttatgttac gtcctn                                                      616
```

-continued

```
<210> SEQ ID NO 15
<211> LENGTH: 24
<212> TYPE: DNA
<213> ORGANISM: SCAN 1

<400> SEQUENCE: 15
aagactcaaa ctctctcgaa cctt                                            24

<210> SEQ ID NO 16
<211> LENGTH: 24
<212> TYPE: DNA
<213> ORGANISM: SCAN 2

<400> SEQUENCE: 16
atctgagaaa ctctctcgaa cctt                                            24

<210> SEQ ID NO 17
<211> LENGTH: 24
<212> TYPE: DNA
<213> ORGANISM: SCAN 3

<400> SEQUENCE: 17
atctctcggg ctctctcgaa cctt                                            24

<210> SEQ ID NO 18
<211> LENGTH: 24
<212> TYPE: DNA
<213> ORGANISM: SCAN 4

<400> SEQUENCE: 18
atctctcaaa gagtctcgaa cctt                                            24

<210> SEQ ID NO 19
<211> LENGTH: 24
<212> TYPE: DNA
<213> ORGANISM: SCAN 5

<400> SEQUENCE: 19
atctctcaaa ctcagacgaa cctt                                            24

<210> SEQ ID NO 20
<211> LENGTH: 24
<212> TYPE: DNA
<213> ORGANISM: SCAN 6

<400> SEQUENCE: 20
atctctcaaa ctctctgcta cctt                                            24

<210> SEQ ID NO 21
<211> LENGTH: 24
<212> TYPE: DNA
<213> ORGANISM: SCAN 7

<400> SEQUENCE: 21
atctctcaaa ctctctcgag agtt                                            24

<210> SEQ ID NO 22
<211> LENGTH: 47
<212> TYPE: DNA
<213> ORGANISM: 2xL2

<400> SEQUENCE: 22
atctctcaaa ctctctcgaa cctttctctc aaactctctc gaacctt                   47
```

-continued

```
<210> SEQ ID NO 23
<211> LENGTH: 23
<212> TYPE: DNA
<213> ORGANISM: B1-L2

<400> SEQUENCE: 23
atctctcaaa ctatctgaaa ctt                                            23

<210> SEQ ID NO 24
<211> LENGTH: 24
<212> TYPE: DNA
<213> ORGANISM: B7-L2

<400> SEQUENCE: 24
atctctcaaa ctctctcaaa cttt                                           24

<210> SEQ ID NO 25
<211> LENGTH: 21
<212> TYPE: DNA
<213> ORGANISM: L2D1

<400> SEQUENCE: 25
atctctcctc tctcaaactt t                                              21

<210> SEQ ID NO 26
<211> LENGTH: 21
<212> TYPE: DNA
<213> ORGANISM: L2D2

<400> SEQUENCE: 26
atctctcaaa ctctctcgat t                                              21

<210> SEQ ID NO 27
<211> LENGTH: 18
<212> TYPE: DNA
<213> ORGANISM: L2D3

<400> SEQUENCE: 27
atctctcctc tctcgatt                                                  18

Figure 6N:
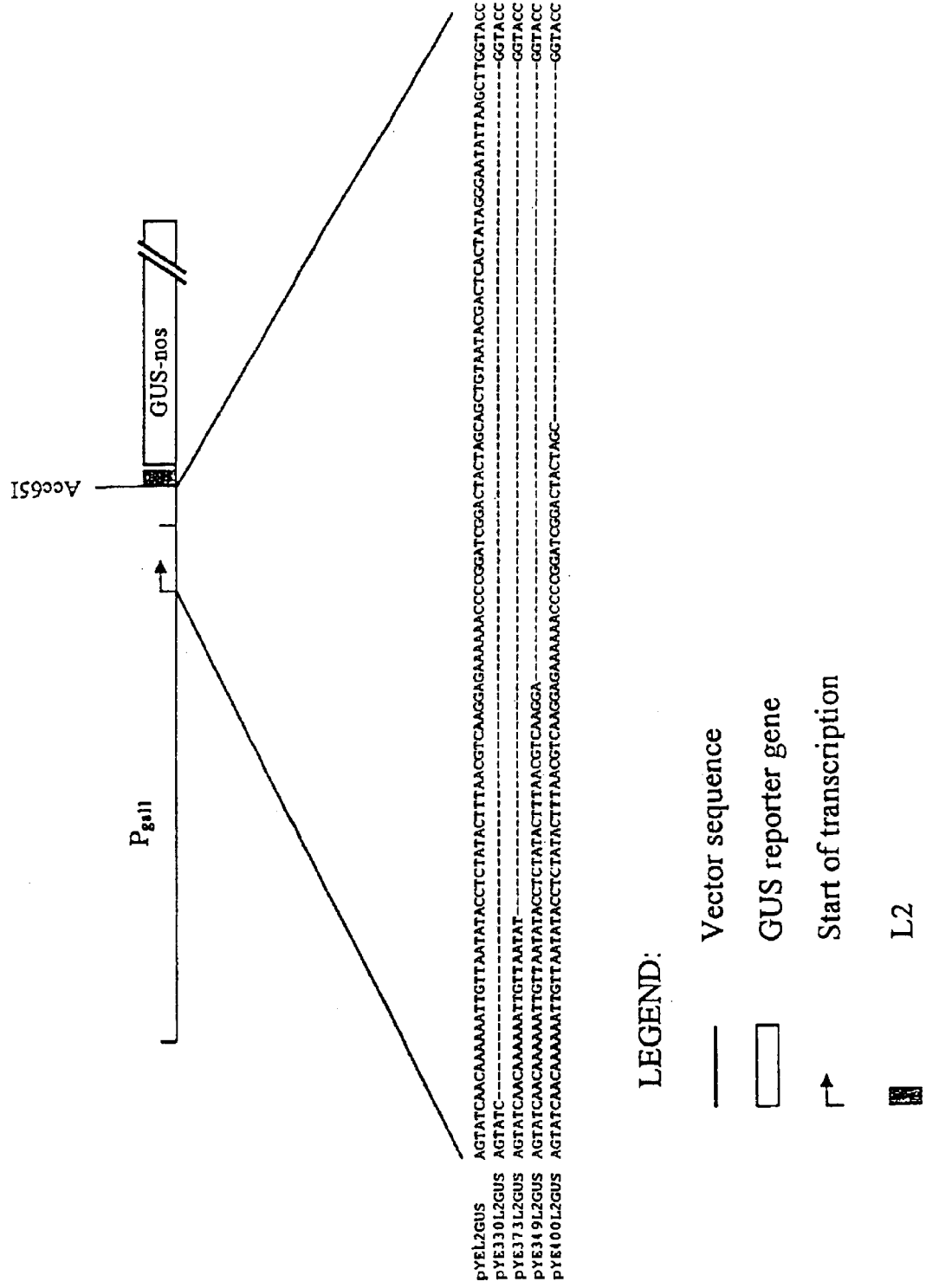
Figure 60:
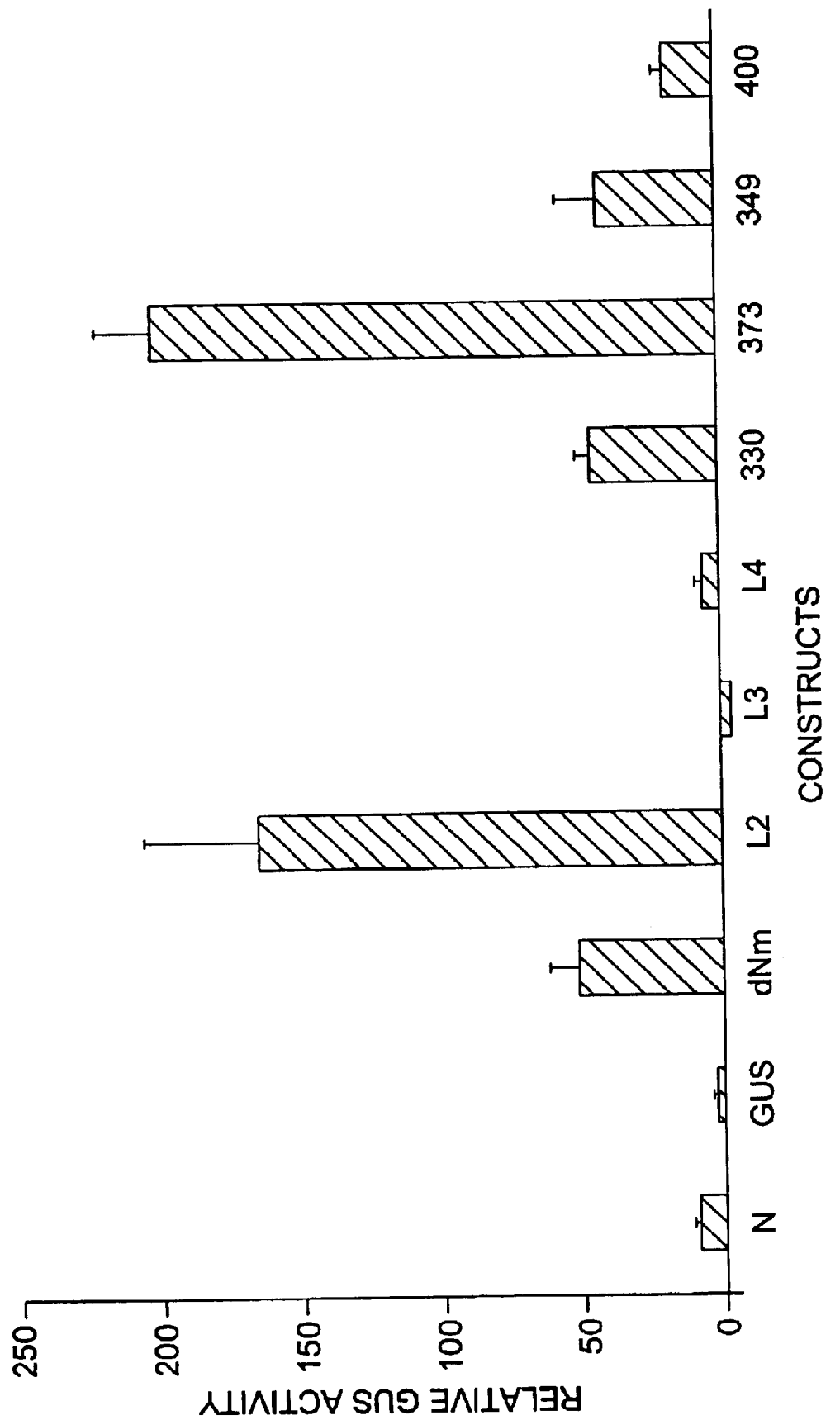

<210> SEQ ID NO 28
<211> LENGTH: 118
<212> TYPE: DNA
<213> ORGANISM: pyel2gus (figure 6N)

<400> SEQUENCE: 28
agtatcaaca aaaaattgtt aatataccct atactttaac gtcaaggaga aaaaaccccg    60
gatcggacta ctagcagctg taatacgact cactataggg aatattaagc ttggtatc    118

<210> SEQ ID NO 29
<211> LENGTH: 12
<212> TYPE: DNA
<213> ORGANISM: pye330l2gus

<400> SEQUENCE: 29
agtatcggta cc                                                        12

<210> SEQ ID NO 30
<211> LENGTH: 31
<212> TYPE: DNA
<213> ORGANISM: pye373l2gus
```

```
<400> SEQUENCE: 30
agtatcaaca aaaaattgtt aatatggtac c                              31

<210> SEQ ID NO 31
<211> LENGTH: 55
<212> TYPE: DNA
<213> ORGANISM: pye34912gus

<400> SEQUENCE: 31
agtatcaaca aaaaattgtt aatatacctc tatactttaa cgtcaaggag gtacc    55

<210> SEQ ID NO 32
<211> LENGTH: 82
<212> TYPE: DNA
<213> ORGANISM: pye40012gus

<400> SEQUENCE: 32
agtatcaaca aaaaattgtt aatatacctc tatactttaa cgtcaaggag aaaaaacccc  60
ggatcggact actagcggta cc                                       82

<210> SEQ ID NO 33
<211> LENGTH: 525
<212> TYPE: DNA
<213> ORGANISM: tcup-rent

<400> SEQUENCE: 33
tacaaaattg attctagtat ctttaattta atgcttatac attattaatt aatttagtac  60
tttcaatttg ttttcagaaa ttattttact atttttttata aaataaaagg gagaaaatgg 120
ctatttaaat actagcctat tttatttcaa ttttagctta aaatcagccc caattagccc  180
caatttcaaa ttcaaatggt ccagcccaat tcctaaataa cccacccta acccgcccgg   240 tttcccctttt tgatccaggc cgttgatcat tttgatcaac gcccagaatt tcccctttttc 300 cttttttaat tcccaaacac ccctaactct atcccatttc tcaccaaccg ccacatatga  360
atcctcttat ctctcaaact ctctcgaacc ttcccctaac cctagcagcc tctcatcatc  420
ctcacctcaa aacccaccgg aatacatggc ttctcaagcc gtggaaacct tatactcacc  480
tccctttgct cttacagtac tcggccgtcg accgcggtac ccggg               525
```

TRANSLATIONAL REGULATORY ELEMENTS

This Appln claims benefit of Ser. No. 60/172,813 Dec. 21, 1999

The present invention relates to regulatory elements capable of mediating the translational efficiency of a transcript linked in operative association therewith. The translational regulatory elements of the present invention may also be used in combination with other regulatory elements, such as promoters, enhancers, or fragments thereof, to modify the levels of expression of a gene of interest within a host

BACKGROUND OF THE INVENTION

Regulatory elements within the 5' and 3' untranslated regions (UTR) of genes are known to mediate transcriptional and translational efficiencies of associated promoters and transcripts, respectively. These regulatory elements can modulate gene expression in an organism through a number of mechanisms including transcription, translation, and RNA stability. For example, some 5' non-translated regions (5' leaders) are known to enhance the translational efficiency of mRNA, resulting in an increased accumulation of recombinant protein many fold.

Some of these 5' leaders affect gene expression by quantitative enhancement of transcription, as with the UTR of the thylakoid protein genes PsaF, PerH and PetE from pea (Bolle et al., 199, Plant J. 6, 513–523), or by repression of transcription, as for the 5' UTR of the pollen-specific LAT59 gene from tomato (Curie and McCormick, 1997, Plant Cell 9, 2025–2036). Some 3' regulatory regions contain sequences that act as mRNA instability determinants, such as the DST element in the Small Auxin-Up RNA (SAUR) genes of soybean and Arabidopisis (Newman et al., 1993, Plant Cell 5, 701–714).

Other 5' leaders have been shown to contain translational enhancer sequences or structures such as the Omega sequence of the 5' leader of the tobacco mosaic virus (Gallie and Walbot, 1992, Nucleic Acid Res. 20, 4631–4638), the 5' alpha-beta leader of the potato virus X (Tomashevskaya et al, 1993, J. Gen. Virol. 74, 2717–2724), and the 5' leader of the photosystem I gene psaDb of *Nicotiana sylvestris* (Yamamoto et al., 1995, J. Biol. Chem 270, 12466–12470). In plants, most of the translation enhancers characterized belong to plant virus 5' leaders (Gallie, D. R., et al., 1987, NAR 15, 8693–8711.; Jobling and Gehrke, 1987, Nature 325, 622–625; Gehrke, 1989, U.S. Pat. No. 4,820,639.; Smimyagina, et al 1991, Biochimie 73: 998–1011; Wilson, 1996, U.S. Pat. No. 5,489,527). Heat shock genes have been shown to contain a sequence that enhances translation in their 5' non-translated leader in animals and plants (McGarry and Lindquist, 1985 Cell 42, 903–911; Austin, 1994 U.S. Pat. No. 5,362,865). Some other plant 5' non-translated leaders have also been shown to enhance translation under normal (Yamamoto et al, 1995) and specific stress conditions (Pitto et al, 1992, Plant Physiol. 100; 1827–1833; Bailey-Serres and Dawe, 1996, Plant Physiol. 112: 685–695). Other translational enhancers are also known in the literature (e.g. Helliwell and Gray 1995, Plant Mol. Bio. vol 29, pp. 621–626; Dickey L. F. al. 1998, Plant Cell vol 10, 475–484; Dunker B. P. et al. 1997 Mol. Gen. Genet. vol 254, pp. 291–296). These translational regulatory elements are directed to enhancing translational activities, and have relatively low efficiencies. Synthetic random sequences used as 5' non-translased leaders are considered to have a neutral effect on translation efficiency and are used as reference points for minimum translation in studies of translation enhancers (Datla et al, 1993,Plant Science 94:139–149; Bates et al. 1996, Plant. J. 10: 613–623).

The present invention is directed to translational regulatory elements that mediate the translation efficiency of a transcript in operative association therewith by enhancing or inhibiting translation efficiency. These translational regulatory elements are equally, or more, active than those of the prior art. The translational regulatory elements of the present invention may be used to mediate the translation efficiency of chimeric transcripts comprising one or more translational regulatory elements. Furthermore, the translational regulatory elements of the present invention may be used within chimeric constricts comprising other regulatory elements, for example, promoter, enhancer, silencer, or other elements, or a combination thereof.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to regulatory elements capable of mediating the translational efficiency of a transcript linked in operative association therewith. The translational regulatory elements of the present invention may also be used in combination with other regulatory elements, such as promoters, enhancers, or fragments thereof, to modify the levels of expression of a gene of interest within a host.

According to the present invention there is provided an isolated nucleic acid comprising the nucleotide sequence defined by SEQ ED NO:6, or a fragment, derivative or analog thereof, wherein said fragment, derivative or analog thereof exhibits translational regulatory activity. Also included within the present invention is a construct comprising, at least one isolated nucleic acid as just defined, in operative association with a gene of interest, and one or more regulatory elements required for the expression of the gene of interest within a host organism. Preferably, the one or more regulatory elements comprise a regulatory element selected from the group consisting of an inducible promoter, developmentally regulated promoter, tissue specific promoter, constitutive promoter, and enhancer element.

This invention also relates to a method of increasing the amount of protein produced in an organism comprising, transforming the organism with a construct as defined above, growing the organism, and obtaining the protein therefrom.

Furthermore, the present invention relates to an isolated nucleic acid comprising a nucleotide sequence selected from the group consisting of SEQ ID NO:5, 6, 7, 8, 9, and a fragment, derivative, analog or a combination of a fragment, derivative or analogue, of the nucleotide sequence selected from the group consisting of SEQ ID NO:5, 6, 7, 8 and 9, wherein the fragment, derivative analog, or combination thereof exhibits translational regulatory activity. The present invention also includes a construct comprising, at least one isolated nucleic acid as just defined, in operative association with a gene of interest, and one or more regulatory elements required for the expression of the gene of interest within a host organism. Preferably, the one or more regulatory elements comprise a regulatory element selected from the group consisting of an inducible promoter, developmentally regulated promoter, tissue specific promoter, constitutive promoter, and enhancer element.

The present invention also pertains to transgenic hosts comprising the constructs as defined above. The transgenic host are selected from the group consisting of a plant, tree, animal, insect, yeast and bacteria. Preferably, the transgenic host is a plant.

The present invention also embraces a method of mediating the translational activity of a transcript comprising, transforming a host with any one construct as defined above, and growing the host.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows the sequence similarity between several members of the RENT family of highly repetitive sequences. FIG. 1(C) shows the actual sequence alignments of FIG. 1 (A).

FIG. 2 (A) shows the levels of GUS expression in leaves from randomly selected plants containing either T1275-GUS-nos (left-handside) or35S-GUS-nos (light-hand side). FIG. 2 (C) shows a Western blot of GUS fusion protein obtained from T1275-GUS-nos and 35S-GUS-nos plants. Leaf extracts were equally loaded onto gels and GUS was detected using anti-GUS antibodies. The molecular weight markers are indicated on the right-hand side of the gel; untransformed control (SR1) and GUS produced in E. coli (Ec).

FIG. 3 (A) shows the level of accumulated GUS mRNA measured by RNase protection assay and densitometry of autoradiograms in leaves from the same randomly selected plants containing either T1275-GUS-nos, T1275-N-GUS-nos. FIG. 3 (B) shows the level of accumulated GUS mRNA measured by RNase protection for 35S-GUS-nos or 35S+N-GUS-nos. FIG. 3 (C) shows the ratio between GUS specific activity and mRNA levels in leaves of individual, regenerated, greenhouse-grown transgenic plants containing tCUP-GUS-nos, tCUP-N-GUS-nos, 35S-GUS-nos, or 35S+N-GUS-nos constructs.

FIG. 4 (B) shows T1275 (ΔN)-GUS-nos (also referred to as tCUPdelta-GUS-nos). "ΔN38 , (also referred to as "dN" or "deltaN") was created by changing the NdeI site "a" in the leader sequence of T1275-GUS-nos (FIG. 10(A)) to a BglII site "b" (see FIG. 10(B)) to eliminate the upstream ATG at nucleotides 2087–2089 of SEQ ID NO:2. A Kozak consensus sequence "c" was constructed at the initiator MET codon and a NcoI site was added. The transcriptional start site, determined for T1275, is indicated by the arrow.

FIG. 5 shows maps of the constructs used for transient expression in yeast, corn and white spruce.

shows the activity of constructs comprising "N", L2, L2C, L2R, and SCAN1 to SCAN7 within a yeast expression system. pYEGUS, pYENGUS, pYEL2GUS, pYEL2CGUS, pYEL2RGUS, as defined above; pYESCAN1GUS to pYESCAN7GUS, pYES2 with each of SCAN1 to SCAN7, respectively, and GUS. FIG. 6 (I) hows a graphic representation and nucleotide sequence of the fragments derived from $dN^m$ which have been tested in yeast. FIG. 6 (J) shows the activity within a yeast expression system of the constructs comprising deletions of the motifs AAA and ACC within L2, as shown in FIG. 6 (I). pYEGUS, pYEL2GUS, pYESCAN3GUS and pYESCAN7GUS, as defined above; pYEL2D1GUS, pYES2 with L2D1 and GUS; pYEL2D2GUS, pYES2 with L2D2 and GUS; pYFL2D3GUS, pYES2 with L2D3 and GUS. FIG. 6 (K) shows the activity within a yeast expression system of the constructs comprising L2 homologous from the RENT family, as shown in FIG. 6 (I). pYEGUS, pYEL2GUS, as defined above; pYEB1L2GUS, pYES2 with B1-L2 and GUS; pYEB7L2GUS, pYES2 with B7-L2 and GUS. FIG. 6 (L) shows the activity within a yeast expression system of the construct comprising a duplicated version of L2, as shown in FIG. 6 (I). pYEGUS, pYEL2GUS, as defined above; pYE2L2GUS, pYES2 with 2×L2 and GUS. FIG. 6 (M) shows the graphic representation and nucleotide sequence of constructs using the ADH1 promoter and tested in the yeast system (see FIG. 6 (H)). FIG. 6 (N) shows the graphic representation and nucleotide sequence of constructs where the position of L2 was varied in relation to the predicted start of transcription. The sequence between the start of transcription and L2 is shown. FIG. 6 (O) shows the activity within a yeast expression system of the constructs where L2 is located at varying position relative to the predicted transcription start, as shown in FIG. 6 (N). GUS, N, $dN^m$, L2, L3 and L4 are pYEGUS, pYENGUS, pYEdN$^m$GUS, and pYEL2GUS, pYEL3GUS, pYFL4GUS, as defined above; 330, pYES2 with 6 bases in front of the CAP site and prior to linker 2; 373, pYES2 with 25 bases in front of the CAP site and prior to linker 2; 349, pYES2 with 49 bases in front of the CAP site and prior to linker 2; 400, pYES2 with 76 bases in front of the CAP site and prior to linker 2. FIG. 6 (P) shows the stability of the GUS mRNA from pYEGUS and pYEL2GUS in the yeast expression system. FIG. 6(P).2 shows the mean value of three experiments as the one shown in FIG. 6(P).1. The Northern results were quantified and normalised for rRNA content. For each experiment, the amount of GUS RNA present in time=0 samples was arbitrarily attributed the value of 100 and RNA at other time points were calculated in relation to his value.

FIG. 7 shows the relative activity of several constructs within a variety of plant systems. FIG. 7(A) shows a graphic representation and nucleotide sequence of several fragments and derivatives of $dN^m$ in association with the promoter EntCUP2 (also referred to as tCUP2).

FIG. 8 (E) shows the relative activity of constructs within an alfalfa transient assay using a cell suspension culture. The activity of the constructs in the bombarded cell layer is expressed as the number of blue foci per plate. 35SL2 and 35SL4 comprises 35S linked with L2 and GUS (35S-L2-GUS-nos), or L4 and GUS (35S-L4-GUS-nos), respectively; 35SdN$^m$ comprises 35S linked with $dN^m$ (35SdN$^m$-GUS-nos); 35S comprises 35S linked directly to GUS (35S-GUS-nos). FIG. 8 (F) shows the relative activity of constructs within a corn transient assay using a callus culture derived from maize embryos. Activity is expressed as the number of blue foci per plate (n is the number of plates counted). Asterisks above the graph bars indicate the intensity of the foci. Calli were submitted to an overnight histological staining assay, two days after bombardment. 35SL2 and 35SL4 comprises 35S linked with L2 and GUS (35S-L2-GUS-nos), or L4 and GUS (35S-L4-GUS-nos), respectively; 35Sdelta* comprises 35S linked with the dN$^m$ (35SdN$^m$-GUS-nos); 35S comprises 35S linked directly to GUS (35S-GUS-nos). FIG. 8 (G) shows the relative activity of tCUP leader elements in a transient expression system in white spruce callus. Activity is expressed as the number of blue foci per plate. 35SL2 and 35SL4 comprises 35S linked with L2 (35S-L2-GUS-nos), or L4 (35S-L4-GUS-nos), respectively; 35SdN$^m$ (also referred to as 35SΔ*) comprises 35S linked with dN$^m$ which is derived from tCUPdN but lacks the Kozak consensus sequence and the N terminal peptide. 35S comprises 35S-GUS-nos.

FIG. 9 (A) shows a graphic representation and nucleotide sequence of fragments and derivatives of dN$^m$ in association with the promoter EntCUP3 (also referred to as tCUP3). FIG. 9 (B) shows the relative activity of several constructs within a tobacco transient assay using leaf disks of uniform size. The activity of the constructs in the leaf disks are expressed as pmoles MU/min/mg GUS protein. L2, Scan3 and Scan7 comprise enhanced tCUP2 regulatory element linked with L2 and GUS (tCUP2-L2-GUS-nos), Scan3 and GUS (tCUP2-Scan3-GUS-nos), Scan7 and GUS (tCUP2-Scan7-GUS-nos), respectively; "-N" comprises tCUP2 with the N fragment removed linked with GUS (tCUP2 (-N)-GUS). FIG. 9 (C) shows GUS activity of several constructs measured in pmoles MU/min/mg within a stable Arabidopsis transformation system (the n corresponds to the sample size). tCUP2-L2 and tCUP2-2×L2 comprises enhanced tCUP2 regulatory element linked with L2 and GUS (tCUP2-L2-GUS-nos), or twice the sequence of L2 and GUS (tCUP2-2×L2-GUS-nos), respectively; tCUP3-L2 and tCUP3-2×L2 comprises enhanced tCUP3 regulatory element linked with L2 and GUS (tCUP3-L2-GUS-nos), or twice the sequence of L2 and GUS (tCUP3-2×L2-GUS-nos), respectively; DNB1 comprises tCUP2-GUS-nos, FIG. 9 (D) shows the relative activity of several constructs within a tobacco transient assay using leaf disks of uniform size. The activity of the constructs in the leaf disks are expressed as pmoles MU/min/mg GUS protein. EnhtCUP2 is also referred to as EntCUP2 and tCUP2; EnhtCUP3 is also referred to as EntCUP3 and tCUP3. EnhtCUP2-L2 and EnhtCUP2-2×L2 comprises enhanced tCUP2 regulatory element linked with L2 and GUS (tCUP2-L2-GUS-nos), or twice the sequence of L2 and GUS (tCUP2-2×L2-GUS-nos), respectively; tCUP3-L2 and tCUP3-2×L2 comprises enhanced tCUP3 regulatory element linked with L2 and GUS (tCUP3-L2-GUS-nos), or twice the sequence of L2 and GUS (tCUP3-2×L2-GUS-nos), respectively; EnhtCUP2 comprises tCUP2-GUS-nos; EnhtCUP3 comprises tCUP3-GUS-nos, EnhtCUP2(-N) comprises tCUP2 with the N fragment removed (tCUP2 (-N)-GUS); EnhtCUP3(-N) comprises tCUP3 with the N fragment removed (tCUP3(-N)-GUS). FIG. 9 (E) shows the evaluation of the expression of tCUP leader elements with the enhanced tCUP2 regulatory element in a transient GUS gene expression system in an alfalfa cell suspension culture. The activity of the constructs in the cell layer is expressed as the number of blue foci per plate. tCUP2-L2 and tCUP2-2×L2 comprises enhanced tCUP2 regulatory element linked with L2 and GUS (tCUP2-L2-GUS-nos), or twice the sequence of L2 and GUS (tCUP2-2×L2-GUS-nos), respectively; tCUP3-L2 and tCUP3-2×L2 comprises enhanced tCUP3 regulatory element linked with L2 and GUS (tCUP3-L2-GUS-nos), or twice the sequence of L2 and GUS (tCUP3-2×L2-GUS-nos), respectively; tCUP2 and tCUP3 comprises tCUP2-GUS-nos and tCUP3-GUS-nos respectively; tCUP2-N comprises tCUP2 with the N fragment removed (tCUP2 (-N)-GUS); tCUP3-N comprises tCUP3 with the N fragment removed (tCUP3(-N)-GUS). FIG. 9 (F) shows an evaluation of the expression of tCUP leader elements with the enhanced tCUP2 regulatory element in a transient GUS gene expression system in white spruce callus. Activity is expressed as the number of blue foci per plate. tCUP2-2 and tCUP2-2×L2 comprises enhanced tCUP2 regulatory element linked with L2 and GUS (tCUP2-L2-GUS-nos), or twice the sequence of L2 and GUS (tCUP2-2×L2-GUS-nos), respectively, tCUP3-L2 and tCUP3-2×L2 comprises enhanced tCUP3 regulatory element linked with L2 and GUS (tCUP3-L2-GUS-nos), or twice the sequence of L2 and GUS (tCUP3-2×L2-GUS-nos), respectively; tCUP2 and tCUP3 comprises tCUP2-GUS-nos and tCUP3-GUS-nos respectively; tCUP2-N comprises tCUP2 with the N fragment removed and GUS ( tCUP2 (-N)-GUS); tCUP3-N comprises tCUP3 with the N fragment removed and GUS (tCUP3 (-N)-GUS).

FIG. 10 (A) shows a graphic representation and nucleotide sequence of fragments of dN$^m$ in association with the promoter 35S. FIG. 10 (B) shows the relative luciferase activity of L2 and L4 in the bacterial reporter system *E. Coli*. pEPLUX comprises 35Slinked to LUX, the luciferase gene. p35SL2LUX and p35SL4LUX comprises 35S linked with L2 or L4 respectively, upstream of the luciferase (LUX) ATG. −206TAP is a construct used as a negative control as it does not carry the luciferase gene.

FIG. 11 (A) shows the contructs used for the analysis presented in FIG. 11(B). p2ZOp-2E-CAT-Long comprises the promoter ie2 pm linked with dN$^m$ and CAT; p2Zop-2E-CAT-Short 1 mer comprises the promoter ie2 pm linked with L2 and CAT; p2Zop-2E-CAT-Short 3 mer, A and B, both comprises the promoter ie2 pm linked with 3 copies of L2 in ahead-to head-to-toe order and CAT; p2Zop-2E-CAT comprises the promoter ie2 pm linked directly to CAT.

DESCRIPTION OF PREFERRED EMBODIMENT

Figure 1A:
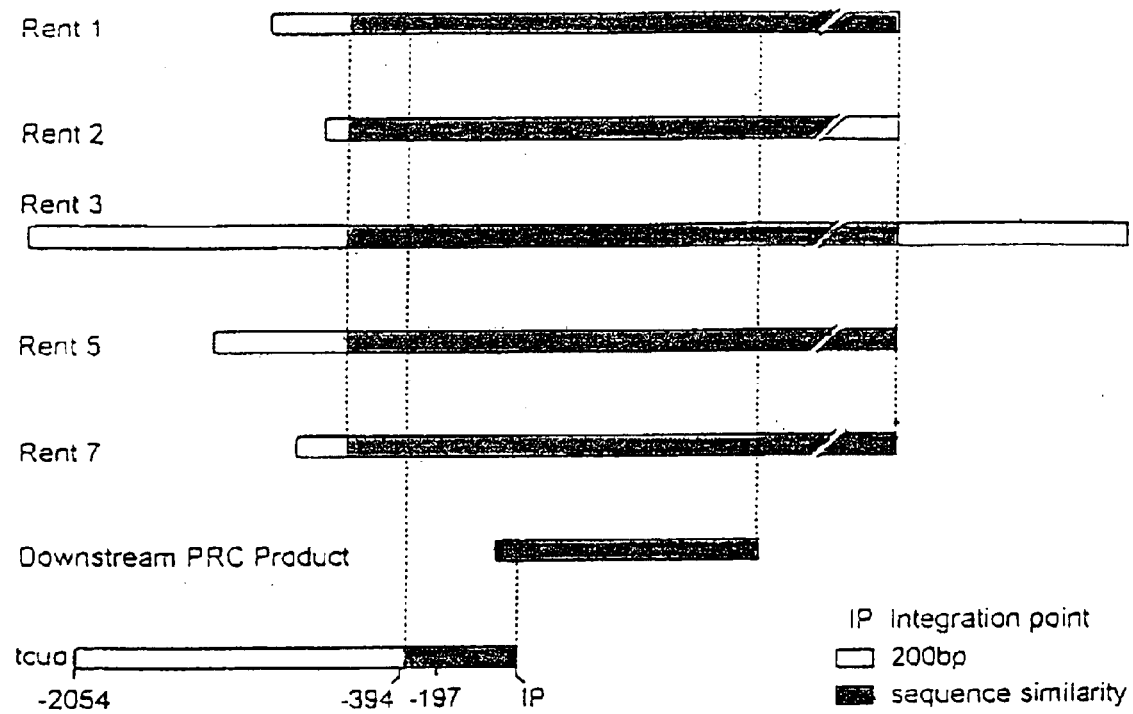
FIG. 1(A) shows a graphic representation of the sequence alignments between the different RENT clones and T1275.

The present invention relates to regulatory elements capable of mediating the translational efficiency of a transcript linked in operative association therewith. The translational regulatory elements of the present invention may also be used in combination with other regulatory elements, such as promoters, enhancers, or fragments thereof, to modify the levels of expression of a gene of interest within a host.

The following description is of a preferred embodiment by way of example only and without limitation to the combination of features necessary for carrying the invention into effect.

The present invention is directed to translational regulatory elements, including but not limited to, those defined by:

SEQ ID NO:2 (NdeI-SmaI fragment of tCUP);
SEQ ID NO:3 (ΔN with Kozak sequence);

SEQ ID NO:4 (ΔN without Kozak sequence);
SEQ ID NO:6 (L2);
SEQ ID NO:7 (L3);
SEQ ID NO:8 (L4);
SEQ ID NO:9 (L5);
and analogs or fragments thereof, for example but not limited to:

SEQ ID NO:15 (SCAN1);
SEQ ID NO: 16 (SCAN2);
SEQ ID NO: 17 (SCAN3)
SEQ ID NO:18 (SCAN4);
SEQ ID NO:19 (SCAN5);
SEQ ID NO:20 (SCAN6);
SEQ ID NO:21 (SCAN7).;
nucleotides 1–16 of SEQ ID NO:6 (L2C);
nucleotides 10–24 of SEQ ID NO:6 (L2R);
SEQ ID NO:22 (2×L2);
SEQ ID NO:23 (B1–L2);
SEQ ID NO:24 (B7–L2); or
SEQ ID NO's:25–27 (L2D1, L2D2 and L2D3)

Several of these translational regulatory elements were obtained from a family of constitutive regulatory elements identified via T-DNA tagging with a promoterless β-glucuronidase (GUS) gene within plants. This family of regulatory elements has been termed RENT (repetitive elements *Nicotiana tabacum*; see FIG. 1 (A); and SEQ ID NO's: 10 to 14). One member of the RENT family has been termed "T1275" or "tCUP" (for tobacco constitutive promoter; FIG. 1(B) and SEQ ID NO:1; see PCT/CA97/00064, PCT/CA99/0057, and U.S. Pat. No. 5,824,872 which are incorporated by reference). However, it is to be understood that analogs, fragments, or derivatives of these translational regulatory elements, translational regulatory elements that exhibit from about 70% similarity to the nucleotide sequence of, for example, but not limited to, SEQ ID NO's 5 to 9:, or translational regulatory elements that hybridize to the above listed nucleotide sequences (e.g. SEQ ID NO's: 2–4, 6–9, 15, 16, 18–19), preferably the sequences defined by SEQ ID NO's: 5 to 9 under stringent hybridization conditions, are also included within the scope of the present invention.

By "regulatory element" or "regulatory region", it is meant a portion of nucleic acid typically, but not always, upstream of a gene, and may be comprised of either DNA or RNA, or both DNA and RNA. Regulatory elements may be capable of mediating organ specificity, or controlling developmental or temporal gene activation and include promoter elements, core promoter elements, elements that are inducible in response to an external stimulus, elements that are activated constitutively, or elements that decrease or increase promoter activity such as negative regulatory elements or transcriptional enhancers, respectively.

"Regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as listed above) that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both.

"Regulatory elements" as used herein, also includes elements that are active following transcription initiation or transcription, for example, regulatory elements that modulate gene expression such as translational and transcriptional enhancers, translational and transcriptional repressors, and mRNA stability or instability determinants. These latter regulatory elements are defined as "translational regulatory elements". Without wishing to be bound by theory, translational regulatory elements may effect the amount of protein produced within an expression system or host, by mediating the rate of the initiation of translation, either positively (e.g. a translational enhancer) or negatively (e.g. a translation repressor), via one or more mechanisms. The effect of a translational regulatory element can be observed in several ways, including altered protein production with a host. Translational regulatory elements may be either DNA, or following transcription, RNA, for example the leader sequence of mRNA.

The translational regulatory elements, or fragments thereof, of the present invention maybe operatively associated with other regulatory elements as defined above, in order to modulate the amount of protein produced within a host. Such modulation may include enhancing or repressing transcriptional activity of the heterologous regulatory element, modulating post-transcriptional events, or both enhancing or repressing transcriptional activity of the heterologous regulatory element and modulating post-transcriptional events. For example, one or more translational regulatory elements, or fragments thereof, of the present invention may be operatively associated with constitutive, inducible, tissue specific promoters or fragment thereof, to modulate the activity of such promoters and the amount of protein produced within a bacteria, yeast, fungi, plant, tree, insect, or animal.

There are generally two types of promoters, inducible and constitutive promoters. An inducible promoter is a promoter that is capable of directly or indirectly activating transcription of one or more DNA sequences or genes in response to an inducer. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible promoter maybe exposed to an inducer by externally applying the inducer to the cell or plant such as by spraying, watering, heating or similar methods. Furthermore, included within this definition are tissue specific promoters that are induced by a developmental signal.

The term "constitutive" as used herein does nor necessarily indicate that a gene is expressed at the same level in all cell types, but that the gene is expressed in a wide range of cell types, although some variation in abundance is often observed. Examples of constitutive regulatory elements include, but are not limited to, regulatory elements obtained from the CaMV 35S transcript. (Odell et al., 1985, *Nature,*

313: 810–912, which is incorporated by reference), the rice actin 1 (Zhang et al, 1991, *Plant Cell,* 3: 1155–1165, which is incorporated by reference) and triosephosphate isomerase 1 (Xu et al, 1994, *Plant Physiol.* 106: 459–467, which is incorporated by reference) genes, the maize ubiquitin 1 gene (Cornejo et al, 1993, *Plant Mol. Biol.* 29: 637–646,which is incorporated by reference), the Arabidopsis ubiquitin 1 and 6 genes (Holtorf et al, 1995, *Plant Mol. Biol.* 29: 637–646, which is incorporated by reference), the tobacco translational initiation factor 4A gene (Mandel et al, 1995 *Plant Mol. Biol.* 29: 995–1004, which is incorporated by reference), and T1275 (also known as tCUP; PCT/CA97/00064, PCT/CA99/0057, and U.S. Pat. No. 5,824,872 which are incorporated by reference).

Figures 6A, 6B:
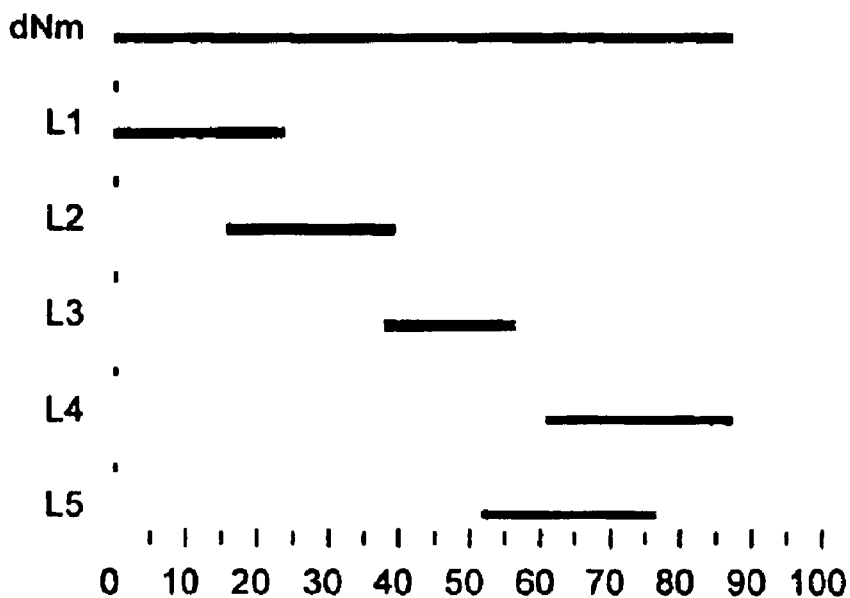
FIG. 6(A) shows a graphic representation of 5 fragments of dNm, L1–L5 (Linker1 to Linker 5, respectively).
FIG. 6(B) shows the nucleotide sequences of L1–L5 (Linker 1 to Linker 5).

The present invention is directed to nucleotide sequences which comprise regulatory elements capable of mediating the translational efficiency of, and the expression of, a gene in operative association therewith. The regulatory elements of the present invention include, but are not limited to, those localized within a NdeI-SmaI fragment of T1275 (tCUP; SEQ ID NO:1; see FIG. 1(B)). A translational regulatory element may comprise the nucleotide sequence as defined by nucleotides 2084–2224 of SEQ ID NO: 1 or an analog thereof, or the element may comprise from about 70% similarity to the nucleotide sequence of nucleotides 2084–2224 of SEQ ID NO: 1 (i.e. a portion of the NdeI-SmaI fragment from NdeI to the integration point of T1275 at nucleotide 2224). The translational regulatory element may include a translational enhancer, for example but not limited to that defined by SEQ ID NO:6, (L2; FIGS. 6 (A) and (B)) or an analogue thereof, for example, but not limited to SEQ ID NO's: 15, 16, 18–20,22–27 or nucleotides 1–16 or 10–24 of SEQ ID NO:6, or may comprise from about 70% to about 100% similarity with the nucleotide sequence as defined by SEQ ID NO's:6, 15, 16, 18–20, 22–27 or nucleotides 1–16 or 10–24 of SEQ ID NO:6, or that hybridizes to the nucleotide sequence of SEQ ID NO's:6, 15, 16, or 18–20, 22–27, or nucleotides 1–16 or 10–24 of SEQ ID NO :6 under stringent conditions. The translational regulatory element may also include other translational regulatory elements (either as an activator or repressor, depending upon the organism within which it is introduced), for example but not limited to those defined by SEQ ID NO:7, (L3; FIGS. 6(A) and (B)), SEQ ID NO:17 (SCAN,3; FIG. 6(F)), or SEQ ID NO:21 (SCAN7; FIG. 6(F), or an analogue thereof, or may comprise from about 70% to about 100% similarity, or that hybridizes to the nucleotide sequence SEQ ID NO's:7, 17 or 21, under stringent conditions. The translational regulatory element may also include a translation enhancer, for example but not limited to that defined by SEQ ID NO:5 (L16), SEQ ID NO:8 (L4) or SEQ ID NO:9 (L5; see FIGS. 6(A) and 6(B)), or and analogue thereof, or may comprise from about 70% to about 100% similarity, or that hybridizes TO the nucleotide sequence SEQ ID NO's: 5, 8 or 9, under stringent conditions.

The translational regulatory elements of the present invention exhibit a high degree of homology with members of the RENT family of repetitive elements (SEQ ID NO's: 10–14). For example, with reference to FIG. 1(C), the high degree of similarity between these nucleotide sequences can be seen. In FIG. 1(C), the nucleotide sequence of L2 comprises nucleotides 510–533, and the nucleotide sequence of L3 comprises nucleotides 531–548, of the RENT family of repetitive elements. Regions of similarity of L1, L4 and L5 are also present.

A shortened fragment of the NdeI-SmaI fragment, referred to as "ΔN", "dN", "deltaN", or "tCUP delta", is also characterized within the present invention. ΔN was prepared by mutagenesis replacing the out of frame ATG (located at nucleotides 2087–2089, SEQ ID NO: 1) within the NdeI-SmaI fragment (see FIG. 4). ΔN constructs with (SEQ ID NO:3) or without (SEQ ID NO:4) a Kozak consensus sequence were also characterized (Tables 5 and 6, in Examples) and found to exhibit translational enhancer activity. Therefore, regulatory elements of the present invention include, but are not limited to, post-transcriptional or translational regulatory elements localized at nucleotides 1–97 of SEQ ID NO's:3 and nucleotides 1–86 of SEQ DI NO's: 3 or4. These post-transcriptional or translational regulatory elements may comprise the nucleotide sequence as defined by nucleotides 1–86 of SEQ ID NO's:3 or 4 (approximately corresponding to nucleotides 2170–2224 of SEQ ID NO: 1 with altered ATG as described above) or an analog thereof, or the element may comprise 70% similarity to the nucleotide sequence of nucleotides 1–86 of SEQ ID NO's:3 or 4. Furthermore, these regulatory elements may comprise the nucleotide sequence as defined by nucleotides 1–97 of SEQ ID NO:3 and comprising a Kozak sequence or an analog thereof, or the element may comprise 70% similarity to the nucleotide sequence of nucleotides 1–97 of SEQ ID NO:3.

Other regulatory elements may include a regulatory element or translational regulatory element downstream of the transcriptional start site, for example but not limited to the NdeI-SmaI fragment (nucleotides 1–188 of SEQ ID NO2) and derivatives and fragments thereof (for example nucleotides 1–141 of SEQ ID NO:2), including ΔN (nucleotides 1–129 or 1–97 of SEQ ID NO:3), $ΔN^M$ (nucleotides 1–119 or 1–86 SEQ ID NO:4), nucleotides 1–86 of SEQ ID NO:3 or 4 (approximately corresponding to nucleotides 2086 to 2170 of SEQ ID NO: 1, with an altered ATG as described above), L2 (SEQ ID NO: 6) and L3 (SEQ ID. NO: 7), L1 (SEQ ID NO:5), L4 (SEQ ID NO:8) and L5 (SEQ ID NO:9).

An "analogue" of a regulatory element, including a translational regulatory element, includes any substitution, deletion, or additions to the sequence of the regulatory element provided that the analogue maintains at least one regulatory property associated with the activity of the regulatory element. Such properties includes directing organ specificity, tissue specificity, or a combination thereof, or temporal activity, or developmental activity, or a combination thereof, or other regulatory attributes including, negative regulatory elements, enhancer sequences, or sequences that affect stability of the transcription or translation complexes or stability of the transcript. Therefore, the present invention is also directed to translation regulatory elements, and analogs, or derivatives thereof, providing that the translational regulatory element, analog, or derivative thereof exhibits translational regulatory activity, that is, the property of mediating the translational activity of a gene of interest in operative association therewith preferably, mediation of translational activity comprises altering the levels of protein expression produced using constructs as defined herein, either positively (increasing the amount of protein produced, i.e. an enhancer) or negatively (decreasing the amount of protein produced, i.e. a repressor).

The present invention is further directed to a chimeric gene construct containing a DNA of interest operatively linked to at least one translational regulatory element of the present invention. Any exogenous gene can be used and manipulated according to the present invention to result in the expression of said exogenous gene. A DNA or gene of interest may include, but is not limited to, a gene encoding a protein, a DNA that is transcribed to produce antisense RNA, or a transcript product that functions in some manner that mediates the expression of other DNAs, for example that results in the co-suppression of other DNAs or the like. A gene of interest may also include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-$\alpha$, interferon-$\beta$, interferon-$\tau$, blood clotting factors, for example, Factor VIII, Factor IX or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the structural gene of the present construct can therefore be used to construct chimeric genes for expression in plants.

The chimeric gene construct of the present invention call also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

To aid in identification of transformed host cells, for example, but not limited to a plant cell, the constructs of this invention may be further manipulated to include selectable markers. Useful selectable markers include enzymes which provide for resistance to an antibiotic such as gentamycin, hygromycin, kanamycin, and the like. Similarly, enzymes providing for production of a compound identifiable by color change such as GUS ($\beta$-glucuronidase), or luminescence, such as luciferase are useful.

Expression of gene of interest, for example but not limited to, GUS under the control of T1275 or a fragrant thereof, or the modulation of GUS expression arising from T1275 or a fragment thereof, including but not limited to N, $\Delta$N (with or without the Kozak sequence), has been observed in a range of species including corn, wheat, barley, oat, tobacco, Brassica, soybean, alfalfa, pea, potato, Ginseng, Arabidopsis, peach, white spruce, yeast, fungi, insects and bacterial cells (e.g. Tables 8–12, Examples).

Therefore, also considered part of this invention are transgenic hosts containing the chimeric gene construct comprising a translational regulatory element of the present invention. However, it is to be understood that the translational regulatory elements of the present invention may also be combined in operative association with gene of interest for expression within a range of host organisms. Such organisms include, but are not limited to:

yeast, fungi, and bacteria;

plants, both monocots and dicots, for example, corn, wheat, barley, oat, tobacco, Brassica, soybean, pea, alfalfa, potato, ginseng, Arabidopsis;

trees, for example peach, spruce;

insects, and animal.

Methods for the transformation and regeneration of these organisms are established in the art and known to one of skill in the art and the method of obtaining transformed and regenerated plants is not critical to this invention.

For example, but not to be considered limiting in any manner, insect cells, such as those derived from gypsy moth (*Lymantria dispar*) may be transiently transformed with an appropriate construct using liposomes (Campbell M. J. 1995, Biotechniques 18: pp. 1027–1032; Forsythe I. J. et al 1998, Virology 252: pp. 65–81). Yeast may also be transformed using known transformation protocols (Agatep R. et al. 1998, http://www.biomednet.com/db/tto).

The constructs of the present invention may also be introduced into plant cells using Ti plasmids, Ri plasmids, plant virus vectors, direct DNA transformation, microinjection, electroporation, etc. For reviews of such techniques see for example Weissbach and Weissbach, *Methods for Plant Molecular Biology*, Academy Press, New York VIII, pp. 421–463 (1988), Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langmans Ltd. London. pp. 561–579 (1997).

Transformed plant cells may be cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

When specific sequences are referred to in the present invention, it is understood that these sequences include within their scope sequences that are "substantially homologous" to said specific sequences. Sequences are "substantially homologous" when at least about 70%, of the nucleotides match over a defined length of the nucleotide sequence, for example, but not limited to, the RENT family of nucleotide sequences as defined herein which exhibit from about 76% sequence similarity with a fragment (nucleotides 1723 to 2224) of the nucleotide sequence of SEQ ID NO:1, the nucleotide sequences defined by L2 (SEQ ID NO:6), or L3 (SEQ ID NO:7), L1 (SEQ ID NO:5), L4 (SEQ ID NO: 8) and L5 (SEQ ID NO:9) and their derivatives (e.g. SCAN 1–7 SEQ ID NO's: 15–21, respectively), L2C (nucleotides 1–16 of SEQ ID NO:6), or L 2R (nucleotides 10–24 of SEQ D NO:6), 2×L2 (SEQ ID NO:22), B1–L2 and B7–L2 (SEQ ID NO's:23–24), L2D1, L2D2 and L2D3 (SEQ ID NO's:25–27), providing that such homologous sequences exhibit translational regulatory element activity. Such a sequence similarity may be determined using a nucleotide sequence comparison program, such as that provided within DNASIS (using, for example but not limited to, the following parameters: GAP penalty 5. #of top diagonals 5, fixed GAP penalty 10, k-tuple 2, floating gap 10, and window size 5), or using Southern or Northern hybridization under stringent conditions (see Maniatis et al., in Molecular Cloning (A Laboratory Manual), Cold Spring Harbor Laboratory, 1982) to any one of the nucleotide sequences defined by SEQ ID NO's:2–4 (N, ΔN with Kozak or ΔN without Kozak (ΔN'''), respectively), or fragments (e.g. SEQ ID NO's:5–9; L1 L5, or L2C, L2R, 2×L2, B1–L2, B7–L2, L2D1, L2D2 L2D3), or derivatives or analogs thereof (SEQ ID NO's: 15–21; SCAN1–7, respectively), or any one of SEQ ID NO's: 10 to 14 (RENT 1–3, 5 and 7), provided that the sequences maintain at least one regulatory property of the activity of the translational regulatory element as defined herein. Preferably, sequences that are substantially homologous exhibit at least about 80% and most preferably at least about 90% sequence similarity over a defined length of the molecule.

An example of one such stringent hybridization conditions may be hybridization in 4×SSC at 65° C., followed by washing in 0.1×SSC at 65° C. for an hour. Alternatively an exemplary stringent hybridization condition could be in 50% formamide, 4×SSC at 42° C., or analyses carried out by hybridization in Church aqueous phosphate buffer (7% SDS; 0.5M NaPO$_4$ buffer pH 7.2; 10 mMEDTA) at 65° C., with washes either at 50° C. in 0.1×SSC, 0.1% SDS, or 65° C. in 2×SSC, 0.1% SDS for unique sequence regions. Analogues also include those DNA sequences which hybridize to anyone of the sequences defined by SEQ ID NO:2–4, or fragments, for example SEQ ID NO's:5–9, or derivatives, for example SEQ ID NO's:15–27, thereof, under relaxed hybridization conditions, provided that said sequences maintain at least one regulatory property of the activity of the regulatory element. Examples of such relaxed hybridization conditions includes hybridization in 4×SSC at 50° C., with 30–40% formamide at 42° C., or 65° C. in 2×SSC, 0.1% SDS for example for analysis of repetitive regions as described hererin.

For shorter length fragments, for example, but not limited to, L2 or L3, and analogs, derivatives, and fragments thereof, hybridization may be carried out directly within the gel following electrophoresis and drying of the gel, or hybridization may occur using a medium (e.g. nitrocellulose or nylon) to which the nucleic acids have been transferred as is known within the art (e.g. Sambrook et al., 1989, A Laboratory Manual. New York; Cold Spring Harbor Laboratory Press). For example, dried gels, or transfer medium, may be placed in a hybridization solution containing either:

5×SSPE (0.9 NaCl, 50 mM NaPO$_4$, 5 mM EDTA), 0.1% SDS; or

1M Na$^+$;

from about 50° C. to about 80° C. Preferably, the hybridization temperature is about 5° C. below the Tm (melting temperature), where Tm is defined as:

$$Tm=81.5-16.6(\log[Na+])+0.4(\%G+C)-(600/N),$$

and, where N is the length of said nucleotide sequence. Gels are washed in 6×SSC, at the same temperature as that used for hybridization. Less stringent conditions utilize hybridization and washing temperatures of about 10 to about 15° below the Tm.

The specific sequences, referred to in the present invention, also include sequences which are "functionally equivalent" to the specific sequences. In the present invention functionally equivalent sequences refer to sequences which although not identical to the specific sequences provide the same or substantially the same function. DNA sequences that are functionally equivalent include any substitution, deletion or addition within the sequence. With reference to the present invention functionally equivalent sequences will preferably modify the amount of protein produced within a transformed host.

The use of heterologous regulatory elements is well established in the literature. For example, but not to be considered limiting in any manner, fragments of specific elements within the 35S CaMV, or tCUP promoter have been duplicated or combined with other promoter fragments to produce chimeric promoters with desired properties (e.g. U.S. Pat. Nos. 5,491,288, 5,424,200, 5,322,938, 5,196,525, 5,164,316; and PCT/CA990057).

Aside from exhibiting translational regulatory activity as described herein, oligonucleotides of 16 bps or longer may also be useful as probes or PCR primers in identifying or amplifying related DNA or RNA sequences in other tissues or organisms. For example, the nucleotides defined by, but not limited to, L2 (SEQ ID NO:6), or nucleotides 1–16, or 10–24 of SEQ ID NO:6 (L2C and L2R, respectively), L3 (SEQ ID NO:7), L1 (SEQ ID NO:5), L4 (SEQ ID NO:8) and L5 (SEQ ID NO:9) may be used as probes to obtain or identify homologous sequences in other species.

Figure 2A:
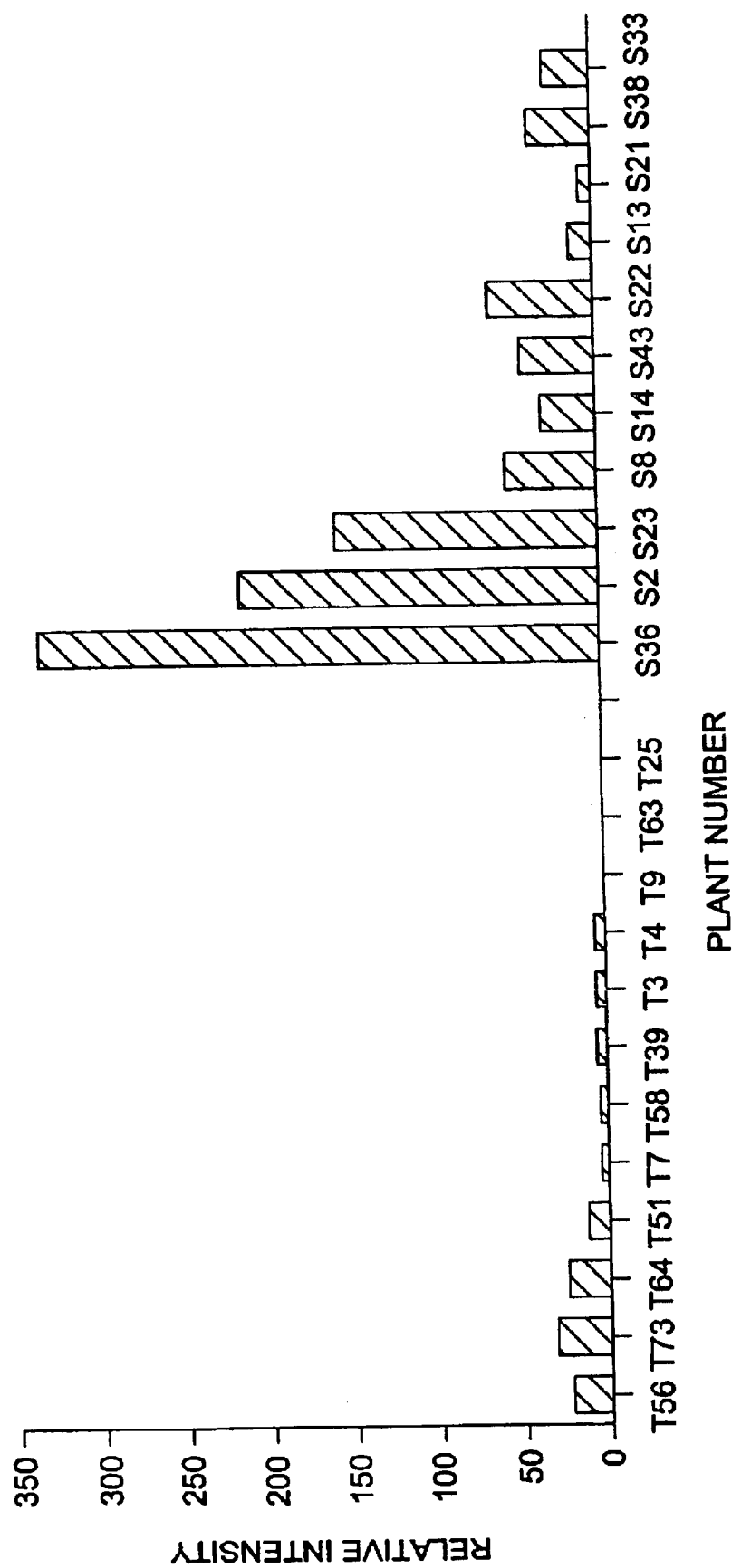
FIG. 2 shows the GUS specific activity, mRNA, and protein levels in leaves of individual, regenerated, greenhouse-grown transgenic tobacco plants containing T1275-GUS-nos (T plants), or 35S-GUS-nos (S plants).
FIG. 2(B) shows the level of accumulated GUS mRNA measured by RNase protection assay and densitometry of autoradiograms in leaves from the same randomly selected plants containing either T1275-GUS-nos (left-hand side) or 35S-GUS-nos (right-hand side).
Figure 2B:
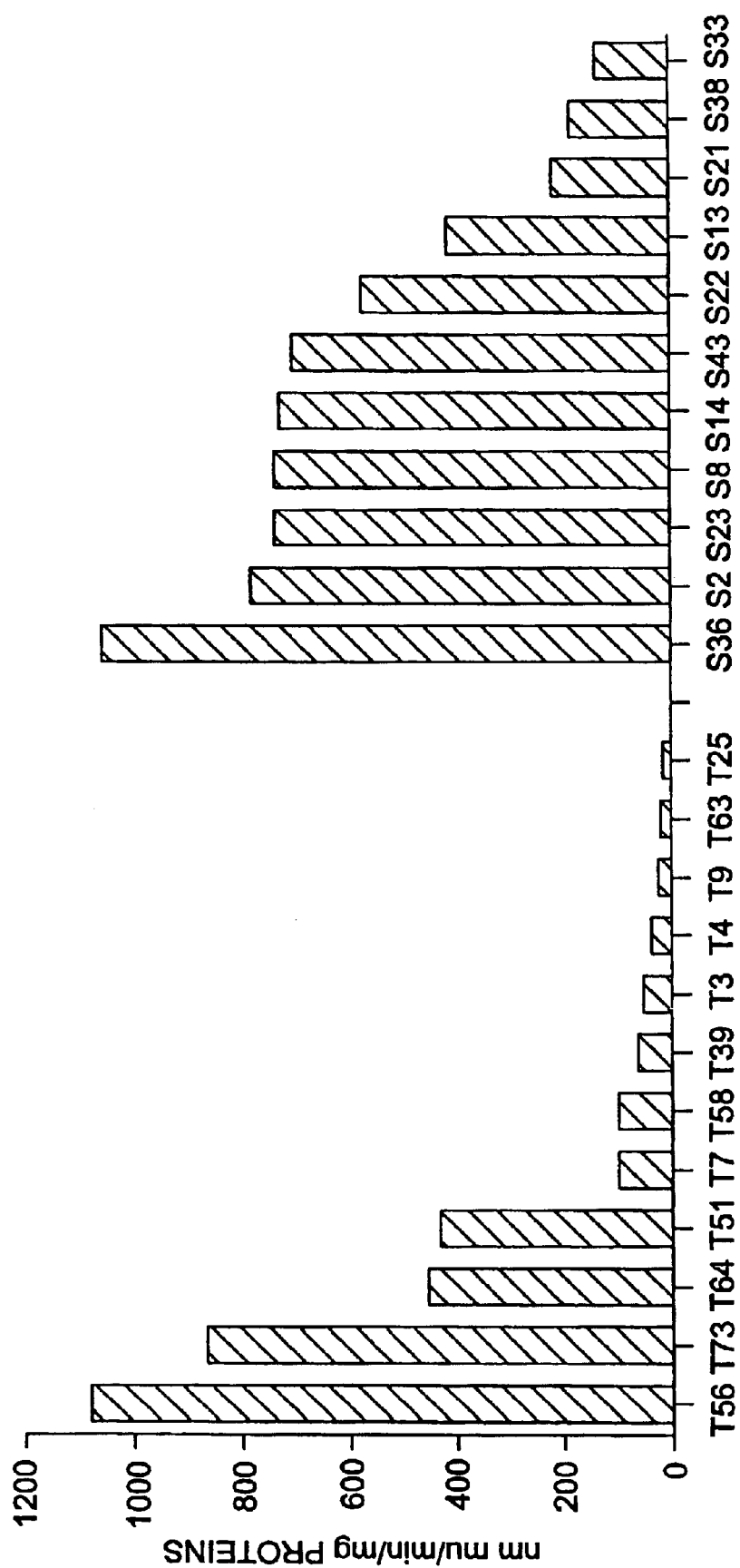
Figure 2C:

Occurrence of a Post-transcriptional Regulatory Element in the T1275 Nucleotide Sequence A comparison of GUS specific activities in the leaves of transgenic tobacco SR1 transformed with the T1275-GUS-nos gene and the 35S-GUS-nos genes revealed a similar range of values (FIG. 2(A)). Furthermore, the GUS protein levels detected by Western blotting were similar between plants transformed with either gene when the GUS specific activities were similar (FIG. 2(C)). However, analysis of GUS mRNA levels by RNase protection revealed that the levels of mRNA were about 60 fold (mean of 13 measurements) lower in plants transformed with the T1275-GUS-nos gene (FIG. 2(B)) suggesting the existence of a post-transcriptional regulatory element in the mRNA leader sequence.

Further analysis confirmed the presence of a regulatory sequence within the NdeI-SmaI fragment of the mRNA leader sequence that had a significant impact on the level of GUS specific activity expressed in all organs tested. Deletion of the NdeI-SmaI fragment (also referred to as "N") from the T1275-GUS-nos gene (see FIG. 1(B) for graphic representation of constructs) resulted in about a 46-fold reduction in the amount of GUS specific activity that could be detected in leaves of transgenic tobacco cv Delgold (see Table 1). Similar results were also observed in the transgenic tobacco cultivar SR1 and transgenic alfalfa (Table 1). Addition of the same fragment to a 35S-GUS-nos gene construct (FIG. 1(B)) increased the amount of GUS specific activity by about 5-fold in transgenic tobacco and a higher amount in transgenic alfalfa (see Table 1). Increased GUS activity was observed in organs of tobacco and alfalfa plants transformed with constructs containing NdeI-SmaI fragment (Table 2 and 3). This data is consistent with the presence of a post-transcriptional regulatory element in the NdeI-SmaI fragment.

A modulation of GUS activity was noted in a variety of species that were transformed with a regulatory element of the present invention. For example but not necessarily limited to, the NdeI-SmaI fragment of T1275 and derivatives or analogues thereof, produced an increase in activity within a variety of organisms tested including a range of plants (Tables 1–4, and FIG. 5(B)), white spruce (a conifer; Table 5) and yeast (Table 6), bacteria and insect cells (see Examples).

Figure 4A:
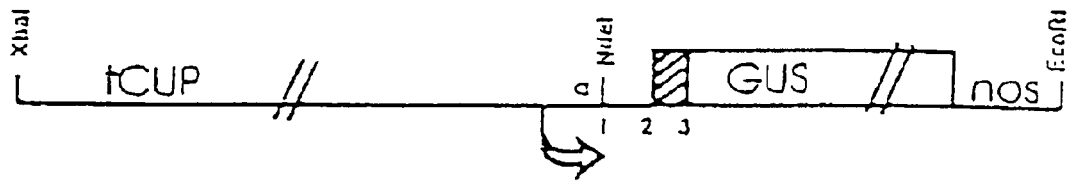
FIG. 4(A) shows T1275-GUS-nos (also referred to as tCUP-GUS-nos).

A shortened fragment of the NdeI-SmaI fragment, (referred to as "ΔN", "dN", or "deltaN") was produced that lacks the out-of frame upstream ATG at nucleotides 2087–2089 of SEQ ID NO: 1 (see FIGS. 4(A) and (B)). Constructs comprising T1275(ΔN)-GUS-nos yielded 5 fold greater levels of GUS activity in leaves of transgenic tobacco compared to plants expressing T1275-GUS-nos. Furthermore, in corn callus and yeast, ΔN significantly increased GUS expression driven by the 35 S promoter (e.g. FIG. 5(B) and Table 4).

The NdeI-SmaI regulatory elements situated downstream of the transcriptional start site functions both at a transcriptional, and post-transcriptional level. The levels of mRNA examined from transgenic tobacco plants transformed with either T1275-GUS-nos, T1275-N-GUS-nos, 35S-GUS-nos, or 35S+N-GUS-nos, are higher in transgenic plants comprising the NdeI-SmaI fragment under the control of the T1275 regulatory element but lower in those under control of the 35S promoter, than in plants comprising constructs that lack this region (FIGS. 3(A) and (B)). This indicates that this region functions by either modulating transcriptional rates, or the stability of the transcript, or both.

Sequences and structures in 5'-UTR (untranslated region) can affect translation efficiency, either positively or negatively. Such sequences are collectively called translational regulatory elements, herein. Translational enhancers have been identified in various organisms including E. coli and bacteriophages, where a Shine-Dalgarno (SD) motif (Shine and Dalgarno, 1975, Nature, 254, 34–38) can be found in many mRNAs. Plant viruses also have special mechanisms to rake over their host's protein synthesis apparatus. While the mechanism may be diverse, the presence of enhancer elements in the 5' leaders of their mRNA contributes a major mechanisms identified so far. Several examples for translational enhancers include the Omega element in tobacco mosaic virus (Gallie and Walbot, 1992, Nucleic Acid Res. 20, 4631–4638); the 5' alpha-beta leader of the potato virus X (Tomashevshaya et al., 1993, J. Gen. Virol. 74, 2727–2724); and the 5' leader of potato virus S RNA (Turner, et al., 1999, Arch. Virol. 144, 1451–1461).

Enhancer sequences have been isolated from plant genes, such as two elements from the psaDb gene of Nicotiana sylvestris (Yamamoto et al., 1995. J. Biol. Chem. 270, 12466–12470). Some other sequences may confer tissue-specific expression patterns, such as the leader of the tomato late pollen gene lat52 (Bates et al., 1996, Plant J.10, 613–623).

As disclosed herein, the NdeI-SmaI region, and fragments thereof function post-transcriptionally. The ratio of GUS specific activity to relative RNA level in individual transgenic tobacco plants that lack the NdeI-SmaI fragment is lower, and when averaged, indicates an eight fold reduction in GUS activity per RNA, than in plants comprising this region (FIG. 3(C)). Similarly, an increase, by an average of six fold, in GUS specific activity is observed when the NdeI-SmaI region is added within the 35S untranslated region (FIG. 3(C)). The GUS specific activity:relative RNA levels are similar in constructs containing the NdeI-SmaI fragment (tCUP-GUS-nos and 35-S±N-GUS-nos). These results indicate that the NdeI-SmaI fragment modulates gene expression post-transcriptionally.

Translation of transcripts in vitro demonstrate an increase in translational efficiency of RNA containing the NdeI to SmaI fragment compared to transcripts lacking this fragment (Table 7). Furthermore, the levels of protein produced using mRNAs comprising the NdeI-SmaI fragment are greater than those produced using the known translational enhancer of Alfalfa Mosaic Virus RNA4. These results indicate that this region functions post-transcriptionally, as a translational enhancer.

Figures 6C, 6D:
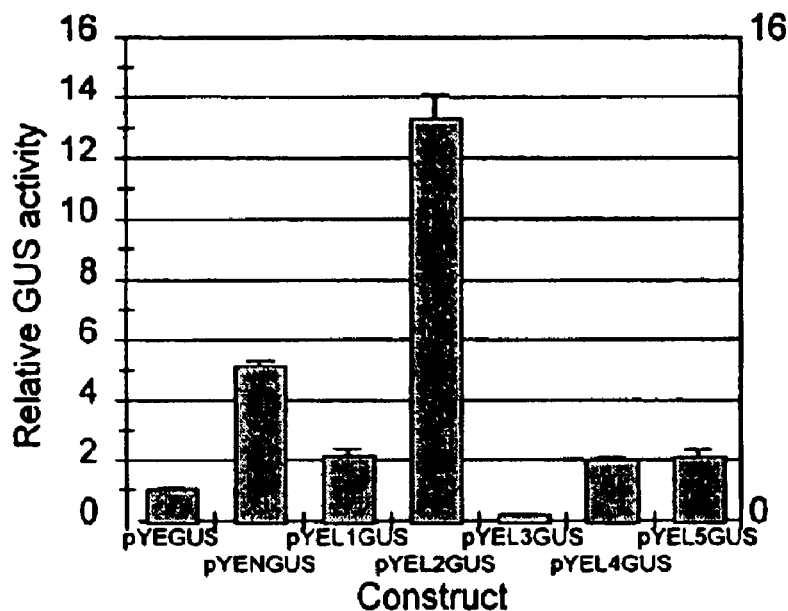
FIG. 6(C) shows the activity of constructs comprising the linkers of FIG. 6(B) within a yeast expression system. pYEGUS, pYES2 with GUS and no added translational regulatory element; pYENGUS, pYES2 with the NdeI-SmaI fragment ("N") of tCUP and GUS; pYEL1GUS to pYEL5GUS, pYES2 with each of Linker1 to Linker 5 and GUS, respectively.
FIG. 6(D) shows the nucleotide sequences of L2 (linker2), L2C (nucleotides 1–16 of SEQ ID NO:6), and L2R (nucleotides 10–24 of SEQ ID NO:6).
Figures 6E, 6F:
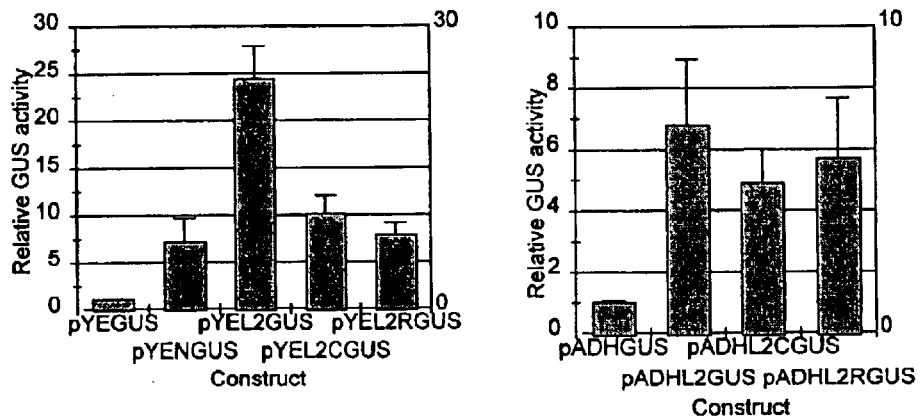
FIG. 6(E) shows the activity of constructs comprising either the inducible promoter $P_{galt}$ or the constitutive promoter $P_{ADH1}$, in operative association with "N", L2, L2C and L2R within a yeast expression system. pYEGUS, pYENGUS, as defined above; pYEL2GUS, pYES2 with L2 and GUS; pYEL2CGUS, pYES2 with L2C and GUS; pYEL2RGUS, pYES2 with L2R and GUS. pADHGUS: pYES2 comprising the $P_{ADH1}$ promoter and GUS; pADHL2GUS, pADHL2CGUS, and pADHL2RGUS, each consisting of pADHGUS along with L2, L2C and L2R fragment, respectively, and in operative association with GUS.
FIG. 6(F) shows the nucleotide of L2, and several analogs of L2, (SCAN1–SCAN to 7) comprising different triplet base changes (in bold) of L2.
Figure 6G:
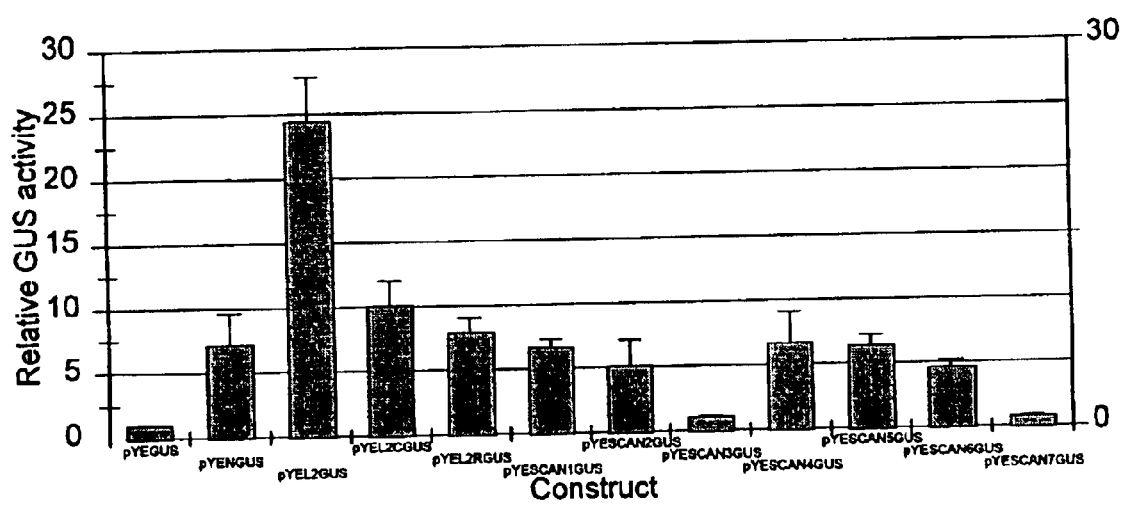
FIG. 6(G)
Figure 6H:
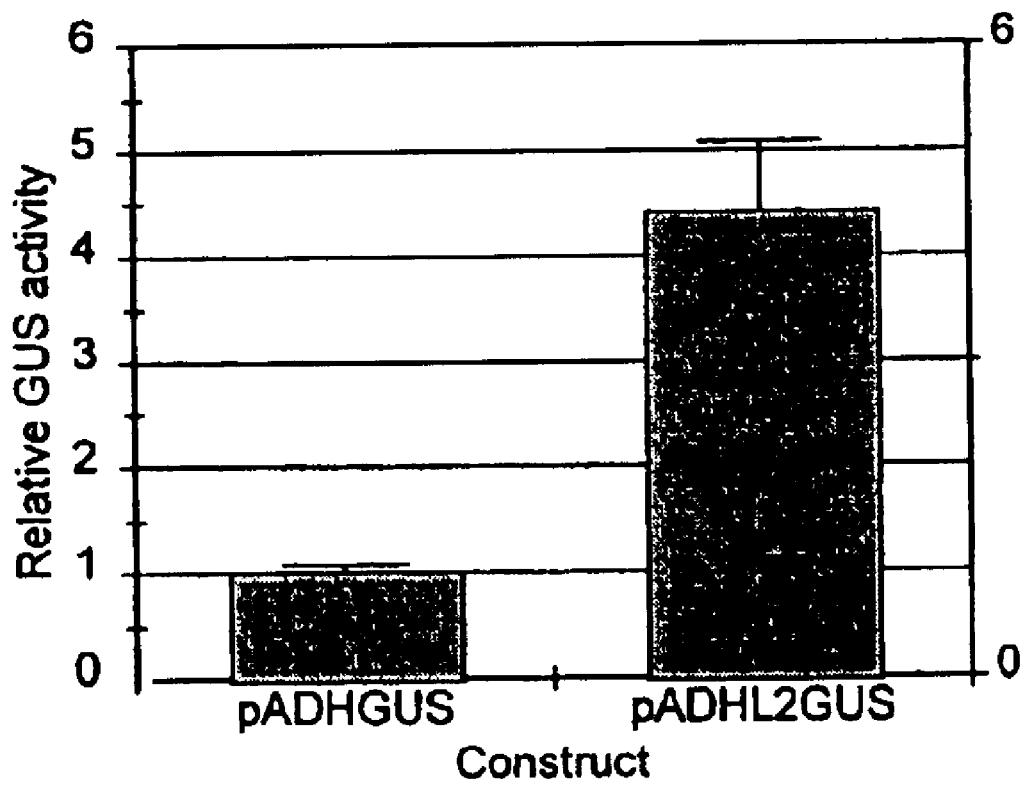
FIG. 6(H) shows the activity of constructs comprising the yeast constitutive $P_{ADH1}$ promoter, in the absence (pADHGUS) and presence (pADHL2GUS) of L2, within a yeast expression system.
Figure 6I:
FIG. 6 shows several fragments, analogs and derivatives of dNm (also referred to as ΔN$^M$), and their associated activities in a yeast expression system.
FIG. 6(P).1 shows a Northern blot analysis of culture sampled at various time points after repression of the GAL1 promoter. The Northern was probed with a GUS cDNA probe.
Figure 6J:
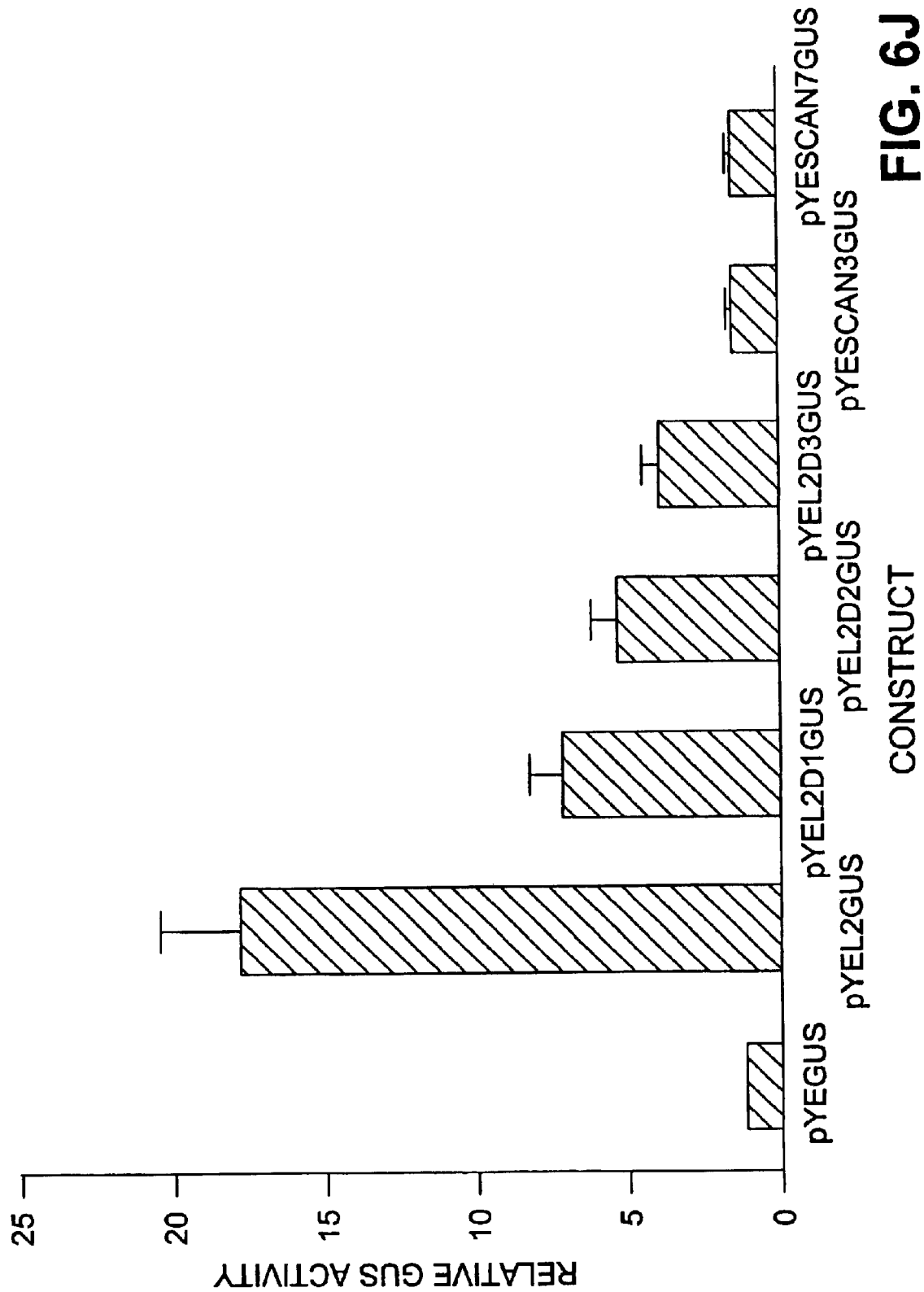
Figure 6K:
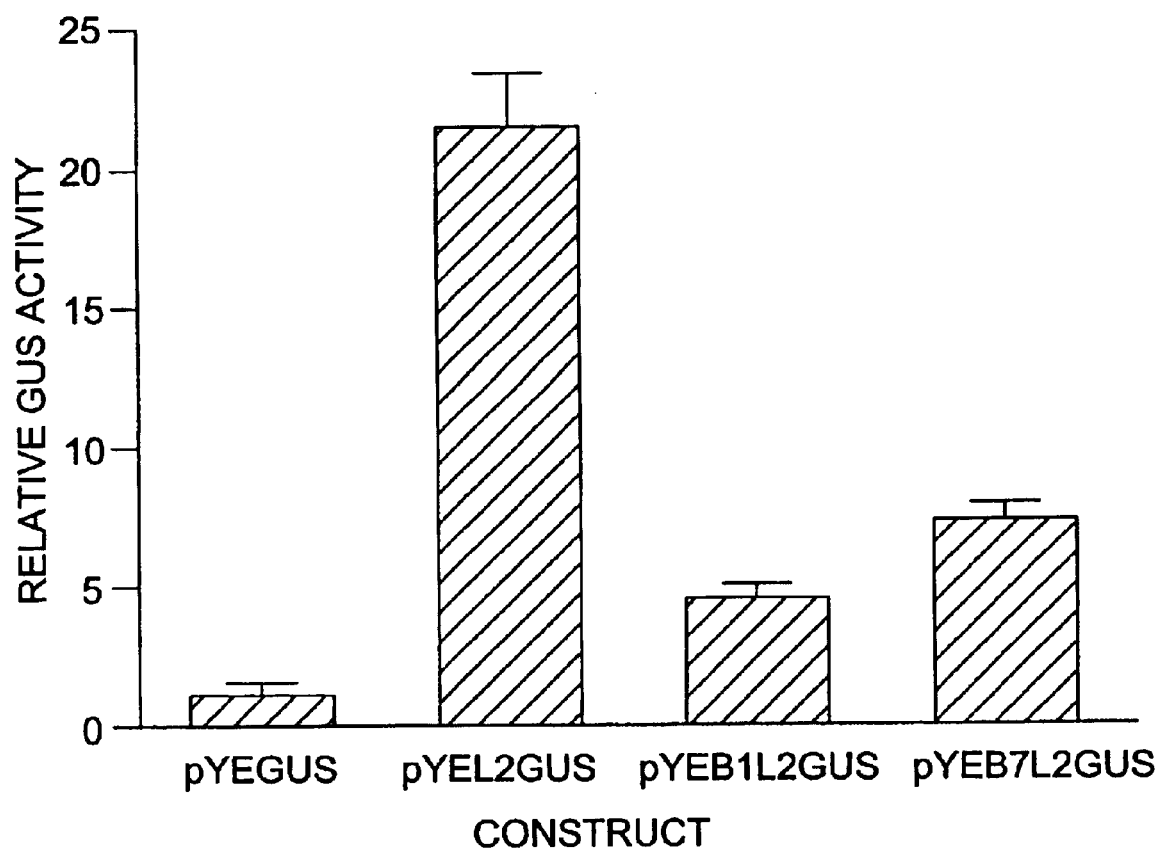
Figure 6L:
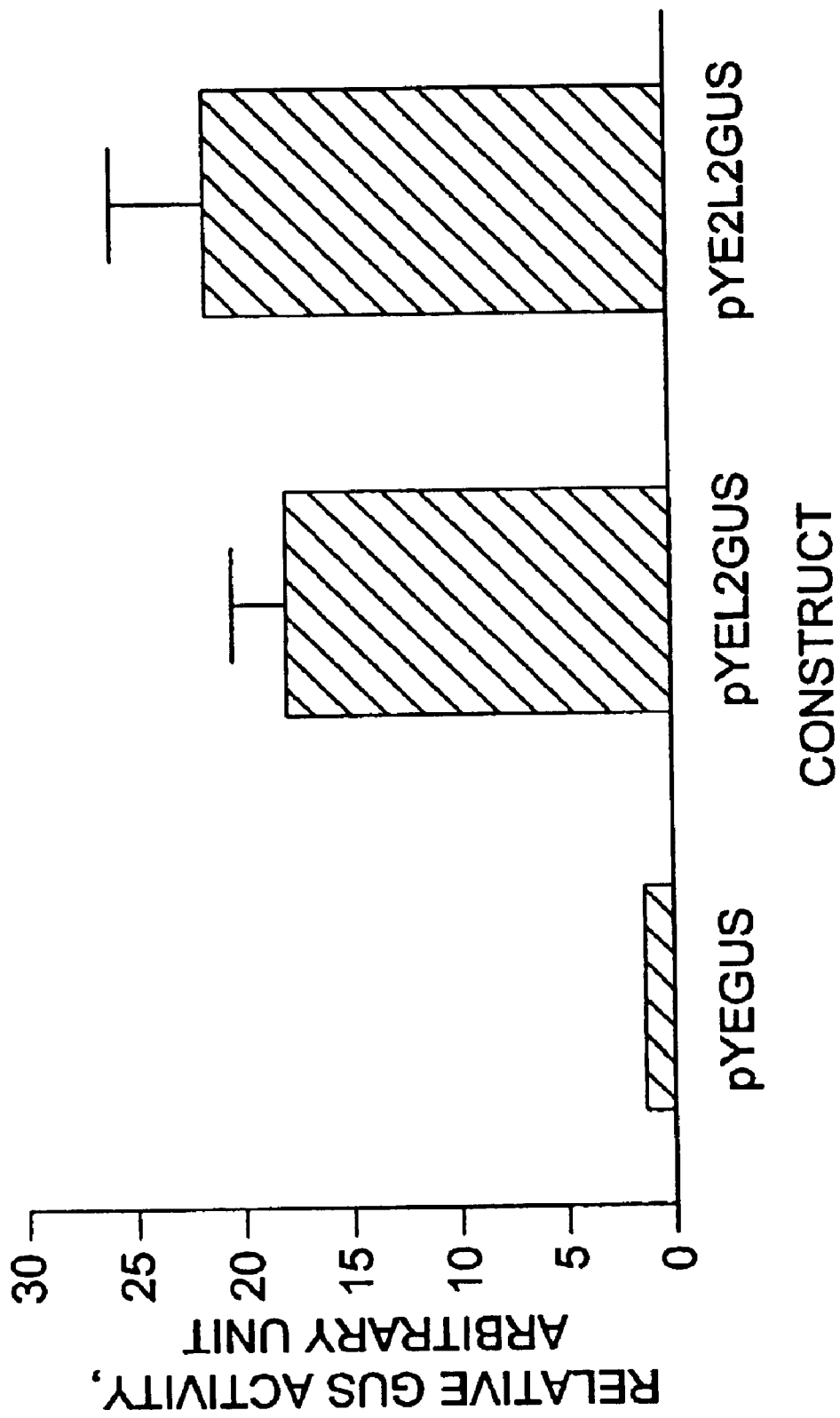

Five fragments of the dN$^M$ nucleotide sequence were also prepared (L1- L5; see FIGS. 6(A), 6(B), 6(I); SEQ ID NO's: 5–9, respectively) and characterized for their efficacy as translational regulatory elements. Each of fragments L1–L5 mediated the expression of a gene of interest within a yeast expression system (FIGS. 6(C), 6(I)). One of these fragments, L2 which is a 24 nucleotide sequence (SEQ ID NO:6), functions as a translational enhancer capable of enhancing the expression of a gene of interest by about 20 times over the control (FIG. 6(C)). This element enhanced expression of a gene of interest in operative association therewithin a range of organisms, including, but not limited to, yeast (FIG. 6) and pea (FIG. 7). Furthermore, this translational regulatory element functions with a variety of chimeric regulatory elements, for example but not limited to, 35S (FIG. 7), tCUP (native sequence), EntCUP2, Ent-CUP3 (e.g. FIGS. 7(A), 9(A)), $P_{gall}$ (FIG. 6(C), $P_{adh1}$ (FIG. 6(H)), and a Canola cold inducible promoter BN115 (data not shown). Fragments L1 (SEQ ID NO:5), L4 (SEQ ID NO:8) and L5 (SEQ ID NO:9) also exhibited translational enhancer activity to a lesser decree (about 2–3 fold increase over control in yeast). The translational regulatory element, L3 (an 18 nucleotide sequence; SEQ ID NO:7), functions as a translational repressor, reducing the expression of a gene of interest about 5 fold in yeast (FIG. 6(C)).

Further characterization in the yeast system of the L2 region (SEQ ID NO:6) comprising portions of the L2 sequence (L2C, nucleotides 1–16 of SEQ ID NO:6; and L2R, nucleotides 10–24 of SEQ ID NO:6; also see FIGS. 6(D), (E) and (I)), and scanning mutational analysis of this region (FIG. 6(F), (G) and (I); SEQ ID NO's:15–21), deletion of triplet nucleotides within L2 (FIG. 6(J); SEQ ID NO's.25–27) and use of L2 homologues from other members of the RENT family (FIG. 6(K); SEQ ID NO's:23–24) revealed that several regions of the L2 are required for optimal activity of L2. Using two L2 elements in tandem (FIG. 6(L); SEQ ID NO:22) has also shown that oligomerization of the L2 element increases its enhancement activity. Analogs, mutants, or derivatives thereof, of L2, including but not limited to, L2C, L2R, SCAN2, SCAN4, SCAN5, SCAN6, L2D1, L2D2 and 2×L2, exhibit translational enhancer activity and may be used within constructs, as translational regulatory elements, in operative association with other regulatory elements as known within the art.

Figure 7B:
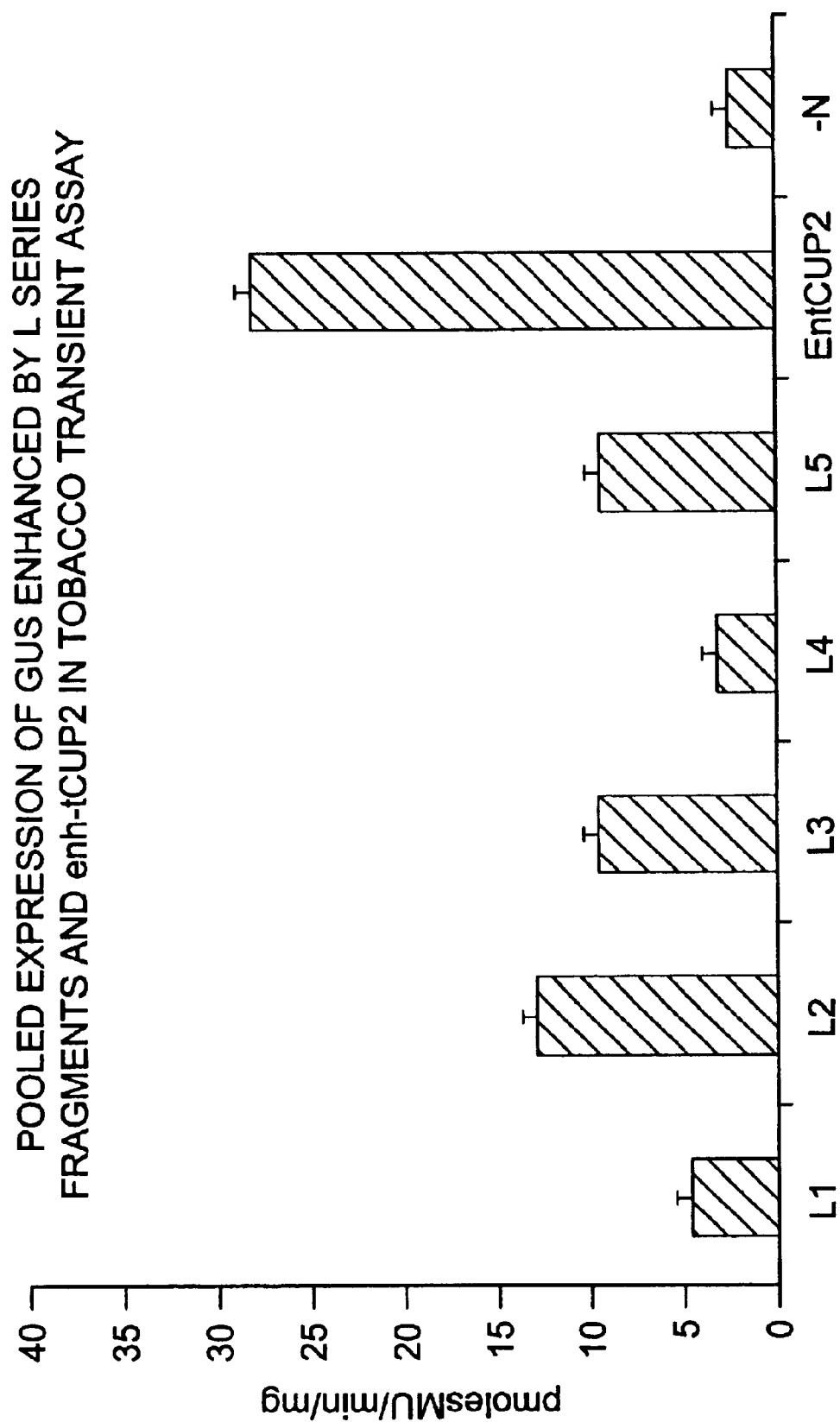
FIG. 7(B) shows the relative activity of several constructs within a tobacco transient assay using leaf disks of uniform size. The activity of the constructs in the leaf disks are expressed as pmoles MU/min/mg GUS protein. L1, L2, L3, L4 and L5 comprise enhanced tCUP2 regulatory element linked with L1 (tCUP2-L1-GUS-nos), L2 (tCUP2-L2-GUS-nos). L3 (tCUP2-L3-GUS-nos), L4 (tCUP2-L4-GUS-nos), or L5 (tCUP2-L5-GUTS-nos) respectively; "EntCUP2" (also referred to as tCUP2) comprises tCUP2-GUS-nos; "–N" comprises tCUP2 with the N fragment removed (tCUP2 (–N)).
Figure 8C:
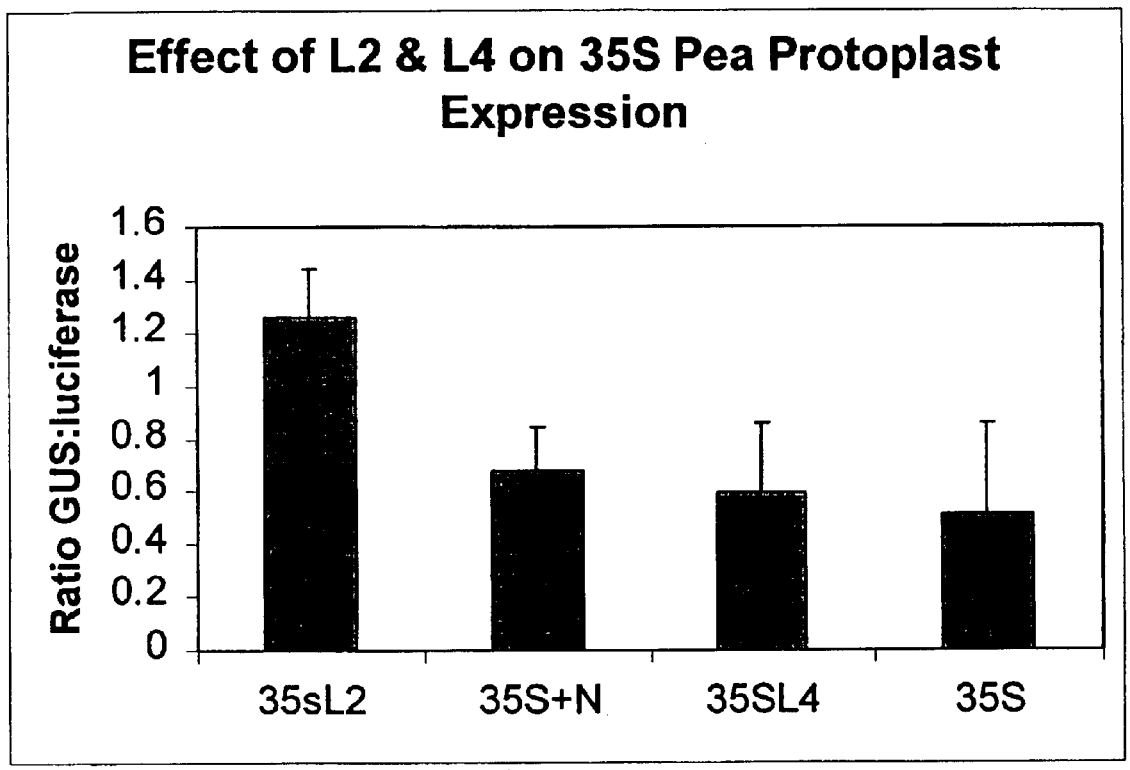
FIG. 8(C) shows the relative activity of several constructs within a pea protoplast expression system. The activity of the constructs in the protoplast are expressed as a ratio of GUS to luciferase (control) activity. 35SL2 and 35SL4 comprises 35S linked with L2 and GUS (35S-L2-GUS-nos), or L4 and GUS (35S-L4-GUS-nos), respectively; 35S–N comprises 35S linked with the NdeI-SmaI fragment (35S+N-GUS-nos); 35S comprises linked with GUS (35S-GUS -nos).
Figure 8F:
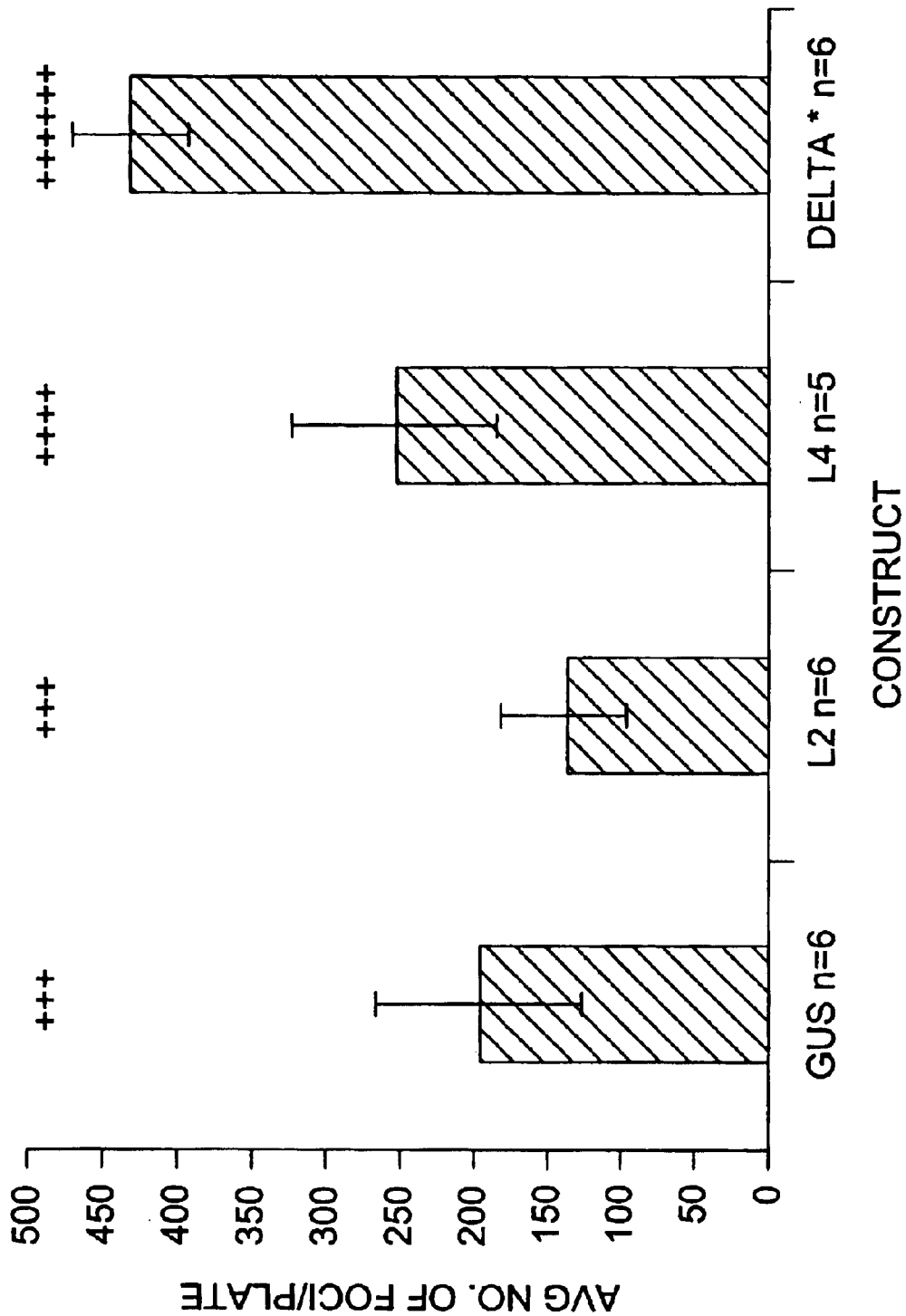
FIG. 8 shows the activity of constructs within a range of different plants.
FIG. 8(A) shows the constructs used for the studies presented in FIGS. 8 (B)–(D) pertaining to NdeI-SmaI fragment (N) and derivatives of the 35S sequence.
FIG. 8(B) shows GUS activity of several constructs within a stable Arabidopsis transformation system, expressed as pmoles MU/min/mg GUS protein ("n" corresponds to sample size). "L2" and "L4": 35S linked with L2 and GUS (35S-L2-GUS-nos), or L4 and GUS (35S-L4-GUS-nos), respectively; "Deltas" (also referred to as 35SdN$^m$) comprises 35S linked with $dN^m$ and GUS; "GUS" comprises 35S linked directly to GUS (35S-GUS-nos).
FIG. 8(D) shows the relative activity of several constructs within a tobacco transient assay using leaf disks of uniform size. The activity of the constructs in the leaf disks are expressed as pmoles MU/min/mg GUS protein. 35SL2 and 35SL4 comprises 35S linked with L2 and GUS (35S-L2-GUS-nos), or L4 and GUS (35SL4-GUS-nos), respectively, "35S+N" comprises 35S linked with the NdeI-SmaI fragment and GUS (35S+N-GUS-nos); 35S comprises 35s linked with (GUS35S-GUS-nos).
Figure 8G:
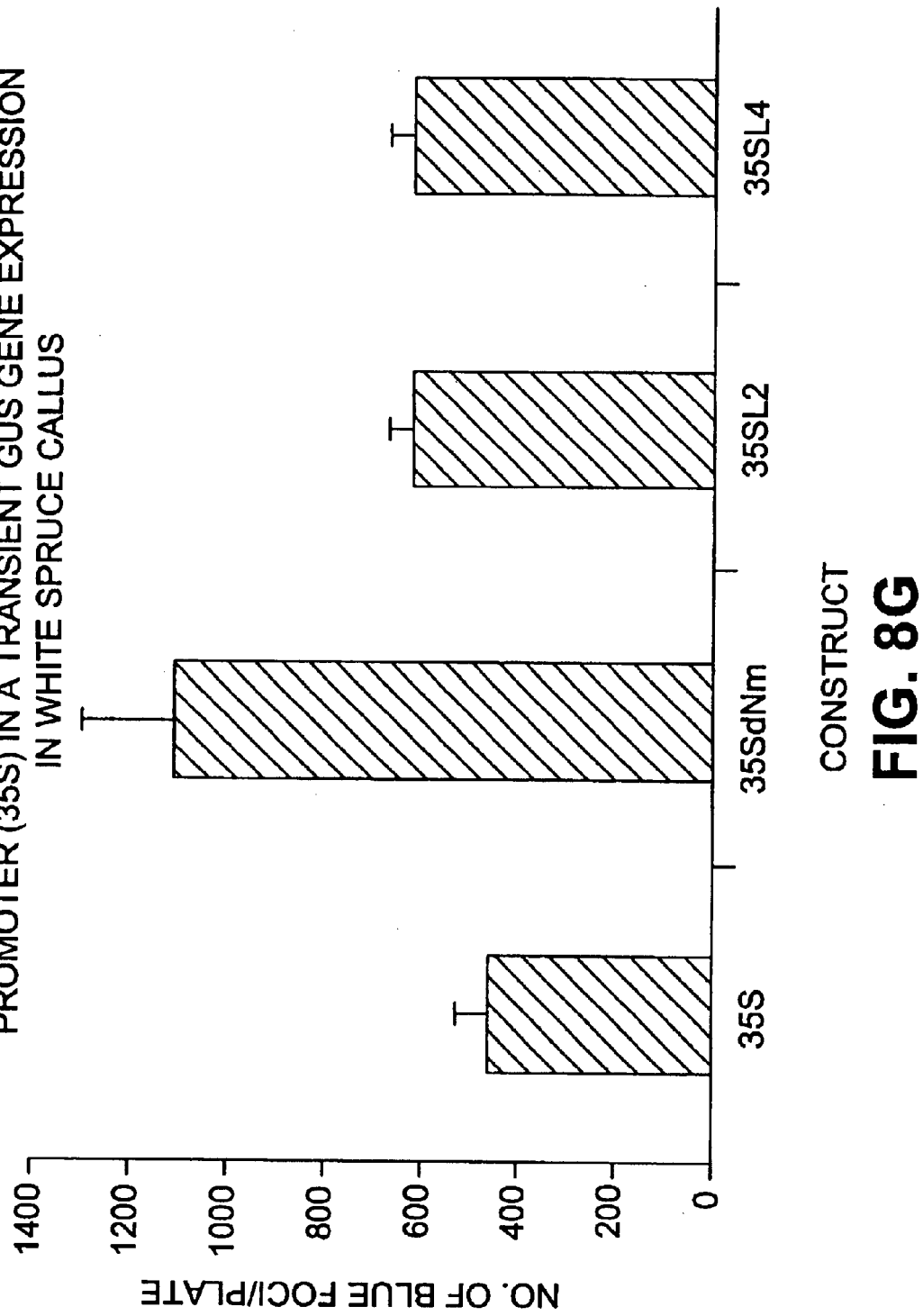

The activity of the five fragments of dN$^m$ (see FIG. 7(A); L1–L5; SEQ ID NO's:5–9, respectively) was also characterized in a range of plant species and in conifers using transient assays. The promoter tCUP2 was used for the constructs in these experiments. The results show that L2 is the most active of those fragments in tobacco, alfalfa and white spruce (FIGS. 7(B), (C) and (D), respectively). They also show that the four other fragments (L1, L3, L4 and L5) also have translation enhancing activity, however the activity is species dependant. For example, L3 and L5 have significative enhancing activity in the tobacco assay, and L1 and L4 have significative enhancing activity in white spruce. The activity of the fragments L2 and L4 was further tested using constructs driven by the promoter 35S (FIG. 8(A)). Transformation of Arabidopsis plants as well as transient assays in pea protoplasts, tobacco leaves, alfalfa cell culture, and corn and white spruce callus were performed (FIGS. 8(B) to (G)). In general, the results followed the same trend as the results observed using the tCUP2 promoter.

Figure 9A:
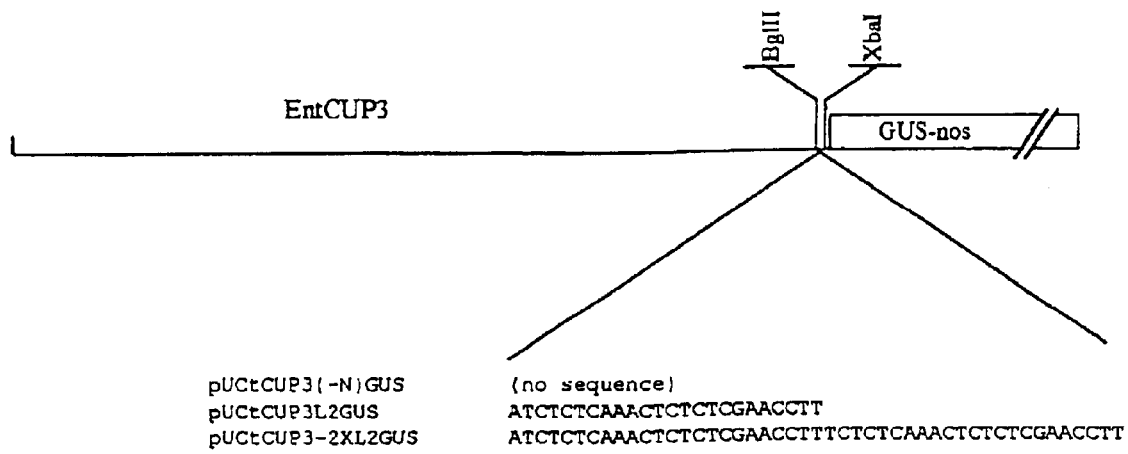
FIG. 9 shows several fragments, analogs and derivatives of dN$^m$, and their associated activities in a range of plant species and in conifers.
Figure 9B:
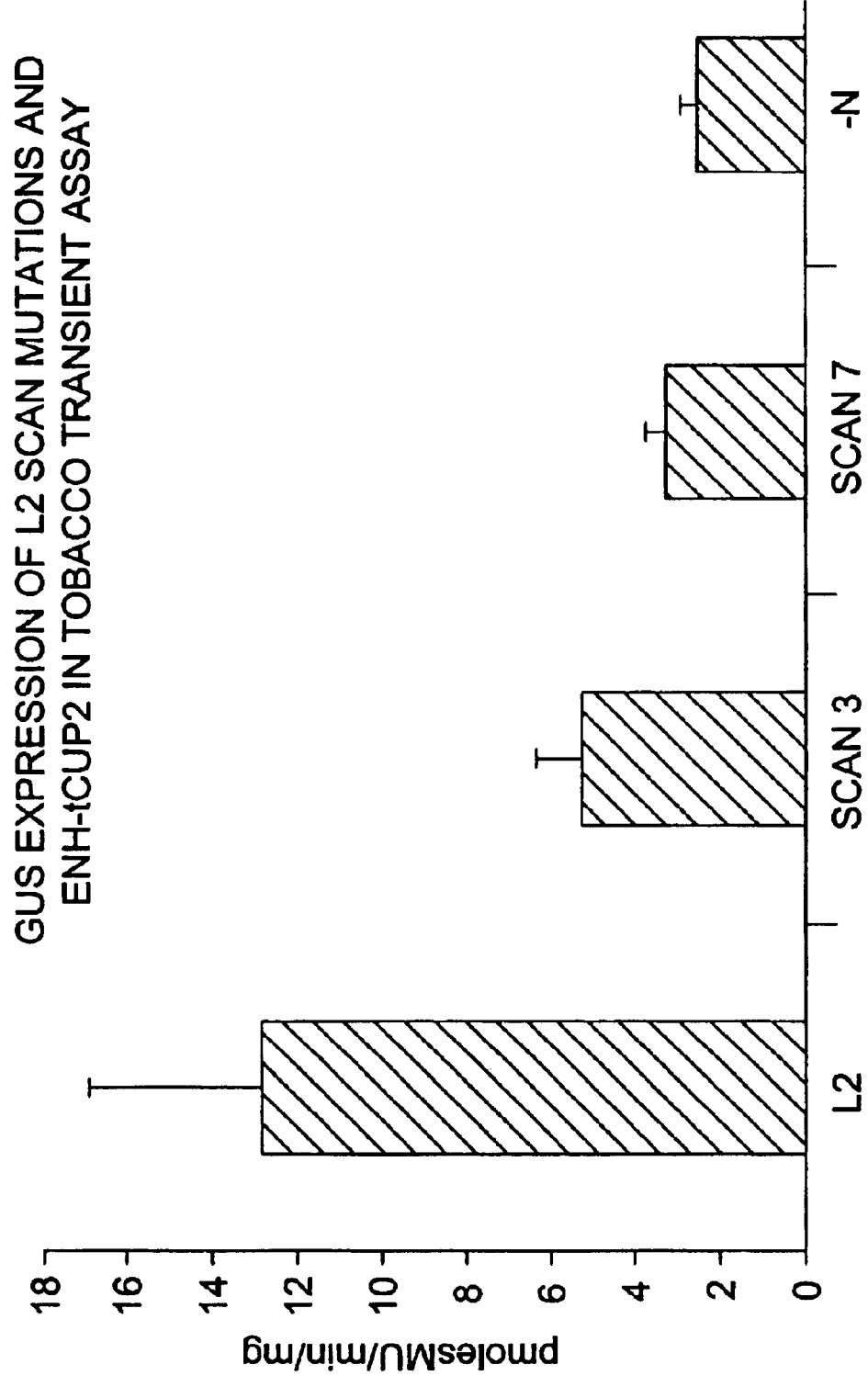

The characterization of some of the L2 derivatives, including SCAN3, SCAN7 and 2×L2 (FIGS. 7(A) and 9(A); SEQ ID NO's: 17, 22 and 22) was also performed in plants and conifers. The results (FIG. 9(B)) show that the nucleotides modified in SCAN3 and SCAN 5 are critical for enhancing activity of L2 in plants as well as in yeast (see above). The use of L2 in tandem also resulted in an increase of enhancement activity of L2 in Arabidopsis, tobacco, alfalfa and white spruce (FIGS. 9(C) to (F)). A difference in the increase observed after oligomerization was noted between the promoters used (tCUP2 vs tCUP3) and also between either species or assay type (transient vs stable expression).

The activity of the fragments L2 and L4 (SEQ ID NOS:6 and 8) was also tested in the bacteria E. coli (FIG. 10). Both fragments are showing enhancing activity when compared to a construct containing none of the L fragment.

Therefore, the present invention also includes several translational regulatory elements identified within the $dN^M$ sequence (SEQ ID NO:4).

Collectively, these results indicate that constructs comprising "N" (SEQ ID NO:2), ΔN (SEQ ID NO:3), $ΔN^M$ (SEQ ID NO:4), L2 (SEQ ID NO:6), fragments of L2, including L2C (nucleotides 1–16 of SEQ ID NO:6) and L2R (nucleotides 10–24 of SEQ ID NO:6), analogs or derivatives of L2 including, but not limited to SCAN1 (SEQ ID NO:15), SCAN2 (SEQ ID NO:16), SCAN4 (SEQ ID NO:18), SCAN 5 (SEQ ID NO:19), SCAN6 (SEQ ID NO:20), L2D1 (SEQ ID NO:25), L2D2 (SEQ ID NO:26), or oligomer of L2 including, but not limited to 2×L2 (SEQ ID NO:22), L1 (SEQ ID NO:5), L3 (SEQ ID NO:7), L4 (SEQ ID NO:8) and L5 (SEQ ID NO:9), or a combination thereof, function as translational enhancers within a variety of expression systems and hosts.

One, or more of the translational regulatory elements as described herein may be used in conjunction with other constitutive regulatory elements to drive the expression of a gene of interest within all organs or tissues, or both, of a plant. These elements may also be coupled or inverted in order to further mediate their activity. Furthermore, one or more of the translational enhancers may be used in association with tissue specific regulatory elements such as those well known in the art in order to drive tissue specific expression of a gene of interest. Chimeric regulatory elements comprising one or more translational regulatory elements may also be used in association with inducible regulatory elements as are known within the art.

The use of fragments of specific elements within the 35S CaMV promoter, or tCUP, or other have been duplicated or combined with other regulatory element fragments to produce chimeric regulatory elements with desired properties (e.g. U.S. Pat. Nos. 5,491,288, 5,424,200, 5,322,938, 5,196,525, 5,164,316; (PCT/CA97/00064, PCT/CA99/0057, and U.S. Pat. No. 5,824,872 which are incorporated by reference). As indicated above, the translational regulatory element or a fragment thereof, as defined herein, may also be used along with other regulatory element, enhancer elements, or fragments thereof, in order to mediate expression of a gene of interest. Furthermore, the nucleotides, or fragments thereof may be useful as probes, for example to identify other members of the RENT family of repetitive sequences, or as PCR primers in identifying or amplifying related DNA or RNA sequences in other tissues or organisms, for example, but not limited to, L1–L5 homologs.

Thus this invention is directed to translational regulatory elements and their use in association with other regulatory elements and gene combinations comprising these regulatory elements. Further this invention is directed to such translational regulatory elements and gene combinations in a cloning vector, wherein the gene is under the control of the chimeric regulatory element and is capable of being expressed in a host cell transformed with the vector. This invention further relates to transformed host cells and transgenic hosts regenerated from such host cells. The translational regulatory element, and regulatory element-gene combinations of the present invention can be used to transform any host cell for the production of any transgenic host. The present invention is not limited to any host species.

Therefore, the regulatory elements of the present invention maybe used to control the expression of a gene of interest within desired host expression system, for example, but not limited to: plants, both monocots and dicots, for example, corn, tobacco, Brassica, soybean, pea, alfalfa, potato, ginseng, wheat, oat, barley, Arabidopsis; trees, for example peach, spruce; yeast, fungi, insects, and bacteria.

Furthermore, the translational regulatory elements as described herein may be used in conjunction with other regulatory elements, such as tissue specific, inducible or constitutive promoters, enhancers, or fragments thereof, and the like. For example, the translational regulatory region, analogs, or a fragment thereof as defined herein may be used to regulate gene expression of a gene of interest spatially and developmentally within a plant of interest or within a heterologous expression system. Regulatory regions or fragments thereof, as known in the art may be operatively associated with a heterologous nucleotide sequence including one or more heterologous translational regulatory regions to increase, or otherwise modulate, the expression of a gene of interest within a host organism. A gene of interest may include, but is not limited to, a gene that encodes a pharmaceutically active protein, for example growth factors, growth regulators, antibodies, antigens, their derivatives useful for immunization or vaccination and the like. Such proteins include, but are nor limited to, interleukins, insulin, G-CSF, GM-CSF, hPG-CSF, M-CSF or combinations thereof, interferons, for example, intrferon-α, interferon-β, interferon-τ, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases chitinases, invertases, lipases, cellulases, xylanases, enzymes involved in oil metabolic and biosynthetic pathways etc. A gene of interest may also encode a protein imparting or enhancing herbicide resistance or insect resistance of a plant transformed with a construct comprising a constitutive regulatory element as described herein.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit. The scope of the present invention in any manner.

EXAMPLES

Post-Transcriptional Regulatory Elements within T1275 (tCUP)

Figure 1B:
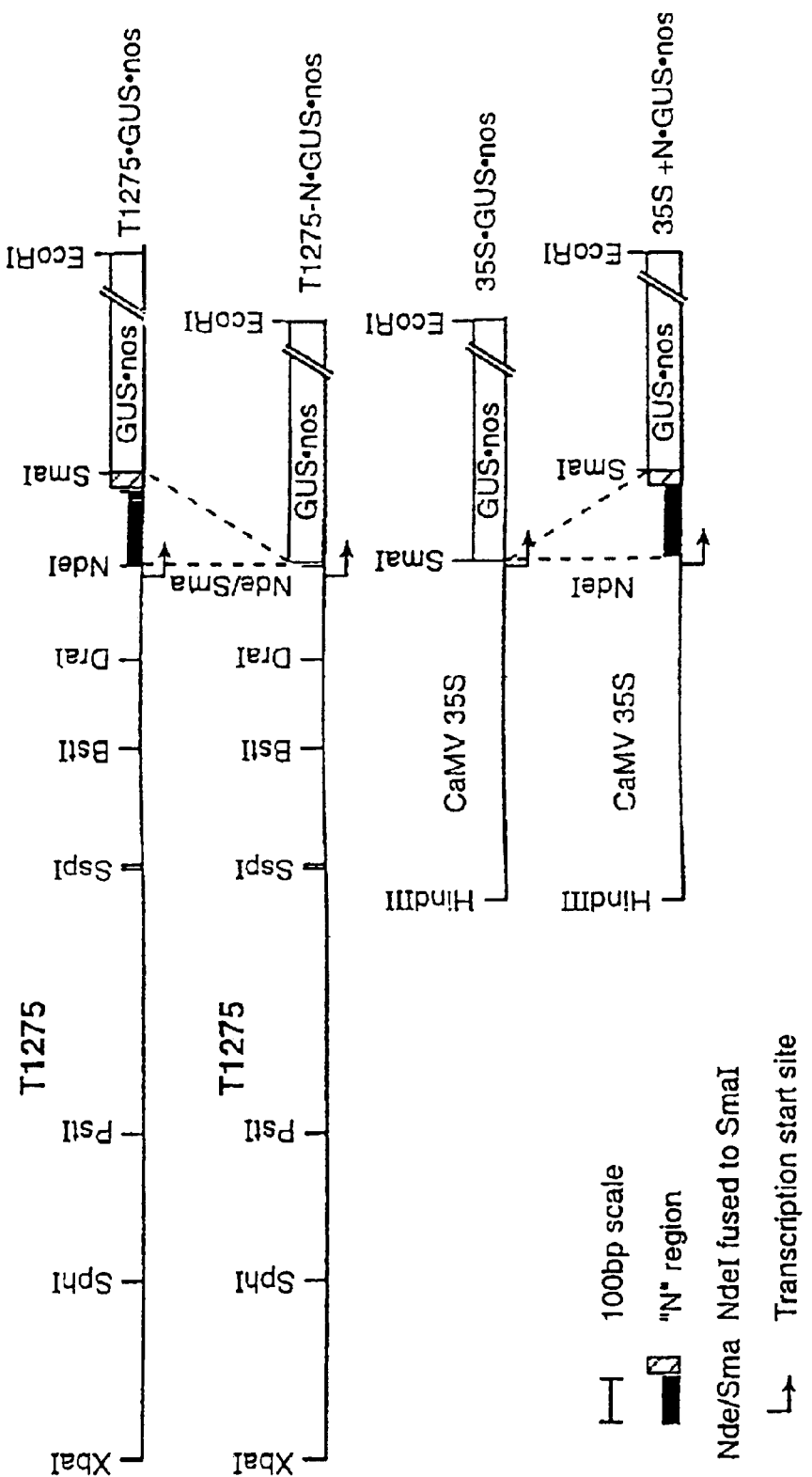
FIG. 1(B) shows deletion and insertion constructs of the 5' untranslated leader region of T1275 regulatory element and construction of transformation vectors. The constructs are presented relative to T1275-GUS-nos or 35S-GUS-nos. The arrow indicates the transcriptional start site. Plant DNA is indicated by the solid line labeled T1275, the 35S regulatory region by the solid line labelled CaMV35S, the NdeI-SmaI ("N") region by a filled in box, the shaded box coding for the amino terminal peptide, and the promoterless GUS-nos gene is indicated by an open box. The deletion construct removing the NdeI-SmaI fragment of T1275-GUS-nos is identified as T1275-N-GUS-nos. The NdeI-SmaI fragment from T1275-GUS-nos was also introduced into 35S-GUS-nos to produce 35S+N-Gus-nos.

The characterization of plants comprising the constitutive regulatory element T1275, and preliminary characterization of the regulatory element (FIG. 1; SEQ ID NO:1) has been previously described (PCT/CA97/00064, PCT/CA99/0057, and U.S. Pat. No. 5,824,872 which are incorporated by reference). Fragments of this regulatory element exhibit substantial similarity with members of the RENT family of repetitive sequences (FIGS. 1(A) and (C)).

A comparison of GUS specific activities in the leaves of transgenic tobacco SR1 transformed with the T1275-GUS-nos gene and the 35S-GUS-nos genes revealed a similar range of values (FIG. 2(A)). Furthermore, the GUS protein levels detected by Western blotting were similar between plants transformed with either gene when the GUS specific activities were similar (FIG. 2(C)). Analysis of GUS mRNA levels by RNase protection however revealed that the levels of mRNA were about 60 fold (mean of 13 measurements) lower in plants transformed with the T 1275-GUS-nos gene (FIG. 2(B) suggesting the existence of a post-transcriptional regulatory element in the mRNA leader sequence.

Figure 3A:
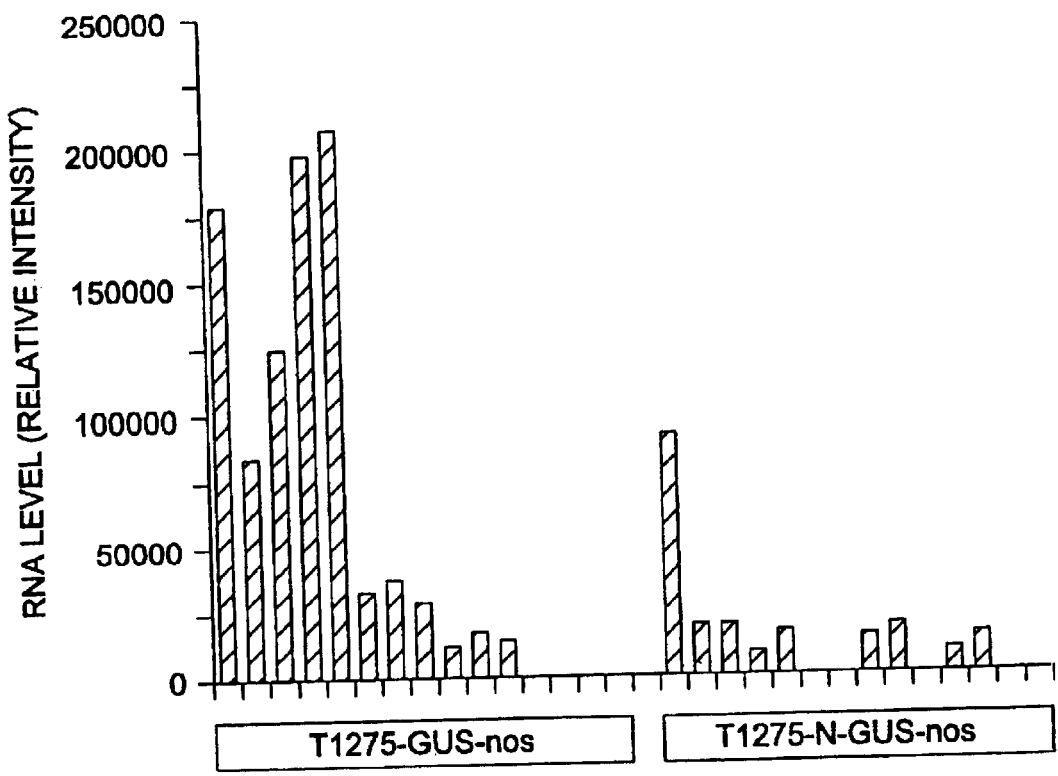
FIG. 3 shows the levels of mRNA, as well as the ratio between GUS specific activity and mRNA levels in leaves of individual, regenerated, greenhouse-grown transgenic plants containing T1275-GUS-nos (i.e. tCUP-GUS-nos), or 35S-GUS-nos constructs, with or without the NdeI-SmaI fragment (see FIG. 7).
Figure 3B:
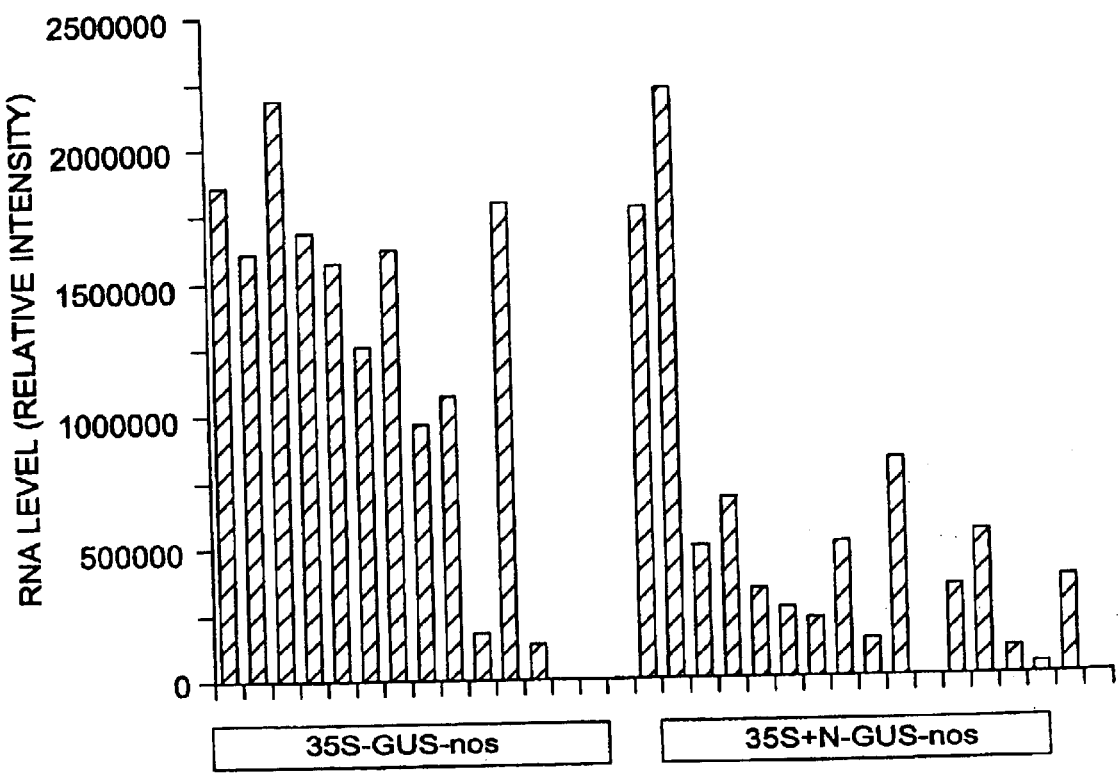
Figure 3C:
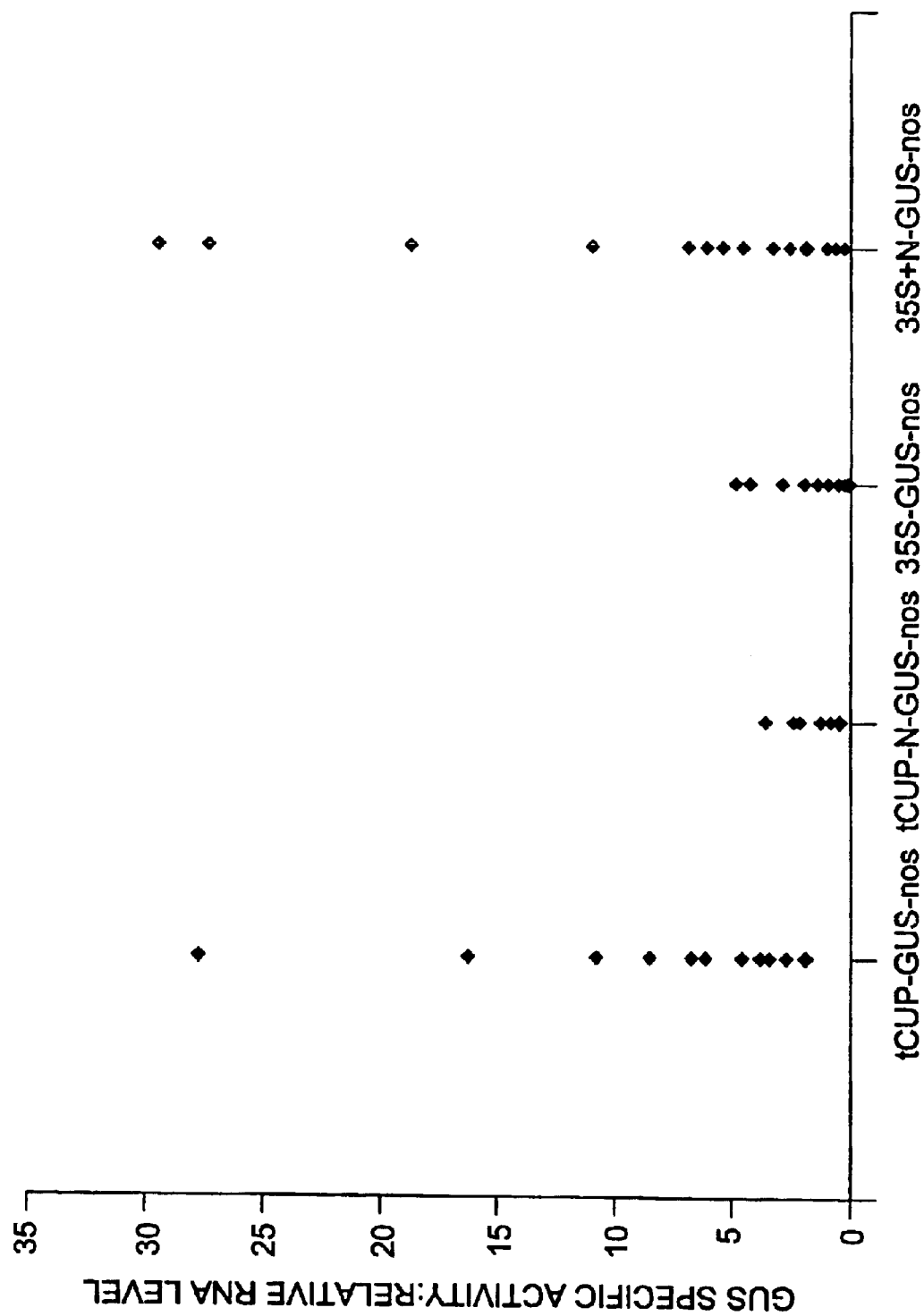

The NdeI-SmaI Fragment Functions as a Transcriptional Enhancer or mRNA Stability Determinant The levels of mRNA were determined in leaves obtained from plants transformed with either T1275-GUS-nos, T1275-N-GUS-nos, 35S-GUS-nos, or 35S+N-GUS-nos (FIGS. 3(A) and (B)). Relative RNA levels were determined by ribonuclease protection assay (Ambion RPAII Kit) in the presence of α-$^{32}$P-CTP labeled in vitro transcribed probe and autoradiographic quantification using Kodak Digital Science 1D Image Analysis Software. Hybridization conditions used during RNase protection assay were overnight at 42–45 degrees in 80% formamide, 100 mM sodium citrate pH 6.4, 300 mM sodium acetate pH 6.4, 1 mM EDTA.

The levels of mRNA examined from transgenic tobacco plants transformed with either T1275-GUS-nos, T1275-N-GUS-nos, 35S-GUS-nos, or 35SN+GUS-nos, were higher in transgenic plants comprising the NdeI-SmaI fragment under the control of the T1275 regulatory element but lower in those under the control of The 35S promoter, than in plants comprising constructs that lack this region (see FIG. 1 for graphical representation of constructs). This indicates that this region functions by either modulating transcriptional rates, or the stability of the transcript, or both.

Deletion of the Nde1-Sma1 fragment (also referred to as "N"; SEQ ID NO:2) from the T1275-GUS-nos gene (T1275-N-GUS-nos; includes nucleotides 2084–2224 of SEQ ID NO:1; see FIG. 1(B) for graphic representation of constructs) resulted in at least about 46-fold reduction in the amount of GUS specific activity that could be detected in leaves of transgenic tobacco cv Delgold (see Table 1). Similar results, of about at least a 40 fold reduction in GUS activity due to the deletion of the Nde1-Sma1 fragment, were observed in transgenic tobacco cv SR1 and transgenic alfalfa (Table 1). Addition of the same fragment (Nde1-Sma1) to a 35S-GUS-nos gene FIG. 1; 35S±N-GUS-nos) construct increased the amount of GUS specific activity by about 5-fold in tobacco, and by a much higher amount in alfalfa (see Table 1).

TABLE 1

GUS specific activity in leaves of greenhouse-grown transgenic tobacco cv Delgold, SR1 and transgenic alfalfa transformed with vectors designed to assess the presence of cryptic regulatory sequences within the transcribed sequence derived from the T1275 GUS gene fusion (see FIG. 1 (B)). Mean ± SE(n).

| Construct | GUS specific activity pmoles MU/min/mg protein | | | |
|---|---|---|---|---|
| | Degold (1) | Delgold (2) | SR1 | Alfalfa |
| T1275-GUS-nos | 557 ± 183 (21) | 493 ± 157 (25) | 805 ± 253 (22) | 187 ± 64 (24) |
| T1275-N-GUS-nos | 12 ± 3 (22) | 12 ± 3 (27) | 6 ± 2 (25) | 4 ± 0.5 (25) |
| 35S-GUS-nos | 1848 ± 692 (15) | 1347 ± 415 (26) | 1383 ± 263 (25) | 17 ± 11 (24) |
| 35S-N-GUS-nos | 6990 ± 3148 (23) | 6624 ± 2791 (26) | 6192 ± 1923 (24) | 1428 ± 601 (24) |

A similar effect was noted in organs tested from transformed tobacco (Table 2), progeny from these plants (Table 2) and alfalfa plants (Table 3)

TABLE 2

Expression of T1275-GUS-nos (+N) compared with T1275-(-N)-GUS-nos (-N), and T1275 (ΔN)-GUS-nos (ΔN; see FIG. 4 (B) and below for constuct details) in organs of transgenic tobacco, and organs of Fl of cv. Delgold and SR1. Mean ± SE (n = 5).

| | GUS specific Activity (pmol MU/min/mg/protein)* | | | | | |
|---|---|---|---|---|---|---|
| | Delgold | | SR1 | | | |
| Organ | +N | -N | +N | -N | +N | ΔN |
| Leaf | 1513 ± 222 | 35 ± 4 | 904 ± 138 | 4 ± 1 | 1252 ± 288 | 10275 ± 3489 |
| Flower | 360 ± 47 | 38 ± 8 | 175 ± 44 | 28 ± 3 | 343 ± 176 | 2821 ± 962 |
| Seed | 402 ± 65 | 69 ± 7 | 370 ± 87 | 33 ± 5 | 337 ± 92 | 3582 ± 976 |
| Leaf (F1) | 1295 ± 801 | 63 ± 14 | 649 ± 313 | 10 ± 5 | 1081 ± 465 | 12430 ± 323 |
| Stem (F1) | 4066 ± 643 | 96 ± 33 | 811 ± 446 | 39 ± 23 | 410 ± 232 | 3555 ± 1801 |
| Root (F1) | 429 ± 172 | 172 ± 77 | 1043 ± 458 | 114 ± 26 | 299 ± 109 | 1396 ± 554 |

*control activity from 4 to 21 pmol MU/min/mg protein

TABLE 3

Expression of T1275-GUS-nos, T1275-(-N)-GUS-nos, 35S-GUS-nos, 35S-GUS(+N)-GUS-nos in organs of transgenic alfalfa. Mean ± SE (n = 5).

GUS Specific Activity (pmol Mu/min/mg protein)

| Construct | Leaf | Petiole | Root (in vitro) | Stem | Flower |
|---|---|---|---|---|---|
| T1275-GUS | 756 ± 73.6 | 1126 ± 72.7 | 745 ± 260 | 1366.7 ± 260 | 456.1 ± 160.9 |
| T1275(-N)GUS | 5.4 ± 1.4 | 7.6 ± 1.2 | 8 ± 2 | 8.1 ± 2.0 | 7.25 ± 1.7 |
| 35S-GUS | 67.5 ± 50.3 | 48.9 ± 23.2 | 57 ± 29 | 56.8 ± 28.7 | 23.2 ± 7.3 |
| 35S(+N)GUS | 5545 ± 2015 | 10791 ± 6194 | 9932 ± 5496 | 9931 ± 5496 | 1039 ± 476.7 |
| Control | 3.7 | 13.2 | 12 | 11.8 | 18.7 |

In transient expression assays using particle bombardment of tobacco leaves, the NdeI-SmaI fragment fused to the minimal −46 35S promoter enhanced basal level of 35S promoter activity by about 80 fold (28.67±2.91 v. 0.33±0.33 relative units; No.blue units/leaf).

A shortened fragment of the NdeI-SmaI fragment (see SEQ ID NO's:3 and 4), referred to as "ΔN", "dN", "deltaN" or "tCUP delta" and lacking the out-of frame upstream ATG at nucleotide 2097–2089 of SEQ ID NO:1, was also constructed and tested in a variety of species. ΔN was created by replacing the NdeI site (FIG. 4(A)) within the leader sequence to a BglII site thereby eliminating the upstream ATG at position 2086 of SEQ ID NO: 1. A Kozak consensus sequence was also constructed at the initiator MET codon and a NcoI site was added to facilitate construction with other coding regions (see FIG. 4(B)). Nucleotides 1–86 of SEQ ID NO:3 (i.e. ΔN with Kozack sequence) are derived from T1275 (nucleotides 2084–2170 of SEQ ID NO: 1). ΔN also includes a Kozack sequence from nucleotides 87 to 97 of SEQ ID NO:3, and nucleotides 98 to 126 of SEQ ID NO:3 comprise the vector sequence between the enhancer fragment and the GUS ATG. The GUS ATG is located at nucleotides 127–129 of SEQ ID NO:3.

Constructs comprising ΔN, for example T1275(ΔN)-GUS-nos, when introduced into tobacco yielded from 8 to 11 fold greater levels of GUS activity in leaves, flower s, seeds and roots of transgenic tobacco compared to plants expressing T1275-GUS-nos (Table 2). This increase was also observed in progeny of The transformed plants (Table 2)

Activity of NdeI-Sma1, N, and ΔN in other Species

Monocots

Figure 4B:
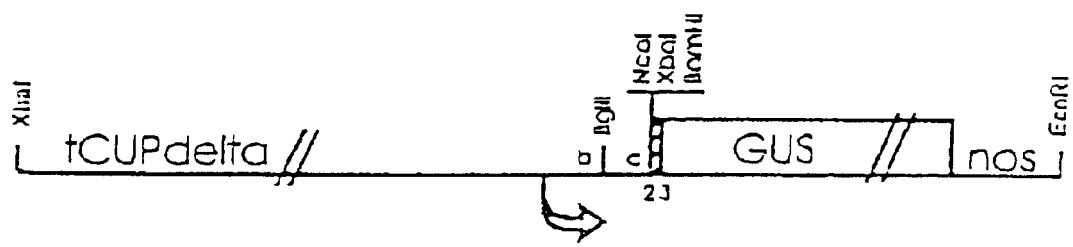
FIG. 4 shows the maps of T1275-GUS-nos and T1275 (ΔN)-GUS-nos.
Figure 5A:
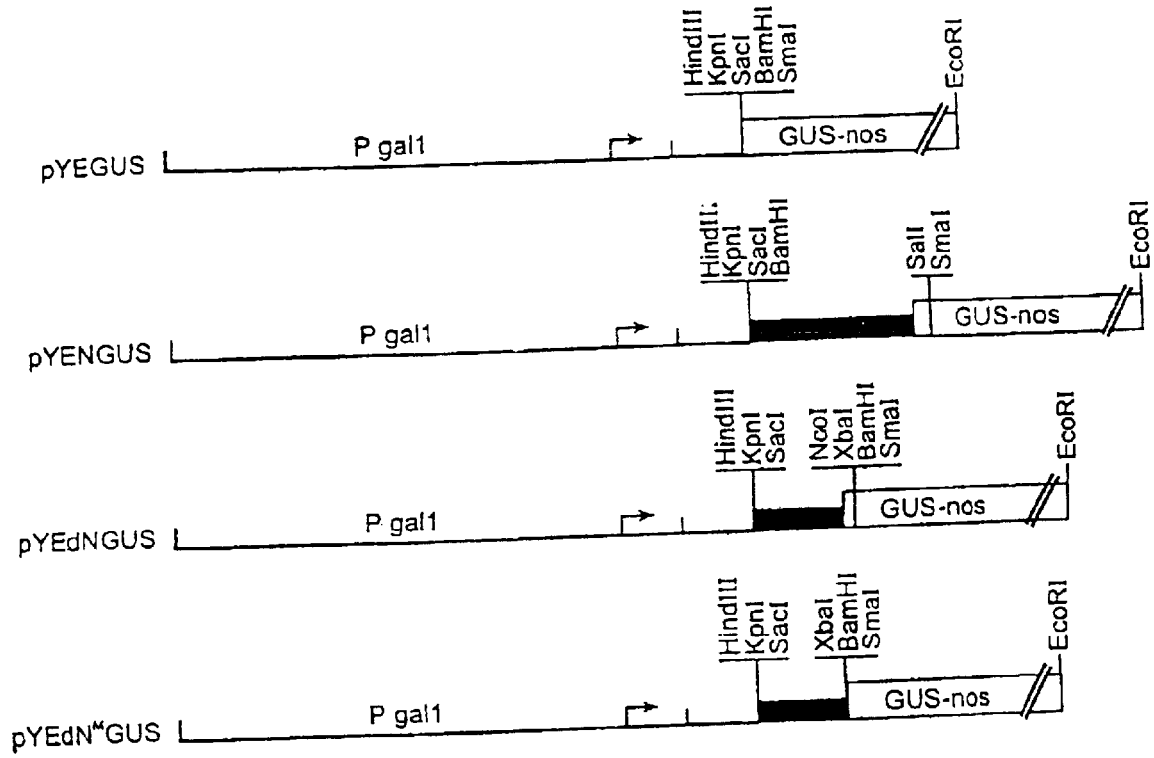
FIG. 5(A) shows constructs used for yeast expression: pYES-GUS-nos (also referred to as pYEGUS); pYES(+N)-GUS-nos (also referred to as pYENGUS); pYES(ΔN)-GUS-nos (also referred to as pYEdNGUS) and pYES(ΔN$^M$)-GUS-nos (also referred to as pYEdN$^M$GUS), which lacks the Kozak consensus sequence.
Figure 5B:
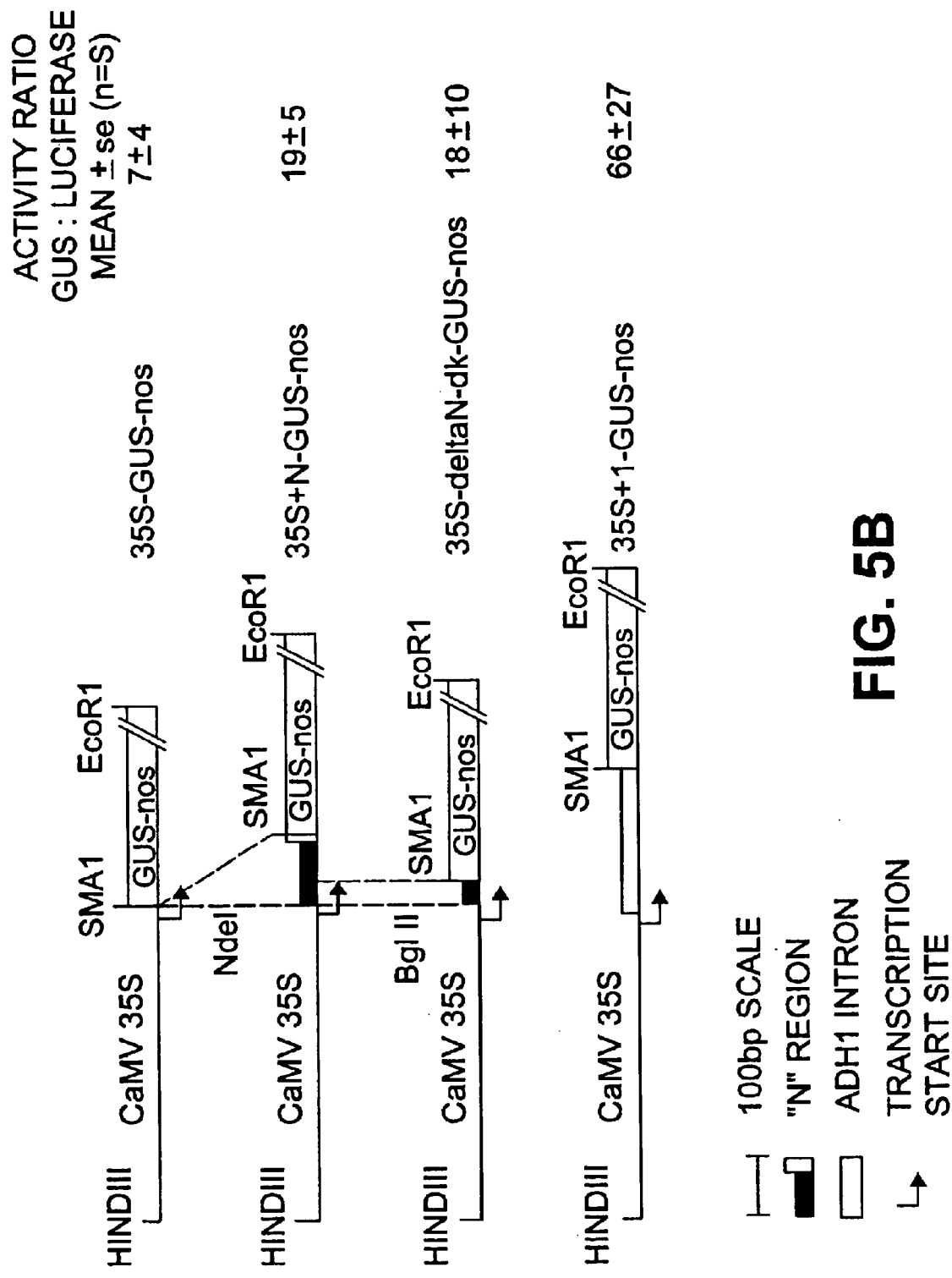
FIG. 5(B) shows constructs used for the transient expression via particle bombardment of corn callus. Maps for 35S-GUTS-nos, 35S (+N-GUS-nos, 35S (ΔN)-GUS-nos and 35S(+i)-GUS-nos are presented indicating the "N" region, ADH1 intron, and the arrow indicates the transcriptional start site. Note that 35S(ΔN)-GUS-nos is referred to as 35S+deltaN-dK-GUS-nos. Also shown are the associated activities of the constructs in the callus expressed as a ratio of GUS to luciferase (control) activity.

In monocots, transient expression in corn callus indicated that the NdeI-SmaI fragment (SEQ ID NO:2), or a shortened NdeI-SmaI fragment, ΔN (SEQ ID NO:3; see FIG. 4(B) and above for construct details), significantly increases GUS expression driven by the 35 S promoter, but not to the higher level of expression generated in the presence of the ADH1 intron ("i"; FIG. 5(B) and Table 4).

TABLE 4

Transient expression analysis of GUS activity in bombarded corn calli. Luciferase activity was used to normalize the data. Mean ± se (n = 5)

| Construct | Ratio GUS:Luciferase activity |
|---|---|
| 35S GUS-nos | 7.4 ± 4 |
| 35S(+N)-GUS-nos | 19 ± 5 |

TABLE 4-continued

Transient expression analysis of GUS activity in bombarded corn calli. Luciferase activity was used to normalize the data. Mean ± se (n = 5)

| Construct | Ratio GUS:Luciferase activity |
|---|---|
| 35S(ΔN)-GUS-nos | 18 ± 10 |
| 35S-i-GUS-nos | 66 ± 27 |

White Spruce

Figure 5C:
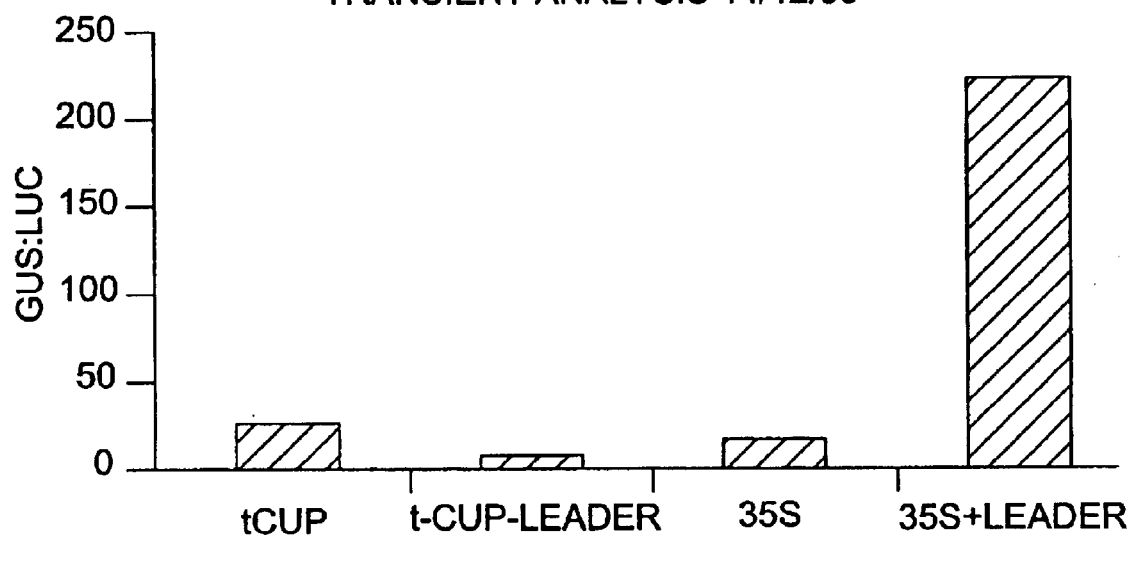
FIG. 5(C) shows the ratio of reporter gene activity (GUS) to control (LUC) in white spruce cells transformed with full length tCUP (tCUP; tCUP-GUS-nos), tCUP lacking the NdeI-SmaI region (tCUP-leader; tCUP-(-N)-GUS-nos), 35S (35S; 35S-GUS-nos), and 35S with the NdeI-SmaI fragment (35S+leader; 35S+N-GUS-nos)

The functionality of the NdeI-SmaI fragment (SEQ ID NO:2) was also determined in non-angiosperm species. In conifers, for example white spruce, transient bombardment of cell culture exhibited an increase in expression (Table 5). Similar results were obtained when the same constructs were analyzed compared to luciferase (control) activity (FIG. 5(C)).

TABLE 5

Expression of T1275-GUS-nos, T1275(-N)-GUS-nos, 35S-GUS-nos, 35S(+N)-GUS-nos in white spruce embryonal masses following bombardment (n = 3).

| Construct | Average GUS expression per leaf (Number of blue spots) |
|---|---|
| T1275-GUS-nos | 72.67 ± 9.33 |
| T1275(-N)-GUS-nos | 21.33 ± 4.49 |
| 35S-GUS-nos | 113.67 ± 17.32 |
| 35S(+N)-GUS-nos | 126.33 ± 19.41* |

*average spot much greater in size and strength.

Yeast

In yeast, the presence of the NdeI-SmaI fragment (SEQ ID NO:2) or ΔN (SEQ DI NO:3) exhibited strong increase in expression of the marker gene.

Yeast-*E.coli* shuttle vector pYES2 is a multi-copy plasmid. It carries the inducible promoter $P_{gall}$. In culture containing glucose, $P_{gall}$ is inhibited. However, when galactose is used as carbon source, $P_{gall}$ is turned on. There is no reporter gene in pYES2, therefore the GUS reporter gene was inserted into pYES2, to produce plasmid, pYEGUS. It contains cloning sites between the transcription start of $P_{gall}$, and the reporter gene GUS to facilitate the incorporation of various versions of N into this reporter system. A series of constructs comprising a galactose inducible promoter $P_{gall}$, various forms of the NdeI-SmaI fragment, and GUS (UidA) were made within the yeast plasmid pYES2 (see FIG. 5(A):

| Name | Version of "N" |
|---|---|
| pYES2 | no |
| pYEGUS | no (control) |
| pYENGUS | full length Nde1-Sma1 fragment, N |
| pYEdNGUS (or pYEΔNGUS) | delta N with Kozak |
| pYEdN^MGUS (or pYEΔN^MGUS) | delta N without Kozak |

All of these constructs are based on a yeast plasmid, pYES2, which contains a galactose-inducible promoter $P_{gal1}$. There is no reporter gene in the plasmid. All the new constructs contain the reporter gene UidA along with different versions of N.

Nucleotides 1–86 of SEQ ID NO:4 ($\Delta N^M$) comprise a portion of a regulatory region obtained from T1275 (derived from nucleotide 2084–2170 of SEQ ID NO:1), while nucleotides 87–116 comprise a vector sequence between the enhancer fragment and the GUS ATG which is located at nucleotides 117–119 of SEQ ID NO:4.

These constructs were tested in yeast strain INVSC1 using known transformation protocols (Agatep R. et al. 1998, http://www.biomednet.com/db/tto). The yeast were grown in non-inducible medium comprising raffinose as a carbon source for 48 hr at 30° C. and then transferred onto inducible medium (galactose as a carbon source). The GUS activity was determined by using the x-gluc system and intact yeast cells. Yeast cells were harvested after 4 hr post induction and GUS activity determined quantitatively. Up to about a 12 fold increase in activity was observed with constructs comprising ΔN. Constructs comprising $\Delta N^M$ exhibited even higher levels of reporter activity (Table 6). The results indicate that the Nde1-Sma1 fragment (SEQ ID NO:2), ΔN (SEQ ID NO:3) and $\Delta N^M$ (SEQ ID NO:4) are functional in yeast (Table 6).

TABLE 6

Expression of pYEGUS, pYENGUS, pYEdNGUS, and pYEdN^MGUS (ΔN, without a Kozak consensus sequence) in transformed yeast (n = 5).

| | Expt. 1 | | Expt. 2 | |
|---|---|---|---|---|
| Construct | Activity | Fold over pYEGUS | Activity | Fold over pYEGUS |
| pYES-GUS-nos | 93 ± 15 | 1 | 407 ± 8 | 1 |
| pYES(+N)-GUS-nos | 753 ± 86 | 8 | 1771 ± 191 | 4 |
| pYES(ΔN)-GUS-nos | 1119 ± 85 | 12 | 2129 ± 166 | 5 |
| pYES(ΔN^M)-GUS-nos | 1731 ± 45 | 19 | 6897 ± 536 | 17 |

Insect

Figure 11A:
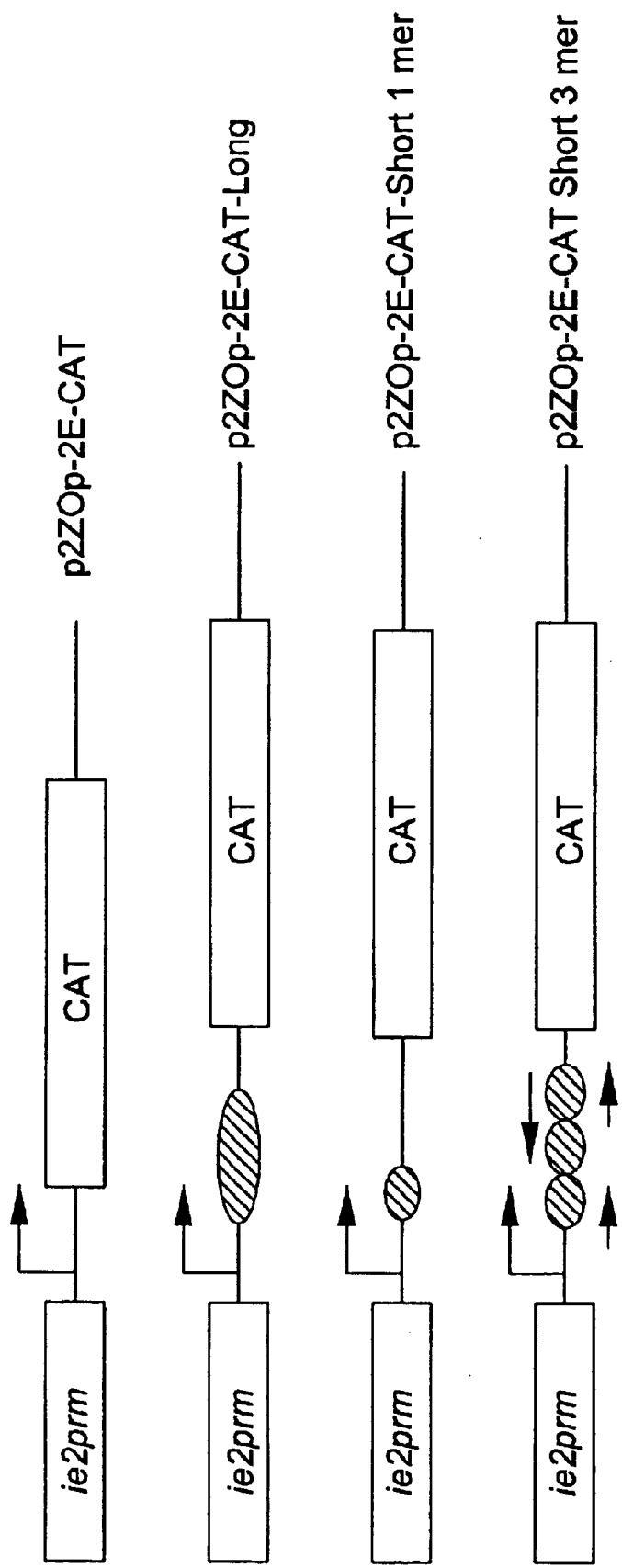
FIG. 11 shows N, and fragments and derivatives of N, and their associated activities in an insect cell expression system.
FIG. 11(B) shows the activity of the constructs in the insect cell culture system is expressed relative to p2ZOp-2E-CAT (control).
Figure 11B:
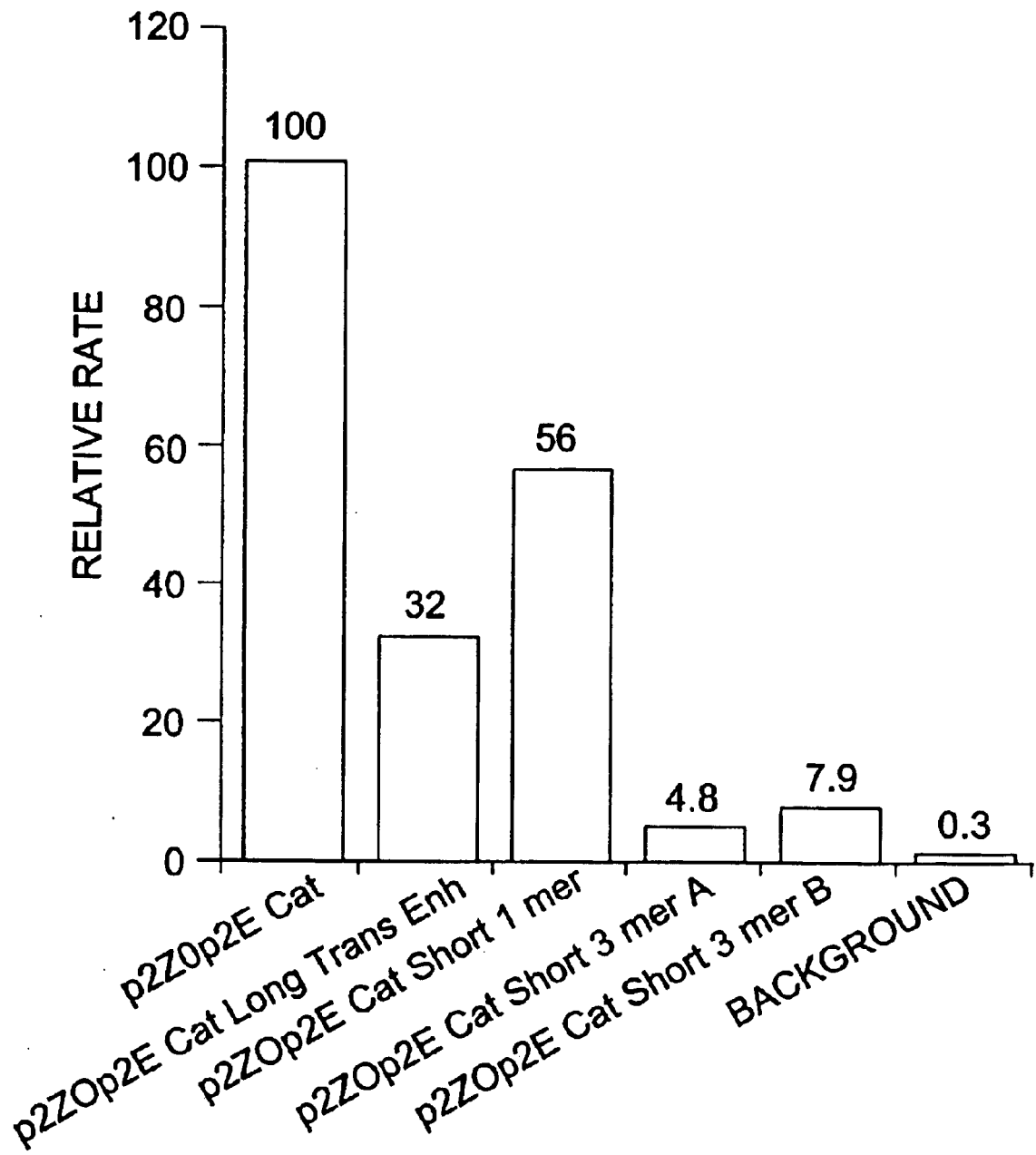

Constructs containing $\Delta N^M$ (i.e. ΔN lacking the Kozack sequence; SEQ ID NO:4; see FIG. 11) were also tested in insect cells. These constructs comprised the insect virus promoter ie2 (Theilmann D. A and Stewart S., 1992, Virology 187: pp. 84–96) in the present or absence of $\Delta N^M$ and CAT (chloramphenicol acetyl-transferase) as the reporter gene. The insect line, Ld652Y, derived from gypsy moth (*Lymantria dispar*) was transiently transformed with the above constructs using liposomes (Campbell M. J. 1995, Biotechniques 18: pp. 1027–1032; Forsythe I. J. et al. 1998, Virology 252: pp. 65–81). Cells were harvested 48 hours after transformation and CAT activity quantitatively measured using titiated acetyl-CoA (Leahy P. et al. 1995 Biotechniques 19: pp. 894–898). The presence of the $dN^m$ fragment was found to reduce the activity of the insect promoter-reporter gene construct by three fold in insect cells. This suggests that $dN^m$ can function as a translation repressor in insect cells.

The activity of L2 and an oligomer of L2 (3×L2, referred to as Short 3 mer) was tested in insect cells, as described above, using constructs illustrated in FIG. 11 (top panel). The results (FIG. 11, bottom panel) show that L2 has an inhibitory effect on level of activity when compared with the reference construct, p2Zop-2E-CAT. The inhibitory effect is much stronger when the fragment 3×L2 is used in the construct.

The NdeI-SmaI Fragment Functions as a Translational Enhancer

Analysis were performed in order to determine whether the NdeI-SmaI region functions post-transcriptionally. The GUS specific activity:relative RNA level was determined from the GUS specific activity measurements, and relative RNA levels in greenhouse grown transgenic plants (FIG. 3(C)). The ratio of GUS specific activity to relative RNA level in individual transgenic tobacco plants comprising the NdeI-SmaI fragment is higher than in plants that do not comprise this region (FIG. 3(C)). Similar results are obtained when the data are averaged, indicating an eight fold reduction in GUS activity per RNA. Similarly, an increase, by an average of six fold, in GUS specific activity is observed when the NdeI-SmaI region is added within the 35S untranslated region (FIG. 3(C)). The GUS specific activity:relative RNA levels are similar in constructs containing the NdeI-SmaI fragment (T1275-GUS-nos and 35SN-GUS-nos). These results indicate that the NdeI-SmaI fragment (SEQ ID NO:2) modulates gene expression post-transcriptionally.

Further experiments, involving in vitro translation, suggest that this region is a novel translational enhancer. For these experiments, fragments, from approximately 3' of the transcriptional start site to the end of the terminator, were excised from the constructs depicted in FIG. 1 using appropriate restriction endonucleases and ligated to pGEM4Z at an approximately similar distance from the transcriptional start site used by the prokaryotic T7 RNA polymerase. Another construct containing the AMV enhancer in the 5' UTR of a GUS-nos fusion was similarly prepared. This AMV-GUS-nos construct was created by restriction endonuclease digestion of an AMV-GUS-nos fusion, with BglII and EcoRI, from pBI525 (Datla et al., 1993, Plant Science 94: 139–149) and ligation with pGEM4Z (Promega) digested with BamHI and EcoRI. Transcripts were prepared in vitro in the presence of $m^7G(5')$ ppp(5')G Cap Analog (Ambion). Transcripts were translated in vitro in Wheat Germ Extract (Promega) in the presence of 35S-Methionine and fold enhancement calculated from TCA precipitable cpms.

Translation of transcripts in vitro demonstrate an increase in translational efficiency of RNA containing the NdeI to SmaI fragment (see Table 7).

TABLE 7

In vitro translation of mRNA obtained from transgenic tobacco plants transformed with vectors with or without a NdeI-SmaI fragment obtained from the T1275 GUS gene fusion (see FIG. 7) using wheat germ extract.

| in vitro transcript | in vitro translation fold enhancement |
|---|---|
| T1275-GUS-nos | 3.7 |
| T1275-N-GUS-nos | 1 |
| AMV-GUS-nos | 1.9 |

The levels of protein produced using mRNAs comprising the NdeI-SmaI fragment are also greater than those produced using the knot translational enhancer of Alfalfa Mosaic Virus RNA4 (Jobling S. A. and Gehrke L. 1987, Nature, vol 325 pp. 622–625; Datla R. S. S. et al. 1993 Plant Sci. vol 94, pp. 139–149). These results indicate that this region functions post-transcriptionally, as a translational enhancer.

Characterization of the Translational Regulatory Element "$\Delta N^M$" in yeast Based on sequence of dNm ($\Delta N^M$) 5 linkers were designed and synthesized using standard protocols (FIGS. 6(A) and (B); SEQ ID NO's: 5–9). The linkers were cloned into the Acc65I/BamHI sites of pYEGUS to produce plasmids: pYEL1GUS, pYEL2GUS, pYEL3GUS, pYEL4GUS, and pYEL5GUS, comprising L1–L5,respectively (FIG. 6(I)). The GUS activity was determined using methods mentioned above (Yeast).

Of the five fragments, L2 (SEQ ID NO:6) enhanced the expression of GUS approximately 13 fold over the level in pYEGUS, and 3–4 fold over the level of pYENGUS which contains the fragment NdeI-SmaI. The fragments L1,L4 and L5 (SEQ ID NO's:5, 8 and 9 respectively) showed marginal enhancement by about 2 fold, while L3 (SEQ ID NO:7) exerted an inhibition function (FIG. 6(C)).

Characterization of L2

Two linkers based on L2 were designed comprising nucleotides 1–16 of SEQ ID NO:6 (L2C), and nucleotides 10–24 of SEQ ID NO:6 (L2R; FIG. 6(D)). The resulting plasmids were designated pYEL2CGUS and pYEL2RGUS, respectively. Determination of the GUS activity of yeast cells transformed with these two plasmids showed that both L2C and L2R increased GUS activity over control constructs lacking any translational regulatory element, and that they retained partial activity of L2 (FIG. 6(E)). However, these fragments exhibited less activity than the full length L2 sequence.

A linker called LM was designed. LM (plasmid: pYELMGUS) contains the overlapping region of L2C and L2R (ACUCUCU). pYELMGUS did not show significant GUS activity enhancement in comparison with pYEGUS (data not shown).

Modifications of L2

Scanning mutation strategy was used to determine which bases in L2 are crucial to its activity. Seven linkers (SCAN1–SCAN7) were designed based on L2 Each of these modified, or analog L2 fragments, contains one tri-base mutation as indicated in bold in FIG. 6(F). Constructs were prepared comprising one of each of the 7 mutant sequences (pYESCAN1GUS-pYESCAN7GUS). GUS activity determination showed that when compared to pYEGUS, the addition of SCAN1, SCAN2, SCAN4, SCAN5 or SCAN6 to this base construct increased protein expression from about 2 to about 10 fold (FIG. 6(G)). Constructs comprising pYESCAN3GUS and pYESCAN7GUS did not exhibit any increase in protein expression (FIG. 6(G)). These results indicate that analogs of L2 also exhibit translational enhancer activity.

Two constructs were prepared comprising sequences from RENT family members which were homologous, but not identical, to L2 (FIG. 6(I); pYEB1-L2GUS and pYEB7-L2GUS). GUS activity assays showed that these constructs had GUS activity above the control construct pYEGUS, however activity was much higher in pYEL2GUS, the construct containing L2 (FIG. 6(K)). Each of these two constructs (pYB1-L2GUS and pYEB7-L2GUS) contained two mutations when compare d with L2 (see FIG. 6(I)), including a mutation in each one of the nucleotide triplets identified as critical by the scanning mutation experiment. To further evaluate the importance of the two nucleotide triplets in the function of L2, additional constructs were prepared containing derivatives of L2 where one or both critical nucleotide triplets were deleted (FIG. 6 (I); pYEL2D1, pYEL2D2 and pYEL2D3). Deletion of either one or both nucleotide triplets reduced the level of GUS expression significantly when compared to expression produced by pYEL2GUS, however the GUS activity was above the level of expression from the control construct pYEGUS as well as the constructs pYESCAN3GUS and pYESCAN7GUS (FIG. 6(J)).

The effect of the oligomerisation of L2 was tested by introducing a derivative fragment containing twice the sequence of L2 into pYEGUS (FIG. 6(I); pYE2L2GUS). The enhancement factor was increased by about 20% between pYEL2GUS and pYE2L2GUS (FIG. 6(L)). The effect of the position of L2 in relation to the 5' end of the mRNA was also tested by preparing constructs where the fragment L2 was progressively shortened with respect to the transcript start site (FIG. 6(N); pYE330L2GUS, pYE373L2GUS, pYE349L2GUS and pYE400L2GUS, which correspond to 330, 373, 349 and 400, respectively, in FIG. 6(O)). As shown in FIG. 6(O), an increase in the level of GUS activity was observed at all positions tested, when compared with the reference construct pYEGUS, with a substantial increase in activity observed using pYE349 L2GUS.

Activity of L2 in Other Expression Systems

Figure 6M:
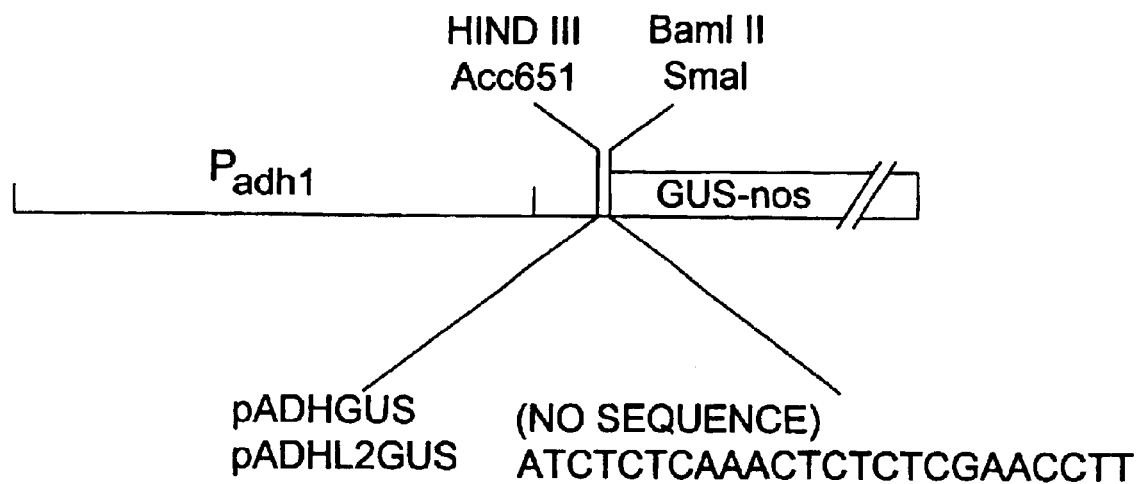

In order to determine if L2 functions in an expression system other than the $P_{gal1}$ system, a new series of constructs were made (FIG. 6(M)). The $P_{gal1}$ promoter was replaced by the constitutive promoter $P_{gal1}$, in the plasmids. Comparison of pADHGUS and pADHL2 GUS yeast showed that L2 functions in the constitutive system (FIGS. 6 (E) and (H)).

In order to verify that L2's activity in not based on changing the mRNA level of reporter gene, RNA levels in yeast harbouring the L2 construct was determined. Yeast were grown in SC/glucose medium at 30° C. overnight (OD600 is about 2). Then the cells were transferred to SC/galactose medium for 1 hr. at 30° C. to induce the expression of the GUS reporter gene. Total RNA was extracted from the cells and analysized by RNA hybridization. The hybridization signals were quantitatively determined by liquid scintillation counting. The yeast stain carrying pYEL2GUS plasmid did not produce higher level of GUS mRNA than the other control strains (data not shown).

In order to determine if L2 functions through translation enhancement or by increasing mRNA stability, the rate of disappearance of GUS mRNA containing L2 was compared to GUS mRNA containing no translation enhancer element (FIG. 6(P)). Yeast cell lines were grown and induced as described above. After a 1 hr induction, the cells were transferred back to SC/glucose medium and sampled at the intervals indicated. Total RNA was extracted, hybridized and quantified as described above. The results show that the GUS mRNA produced by pEYL2GUS was equally to slightly less stable than the GUS mRNA produced by pYEGUS. This shows that the increased activity observed in presence of L2 is not due to an increase in stability of the mRNA containing L2.

Tobacco Transient Leaf Assay

To determine the effect of the fragments L1 to L5 in plant systems, constructs containing these fragments linked to the promoter tCUP2 (also referred to as EnhtCUP2; FIG. 7(A) .1). With reference to FIG. 7(A).1:

tCUP1 comprises the tCUP regulatory region to position −394 (from the translational start site), and dN′′′ (SEQ ID NO:4; ΔN′′′ lacking a Kozak sequence);

tCUP2 comprises the tCUP regulatory region to position −394 (from The translational start site), dN′′′ (SEQ ID NO:4; ΔN′′′ lacking a Kozak, sequence) and includes a TATA sequence inserted at position −30 (from the translational start site);

tCUP3 comprises the tCUP regulatory region to position −394 (from the translational start site). dN′′′ (SEQ ID NO.:4; ΔN′′′ lacking a Kozak sequence),a TATA sequence inserted at position −30 (from the translational start site), and a concatamer of direct repeats of the −62 to −394 (determined from the translational start site) fragment, repeated three times.

Constructs comprising tCUP linked with GUS were prepared (FIG. 7(A).2, pUCtCUP2L1GUS to pUCtCUP2L5GUS; referred to as "L1"-"L5" in FIG. 7(B)) and bombarded onto tobacco leaf disks. The construct pUCEntCUP2GUS, which contains the fragment dN′′′ and the construct pUCtCUP2(−N) which does not contains the fragment dN′′′ (referred to a "−N" in FIG. 7(B)) were also included in the comparison.

The first pair of leaves from 2–3 weeks-old tobacco (*Nicotiana tobaccum* L. var. SR1) plants was harvested, surface sterilized and cut into 1.5 cm2 segments. The leaf segments were placed on a medium consisting of MS salts, B5 vitamins (Gamborg, O. L., Miller, R. A. and Ojima, K (1968). J. Exp. Res. 50:151–158), 3% sucrose and 0.25% Gelrite (Sigma, USA) in a 20×15 mm Petri dishes as a preparation for bombardment. Plasmid DNA was isolated using the QIAGEN Midi kit and the plasmid DNA was delivered into tobacco leaves using BioRad particle Gun as per manufacturers recommendations. GUS gene expression was determined by fluorometric assays 36 hours after bombardment (Jefferson, R. (1988). *Plant reporter genes: the GUS gene fusion system.* in Genetic Engineering: Principles and Methods (Setlow, J. K. and Hollaender, A., eds). New York: Plenum Press, pp. 247–263). GUS activity was measured as pmol 4-methylumbelliferone per mg protein per min.

The results (FIG. 7(B)) show that L2 is the most active of the five fragments (L1–L5) compared, while L3 and L5 also produce a significant increase in the level of expression of the reference construct "−N" (pUCtCUP2(−N)). However none of those fragments is as efficient as dN′′′ (in pUCentCUP2GUS) at increasing the level of GUS activity.

Alfalfa Transient Cell Culture Assay

The activity of the fragments L1 to L5 was also rested by bombardment in an alfalfa cell suspension culture to evaluate the range of species where translation enhancement is observed and the variation between species. The constructs described in FIG. 7(A).2 were used (pUCtCUP2L1GUS to pUCtCUP2L5GUS; referred to as "tCUP2-L1"-"tCUP2-L5" in FIG. 7(C)). The construct pUCEntCUP2GUS, which contains the fragment dN′′′, and the construct pUCtCUP2(−N,) which does not contains the fragment dN′′′ (referred to a "tCUP2" and "tCUP2-N", respectively, in FIG. 7(B)), were also included in the comparison.

Alfalfa (*Medicago sativa* L.) c.v. Rangelander, clone N4.4.2, was used in the experiments to produce the cell suspension. Donor plants were propagated in vitro by subculturing individual nodes in 75 ml Schenk and Hildebrandt (1972, Car. J. Bot. 50–199–204) medium modified to contain 29.2 mM sucrose, 0.1 mM indole-3-acetic acid, 0.1 mM iso-pentyl adenine, 1% Bactoagar (Difco), pH 5.9, in 10-cm Magenta containers (Magenta Corp., Chicago). Petioles of in vitro-propagated plants were cut to 8–10 mm in length and transferred onto B5h medium. B5h medium consisted of B5 medium (Gamborg, O. L., Miller, R. A. and Ojima, K. 1968. Exp. Cell Res. 50:151–158), 5.1 mM $CaCl_2 2H_2O$, 87.6 mM sucrose, 5.5 mM glutamine, 32.5 mM glutathione, 95.1 mM serine, 7.4 mM adenine, 4.5 mM 2,4-dichlorophenoxyacetic acid, 0.9 mM kinetin, 9 gl$^{-1}$ Bactoagar (Difco) at pH 5.5. Twenty days after introducing the petioles into culture on B5h medium, callus developed were transferred into liquid 135 medium modified to contain 4.5 mM 2,4-D, 0.5 mM naphthalene acetic acid, and 58.4 nm sucrose (B5mod) for proliferation. One and one half to two grams of tissue was cultured in a 125 ml flask containing 40 ml of medium. The suspension culture was shaken on an orbital shaker at 130 RPM. Tissue was subcultured every 7 to 10 days. For subculture, ten milliliters of suspension cultures were transferred to fresh B5mod medium. All the cultures were maintained at 25° C. under a 16-hr photoperiod of fluorescent Sylvania "Cool White" light with a Photosynthetic Photon Flux of about 50 mmol m$^{-2}$S$^{-1}$.

For bombardment the suspension cultures, 5–7 days after subculture, were collected to a filter paper and the culture with the filter paper was then transferred to B5 medium plus 0.2 M sorbitol and 0.2 M mannitol. The cultures were maintained on this medium overnight. Plasmid DNA was isolated using Qiagen Plasmid Kits and the concentration was adjusted to 1 mg/ml. DNA was coated on to 1.3 mm tungsten particles as described by Brown et al. (Brown, D.C. W., Tian, L.-N., Buckley, D. J., Lefebvre, M., McGrath, A. and Webb, J. 1994. Plant Cell Tiss. Org. Cult. 37: 47–54). DNA was delivered into tissues using a modified Particle Inflow Gun (Brown et al. 1994). Tissues were bombarded once using 150 psi al a distance of 10 cm. A piece of 500 mm mesh was placed above the Petri dish for a better particle distribution and preventing tissue splash. The bombarded culture was maintained in the same medium in the dark for about 36 hrs. A minimum of three plates was bombarded for each construct.

Transient GUS gene expression was determined by a histochemical assay (Jefferson, R. 1988 Plant reporter genes: the GUS gene fusion system. Pages 247–263 in J. K. Setlow, ed. Genetic Engineering: Principles and Methods, Vol. 10 New York, Plenum Press) and by recording the number of GUS reporter gene expression events as indicated by the number of blue foci per explant or Petri dish.

Figure 7C:
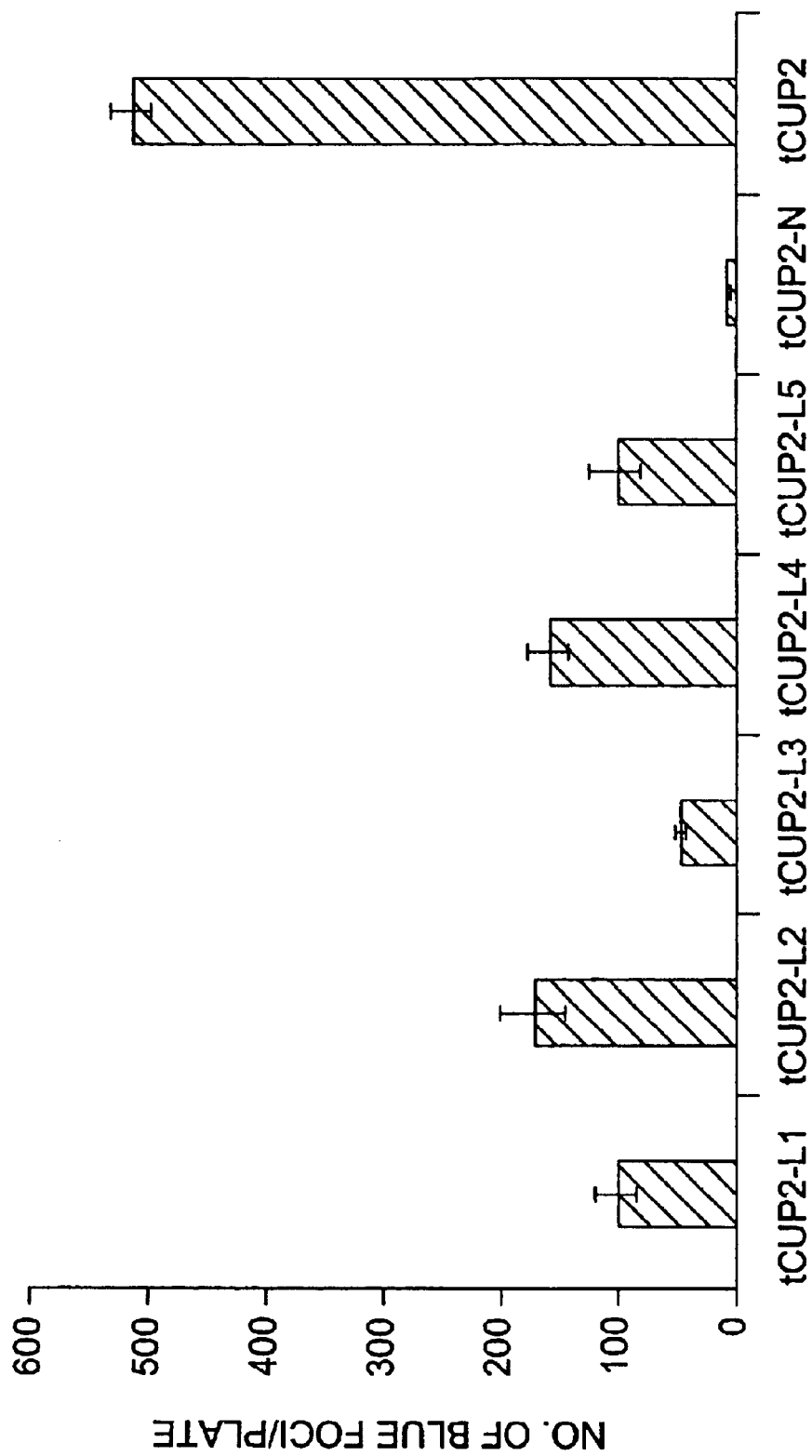
FIG. 7(C) shows the relative activity of several constructs within an alfalfa transient assay using a cell suspension culture. The activity of the constructs in the bombarded cell layer is expressed as the number of blue foci per plate. tCUP-L1 to L5 comprise enhanced tCUP2 regulatory element linked with L1 (tCUP2-L1-GUS-nos), L2 (tCUP2-L2-GUS-nos), L3 (tCUP2-L3-GUS-nos), L4 (tCUP2-L4-GUS-nos), or L5 (tCUP2-L5-GUS-nos) respectively; tCUP2 (also referred to as entCUP2) comprises tCUP2-GUS-nos; tCUP2-N comprises tCUP2 with the N fragment removed ( tCUP2 (–N) ).

The results show (FIG. 7(C)) that L2 produces the strongest enhancement among the fragments tested and that L1, L4 and L5 (tCUP2-L1 to tCUP2-L5) also significatively increase the level of activity of the reference construct, tCUP2-N (pUCtCUP2(−N)GUS). However none of the fragments produce by itself an increase of activity as high as dN′′′ (tCUP2; pUCtCUP2GUS).

Spruce Transient Callus Assay

The activity of the fragments L1 to L5 were also tested by bombardment in a white spruce callus expression system to determine activity in conifer trees. The constructs described in FIG. 7(A).2 were used (pUCtCUP2L1GUS to pUCtCUP2L5GUS; referred to as "tCUP2L1"-"tCUP2-L5" in FIG. 7(D)). The construct pUCEntCUP2GUS, which contains the fragment dN′′′, and the construct pUCtCUP2(−N) which does not contains the fragment dN′′′ (referred to a "tCUP2" and "tCUP2-N", respectively, in FIG. 7(B)), were also included in the comparison.

Embryonal tissues of white spruce were maintained by subculturing on half-strength LM medium (Lirvay, B. I, Verna, D.C., Johnson, M. A. 1985. Plant Cell Rep 4: 325–328) containing 10 mM 2,4-D (2,4-Dichlorophenoxyacetic acid) and 5 mM BAP (6-Benzyl-amino-purine). All the cultures were subcultured every 10 to 14 days and maintained in the dark. For bombardment, 0.4 gram of tissues, 3–5 days after subculture, were placed in a thin layer on a sterile filter paper (5.5 cm) which was placed in a Petri dish (9×1.5 cm) 1/2LM medium. Plasmid DNA was isolated using Qiagen Plasmid Kits and the concentration was adjusted to 1 mg/ml. DNA was coated on to 1.3 mm tungsten particles as described by Brown et al. (Brown, D.C. W., Tian, L. -N., Buckley, D. J., Lefebvre, M., McGrath, A. and Webb, J. 1994. Plant Cell Tiss. Org. Cult. 37: 47–54.). DNA was delivered into tissues using a modified Particle Inflow Gun (Brown et al. (1994). Tissues were bombarded once using 150 psi at a distance of 10 cm. A piece of 500 mm mesh was placed above the Petri dish for a better particle distribution and preventing tissue splash. The bombarded culture was returned to the ½ LM medium and maintained in the dark for about 36 hrs. A minimum of three plates was bombarded for each constructs. Transient GUS gene expression was determined by a histochemical assay (Jefferson, R. 1988, supra) and by recording the number of GUS reporter gene expression events as indicated by the number of blue foci per explant or Petri dish.

Figure 7D:
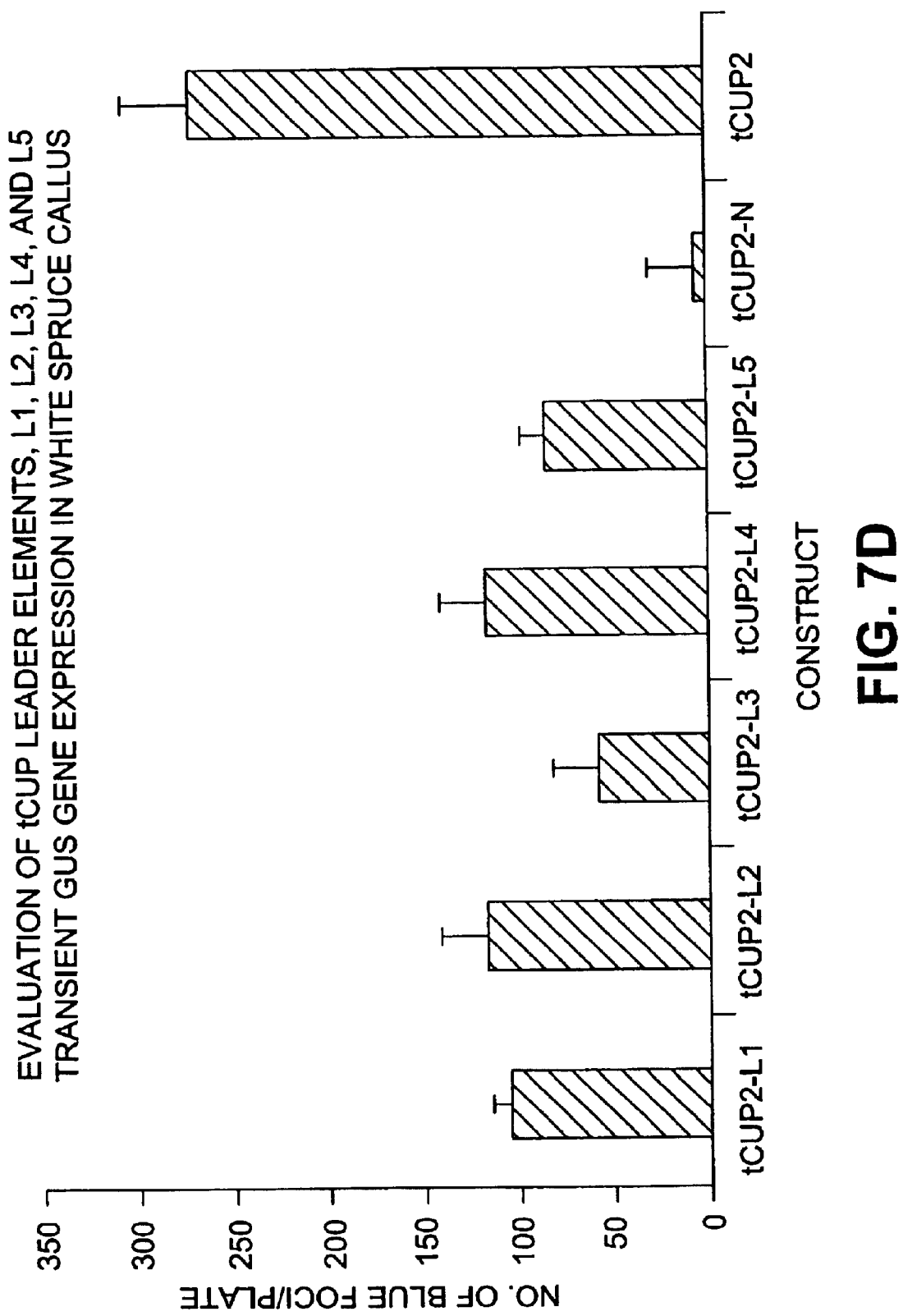
FIG. 7(D) shows the evaluation of the expression of tCUP leader elements with the enhanced tCUP2 regulatory element in a transient GUS gene expression system in white spruce callus. Activity is expressed as the number of blue foci per plate. tCUP2-L1, tCUP2-L2, tCUP2-L3, tCUP2-L4 and tCUP2-L5 comprise enhanced tCUP2 regulatory element linked with L1 (tCUP2-L1-GUS-nos), Le2 (tCUP2-L2-GUS-nos), L3 (tCUP2-L3-GUS-nos), L4 (tCUP2-L4-GUS-nos), or L5 (tCUP2-L5-GUS-nos) respectively; tCUP2 (also referred to as EntCUP2 or EnhtCUP2) comprises tCUP2-GUS-nos; tCUP2-N (also referred to as –N) comprises tCUP2 with the N fragment removed (tCUP2 (–N)).

The results show (FIG. 7(D)) that L2 and L4 produce the strongest enhancement among the fragments tested and that L1, L3 and L5 also significatively increase the level of activity of the reference construct, pUCtCUP2(-N)GUS. However none of the fragments produce by itself an increase of activity as high as in tCUP2 (dN$^m$ in pUCtCUP2GUS).

Collectively, the results indicate that L2 is the most active of the fragments L1 to L5 in tobacco, alfalfa, and white spruce. The results also show that the four other fragments have translation enhancing activity, however that activity is more species dependant. For example, L3 and L5 have significative enhancing activity in the tobacco assay, and L1 and L4 have significative enhancing activity in white spruce.

Transgenic Arabidopsis Plants

The activity of the fragments L2 and L4 was further tested using constructs driven by the promoter 35S (FIG. 8(A); pUC35GUS, pUC35SNGUS, pUC35SdnmGUS, pUS35SL2GUS, and pUC35S14GUS, referred to as GUS, Delta*, L2 and L4 respectively, in FIG. 8(B)). The fragments were removed from the pUC-based constructs by cutting with EcoRI and HindIII. The fragments were transferred to the vector pCAMBIA for transformation using Agrobacterium. Transformation of Arabidopsis plants was done as described in Clough S J, Bent A F: Floral dip: a simplified method for Agrobacterium-mediated transformation of *Arabidopsis thaliana*. Plant J. 16: 735–743 (1998).

The results (FIG. 8(B)) show that L2 produces an increase in activity over the reference construct, 35SGUS, and the construct containing L4. However the increase seen by 35SdN$^m$GUS is higher."

Pea Protoplasts

To determine the effect of L2 and L4 in other system, constructs containing either tCUP, 35SL2, 35SN, 35SL4 and 35S and the marker gene GUS (FIG. 8(A)) were electroporated into protoplasts.

Pea (*Pisum sativum* L. var.LaxtonProgress) seedlings were grown in soil at 18° C. (16 hr light, 8 hr dark; 15–20 $\mu$mol m$^{-2}$ S$^{-1}$) provided by philips (USA) F20 T12 'cool white' flourescent tubes and young filly expanded leaves were harvested from 2–3 weeks old plants. Leaves surface sterilized 5 minutes in 5% commercial bleach (Javex) (1% NaOCl). The abaxial surface of leaves were gently rubbed with carborandum powder, rinsed three times with sterile water, midribs removed and remaining leafblade was cut by sharp razor into ca 1 cubic cm pieces and floated rubbed surface facing first enzyme solution containing 0.1% (w/v) pectolyase Y-23 (Seishin Pharmaceutical, Japan), 0.5% potassium dextran sulphate (Calbiochem, USA) and 0.5 M mannitol (pH 5.5) and vacuum infiltrated for 15 minutes. The leaf tissues were then incubated at 26° C. for another 15 minutes on a shaker at 60 excursions/min. The solution was then decanted by filtration through a 100 mesh nylon filter and the remaining tissue was incubated for 1–1.5 hr in a second enzyme solution containing 1.0% (w/v) Cellulase Onozukak R-10 (Yakult Honsha, Japan), Pectolyase Y-23 0.05% (w/v) (Seishin Pharmaceutical, Japan and 0.5 M mannitol, pH 6.0 at 26° C. with 60 excursions/min.

The protoplasts were collected by filtration through a 100 $\mu$m nylon mesh filter followed by centrifugation at 500 rpm for 5 min. The protoplasts pellet was washed twice with W5 electroporation buffer (4.5 g NaCl, 0.5 g glucose, 9.2 g CaCl$_2$, 2.0 g KCl in 500 ml) for 5 min at 500 rpm and finally suspended at approximately 1×10$^6$/ml in 0.5 M mannitol containing 150 mM KCl.

The viability of protoplasts was confirmed by FDA (Fluorescin diacetate) staining and protoplasts were kept at 4° C. for 1 hr prior to electroporation. A 25–30 $\mu$g luciferin and desired DNA was added to 500 $\mu$l protoplast suspension, mixed gently and electroporated at 100 $\mu$F and 225 V using Gene Pulser II (BioRad). The electroporated protoplasts were diluted in 4 ml of growth buffer, centrifuged for 5 min at 500 rpm and mixed with 0.5 ml growth medium. The cultures were incubated in dark at 25° C. for 24 hr.

To each 500 $\mu$l of protoplast suspension 200 $\mu$l of buffer solution containing 100 mM KPO$_4$ 1 mM EDTA, 10% glycerol, 0.5% trion x-100, 7 mM $\beta$-merceptoethanol was added and protoplasts were lysed and luciferase and GUS activities were measured as described (Jefferson, R. A. 1987. Assaying chimeric genes in plants: the GUS fusion system. Plant Mol. Biol. Reporter 5:387–405; Mathews, F. B., Saunders J. A., Gebhardt J. S., Lin J-J., and Koehler M. 1995. Reporter genes and transient assays for plants. In "Methods in Molecular Biology, Vol 55: Plant Cell Electroporation and Electrofusion Protocols" ed. J. A. Nickoloff Humana Press Inc., Totowa, N.J. pp.147–162). All GUS activities were normalized with respect to luciferase activities to account for variation caused by electroporation The results (FIG. 8(C)) show that L2 increase the level of expression of the reference construct, 35S and L2 is more efficient at doing so than the full length NdeI-SmaI fragment, N, or the fragment L4. These results demonstrate that constructs comprising L2 operate in alternate plant systems, and further support the findings obtained using the yeast system.

Activity of L2 and L4 in Other Systems

The constructs 35SL2, 35SL4, 35SN and 35S (FIG. 8(A)) were bombarded in tobacco leaf disks as described above. As shown in FIG. 8(D) the fragment L2 produces an increase above the level of the reference construct, pUC35SGUS, and the construct containing L4. The increase in the level of activity produced by L2 is lower that the increase observed with the fragment N (pUC35SNGUS). The increase by L2 and N linked to the promoter 35S was less than the increase observed when those fragments were associated with the promoter tCUP2 (see FIG. 7(B)).

The constructs 35SL2, 35SL4, 35SdN$^m$ and 35S (FIG. 8(A)) were bombarded in alfalfa cell suspension culture as described above. The results (FIG. 8(E)) show that an increase was observed for the construct containing L4 when compared to the reference construct and that increase was similar to the increase observed with the fragment dN$^m$. No increase was observed with L2 in these experiments.

The constructs 35SL2, 35SL4, 35Sdelta* and 35S were also bombarded in corn callus culture as described above.

Transient GUS gene expression was determined by a histochemical assay (Jefferson 1988, supra) and by recording the number of GUS reporter gene expression events as indicated by the number of blue foci per explant or Petri dish. The results (FIG. 8(F)) show that L4 produced an increase in the level of activity over the level in the reference construct (35SGUS) while no significative increase was observed with L2. The increase observed with 35Sdelta* was stronger than with L4.

The constructs 35SL2, 35SL4, 35SdN$^m$ and 35S (FIG. 8(A)) were also bombarded in white spruce callus as described above. The results (FIG. 8(G)) show that an increase was observed for constructs containing either L2 and L4 when compared to the reference construct. However that increase was much weaker than the increase observed with the fragment dN$^m$.

Collectively, the results show that the expression of the fragments L2 and L4 associated with the promoter 35S followed the same trend as when using the tCUP2 promoter. However the enhancement was smaller.

Bacteria

Figure 10A:
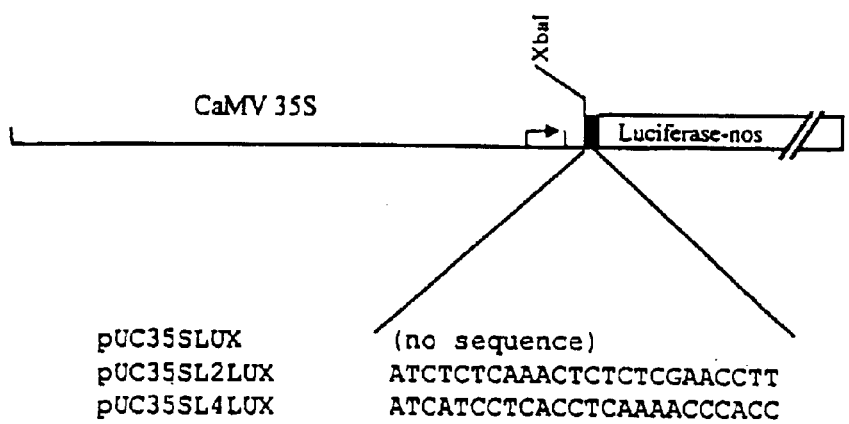
FIG. 10 shows fragments of dN$^m$, and their associated activities in the bacterium *Escherichia coli*.

The activity of the fragments L2 and L4 (FIG. 10(A); SEQ ID NO's:6 and 8) was also tested in the bacterium *E. coli*. *E. coli* was transformed with the luciferase gene from pEPLUX (White et al., 1994, Plant Physiol. 106: 917–928) which comprises the promoter 35S linked to LUX. p35SL2LUX and p35SL4LUX contain L2 or L4 respectively, upstream of the luciferase ATG (FIG. 10(A)). Determination of luciferase activity is by a whole cell assay and luminesence is measured by a luminometer at a 30 second integration time. −206TAP is a construct used as a negative control as it does not carry the luciferase gene.

The results (FIG. 10(B)) show that both fragments are enhancing the level of luciferase activity when compared to a construct containing none of the L fragments.

Derivatives of L2

The characterization of some of the derivatives of L2, including SCAN3, SCAN7 and 2×L2 (FIGS. 7(A) and 9(A); SEQ ID NO's: 17, 21 and 22) was performed in plants and conifers.

The constructs pUCtCUP2L2GUS, pUCtCUP2SCAN3GUS, pUCtCUP2SCAN7GUS and pUCtCUP2(−N)GUS (FIG. 7(A)) were evaluated by transient assay in tobacco leaf disks as described before. The results (FIG. 9(B)) show that the nucleotides modified in SCAN3 and SCAN 5 are critical for enhancing activity of L2 in plants as well as in yeast (see above).

Figure 9D:
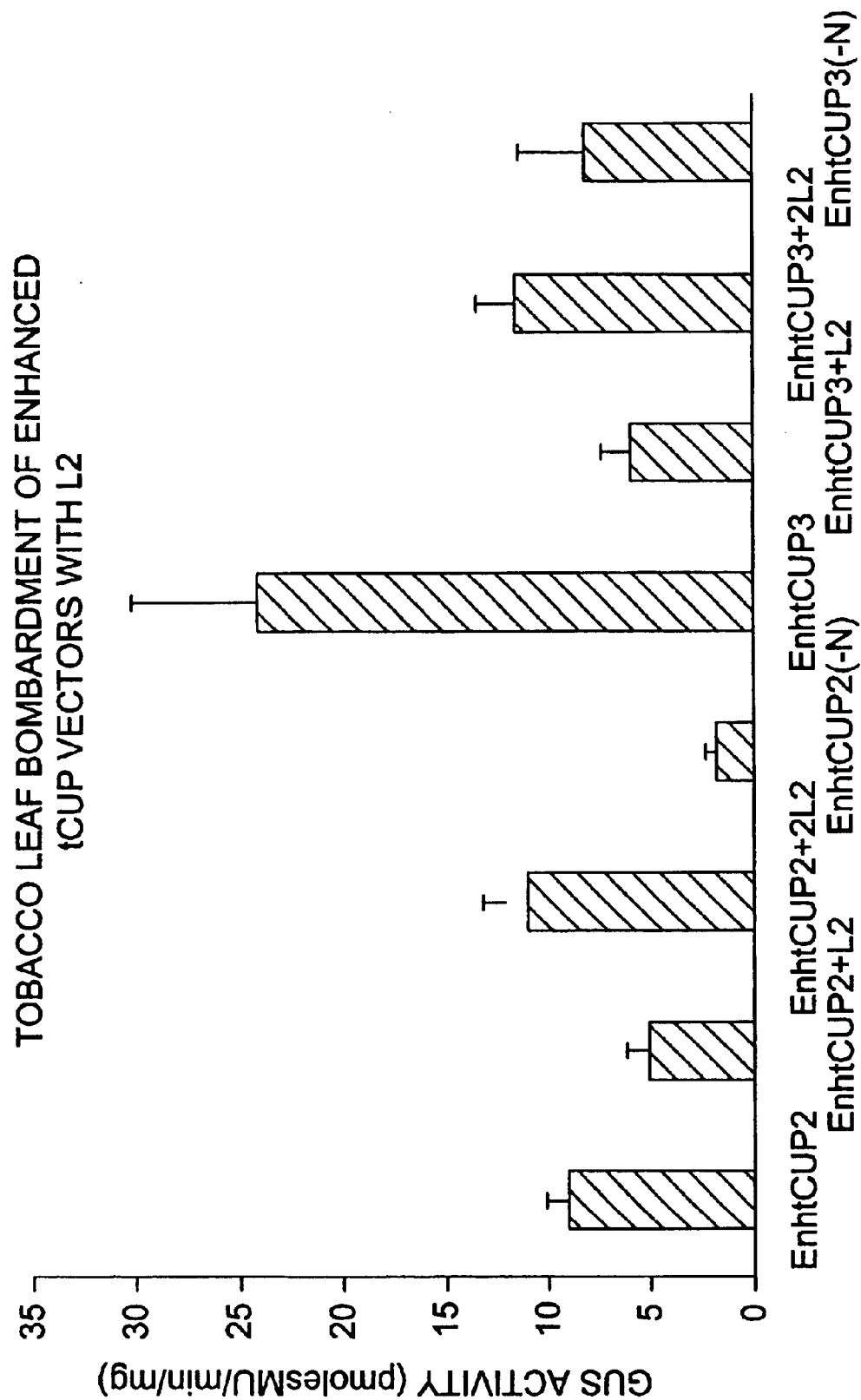
Figure 9E:
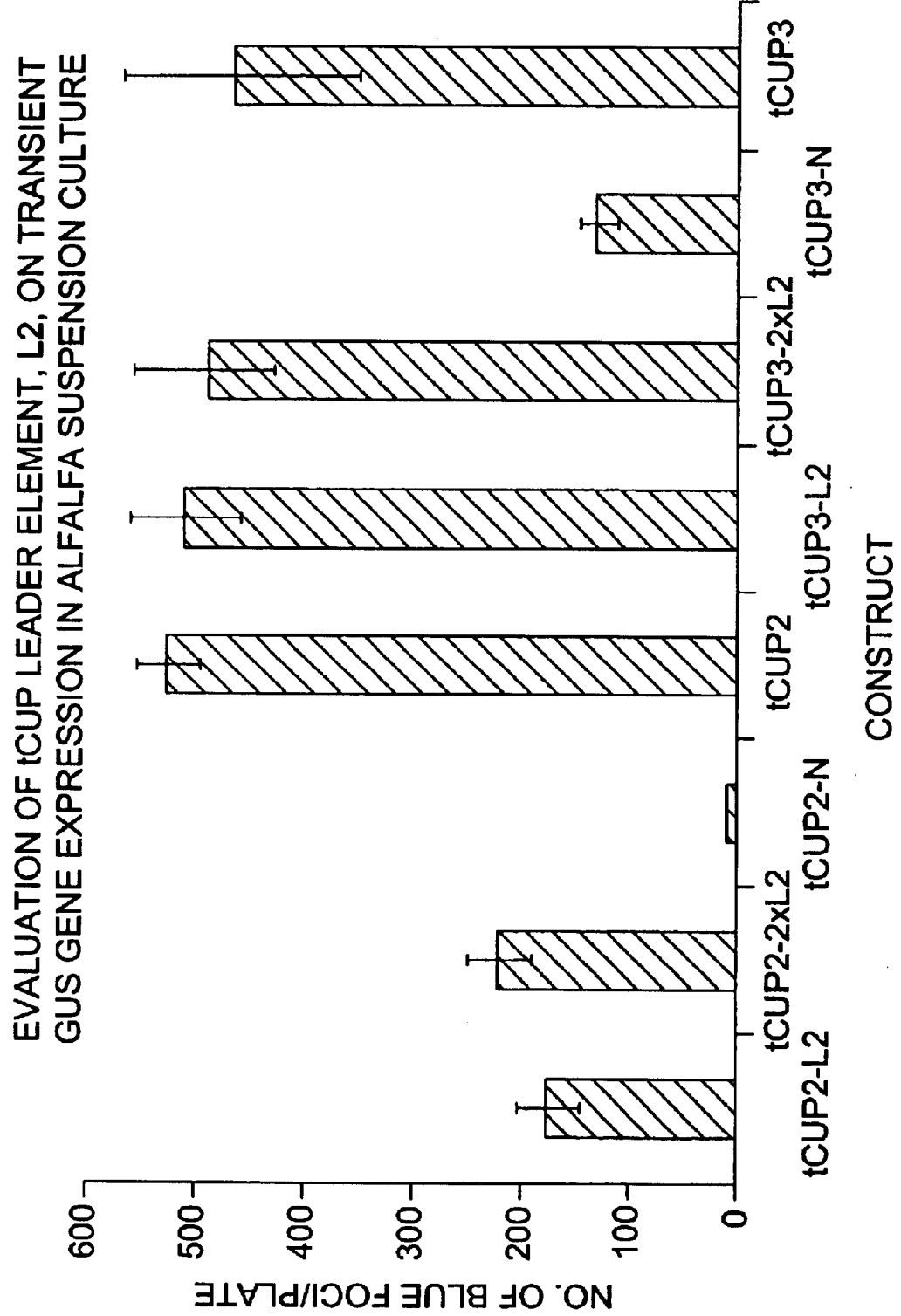
Figure 9F:
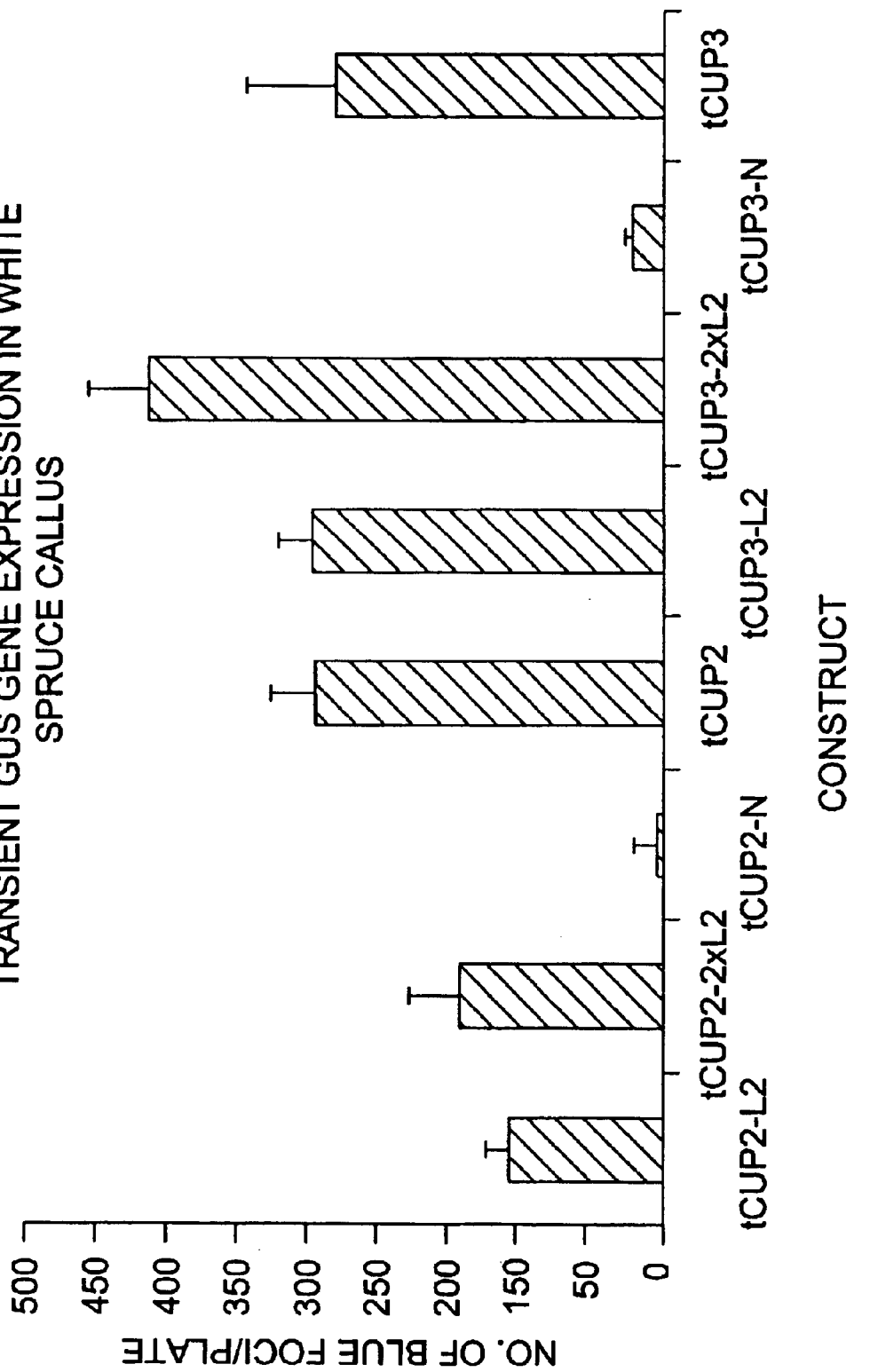

The use of L2 in tandem (2×L2) was tested in Arabidopsis by stable transformation (FIGS. 9(C)), and in tobacco, alfalfa and white spruce by transient assay (FIGS. 9(D) to (F)). Collectively, these results show that the tandem version of L2 (2×L2) increases the enhancement activity over that of L2 in the most of the systems tested. The enhancement by the fragment 2×L2 is often as high or higher than the one observed with the corresponding construct containing dN$^m$ (tCUP2GUS or tCUP3 GUS). A difference in the increase observed after oligomerisation (ie with 2×L2) was noted between the promoters used (tCUP2 vs tCUP3) and also between either species or assay type (transient vs stable expression).

Insects

The activity of L2 and an oligomer of L2 (3×L2, referred to as Short 3 mer) was tested in insect cells, as described above, using constructs illustrated in FIG. 11 (top panel). The results (FIG. 11, bottom panel) show that L2 has an inhibitory effect on level of activity when compared with the reference construct, p2Zop-2E-CAT. The inhibitory effect is much stronger when the fragment 3×L2 is used in the construct.

Collectively, these result indicate that constructs comprising "N", ΔN, ΔN$^M$, L2, fragments of L2, including L2C and L2R, analogs of L2 (e.g. SCAN1, SCAN2, SCAN4, SCAN 5 and SCAN6, B1–L2 and B7–L2), derivatives of L2 (e.g. 2×L2). L1, L3, L4 and L5 can function as translational enhancers within a variety of expression systems and hosts. All citations are herein incorporated by reference.

The present invention has been described with regard to preferred embodiments. However, it will be obvious to persons skilled in the art that a number of variations and modifications can be made without departing from the scope of the invention as described herein.

---

What is claimed is:

1. An isolated nucleic acid consisting of the nucleotide sequence of SEQ ID NO: 6.

2. A construct consisting of, one or more than one isolated nucleic acid as defined by claim 1 in operative association with a gene of interest, and in operative association with one or more than one regulatory element required for the expression of the gene of interest within a host organism.

3. The construct of claim 2, wherein the one or more than one regulatory element comprises a regulatory element selected from the group consisting of an inducible promoter, a developmentally regulated promoter, a tissue specific promoter, a constitutive promoter, and an enhancer element.

4. An isolated nucleic acid consisting of nucleotides 1–16 of the nucleotide sequence of SEQ ID NO: 6.

5. A construct consisting of, one or more than one isolated nucleic acid as defined by claim 4 in operative association with a gene of interest, and in operative association with one or more than one regulatory element required for the expression of the gene of interest within a host organism.

6. The construct of claim 5, wherein the one or more than one regulatory element comprises a regulatory element selected from the group consisting of an inducible promoter, a developmentally regulated promoter, a tissue specific promoter, a constitutive promoter, and an enhancer element.

7. An isolated nucleic acid consisting of nucleotides 10–24 of the nucleotide sequence of SEQ ID NO: 6.

8. A construct consisting of, one or more than one isolated nucleic acid as defined by claim 7 in operative association with a gene of interest, and in operative association with one or more than one regulatory element required for the expression of the gene of interest within a host organism.

9. The construct of claim 8, wherein the one or more than one regulatory element comprises a regulatory element selected from the group consisting of an inducible promoter, a developmentally regulated promoter, a tissue specific promoter, a constitutive promoter, and an enhancer element.

10. An isolated nucleic acid consisting of two copies of the nucleotide sequence of SEQ ID NO: 6.

11. A construct consisting of the isolated nucleic acid as defined by claim 10 in operative association with a gene of interest, and in operative association with one or more than one regulatory element required for the expression of the gene of interest within a host organism.

12. The construct of claim 11, wherein the regulatory element comprises a regulatory element selected from the group consisting of an inducible promoter, a developmentally regulated promoter, a tissue specific promoter, a constitutive promoter, and an enhancer element.

* * * * *